United States Patent
Ikeda

(10) Patent No.: US 12,111,574 B2
(45) Date of Patent: Oct. 8, 2024

(54) RESIST COMPOSITION, METHOD OF FORMING RESIST PATTERN, COMPOUND, AND RESIN

(71) Applicant: TOKYO OHKA KOGYO CO., LTD., Kawasaki (JP)

(72) Inventor: Takuya Ikeda, Kawasaki (JP)

(73) Assignee: TOKYO OHKA KOGYO CO., LTD., Kawasaki (JP)

( * ) Notice: Subject to any disclaimer, the term of this patent is extended or adjusted under 35 U.S.C. 154(b) by 329 days.

(21) Appl. No.: 17/547,044

(22) Filed: Dec. 9, 2021

(65) Prior Publication Data
US 2022/0206385 A1 Jun. 30, 2022

(30) Foreign Application Priority Data

Dec. 23, 2020 (JP) ................................ 2020-214126
Feb. 18, 2021 (JP) ................................ 2021-024646

(51) Int. Cl.
| | | |
|---|---|---|
| *G03F 7/039* | (2006.01) | |
| *C07C 69/54* | (2006.01) | |
| *C08F 212/14* | (2006.01) | |
| *C08F 220/18* | (2006.01) | |
| *G03F 7/004* | (2006.01) | |
| *G03F 7/038* | (2006.01) | |

(52) U.S. Cl.
CPC .............. *G03F 7/039* (2013.01); *C07C 69/54* (2013.01); *C08F 212/24* (2020.02); *C08F 220/1805* (2020.02); *C08F 220/1806* (2020.02); *C08F 220/1807* (2020.02); *C08F 220/1808* (2020.02); *C08F 220/1811* (2020.02); *G03F 7/0045* (2013.01); *G03F 7/038* (2013.01)

(58) Field of Classification Search
CPC ........ G03F 7/039; G03F 7/0045; G03F 7/038; G03F 7/004; G03F 7/0382; G03F 7/20; G03F 7/26; C07C 69/54; C07D 309/06; C08F 212/24; C08F 220/1805; C08F 220/1806; C08F 220/1807; C08F 220/1808; C08F 220/1811
USPC ........................................................ 430/270.1
See application file for complete search history.

(56) References Cited

U.S. PATENT DOCUMENTS

2014/0356787 A1* 12/2014 Komuro .................. G03F 7/027
430/281.1

FOREIGN PATENT DOCUMENTS

| JP | 2008268741 A | * 11/2008 | ............. G03F 7/039 |
| JP | 2009-084490 A | 4/2009 | |

OTHER PUBLICATIONS

Machine Translation of JP 2008-268741 A (Year: 2008).*

* cited by examiner

*Primary Examiner* — Sean M DeGuire
*Assistant Examiner* — Andrew Preston Traywick
(74) *Attorney, Agent, or Firm* — Knobbe, Martens, Olson & Bear, LLP

(57) ABSTRACT

A resist composition containing a polymeric compound having a constitutional unit (a01) derived from a compound represented by General Formula (a0-1). In the formula, $W^{01}$ represents a polymerizable group-containing group, $Ra^{01}$ represents a linear or branched hydrocarbon group, and $Ra^{02}$ and $Ra^{03}$ each independently represents a hydrocarbon group which may have a substituent

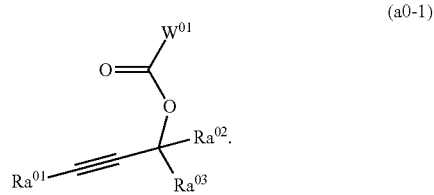

(a0-1)

11 Claims, No Drawings

RESIST COMPOSITION, METHOD OF FORMING RESIST PATTERN, COMPOUND, AND RESIN

BACKGROUND OF THE INVENTION

Field of the Invention

The present invention relates to a resist composition, a method of forming a resist pattern, a compound, and a resin.

Priority is claimed on Japanese Patent Application No. 2020-214126, filed on Dec. 23, 2020, and Japanese Patent Application No. 2021-024646, filed on Feb. 18, 2021, the contents of which are incorporated herein by reference.

Description of Related Art

In recent years, in the production of semiconductor elements and liquid crystal display elements, advances in lithography techniques have led to a rapid progress in the field of pattern fining. Typically, these pattern fining techniques involve shortening the wavelength (increasing the energy) of the light source for exposure.

Resist materials for use with these types of light sources for exposure require lithography characteristics such as a high resolution capable of reproducing a fine-sized pattern, and a high level of sensitivity to these types of light sources for exposure.

As a resist material that satisfies these requirements, a chemically amplified resist composition containing a base material component that exhibits changed solubility in a developing solution under action of acid, and an acid generator component that generates acid upon exposure has been used in the related art.

In the chemically amplified resist composition, a resin having a plurality of constitutional units is generally used for improving the lithography characteristics.

For example, Patent Document 1 discloses a copolymer having a uniform molecular weight, which is useful as a resist material, and has a specific constitutional unit containing a triple bond and a specific constitutional unit containing a group having a lactone ring.

CITATION LIST

Patent Document

[Patent Document 1] Japanese Unexamined Patent Application, First Publication No. 2009-84490

SUMMARY OF THE INVENTION

With the further progress of lithography technology and resist pattern fining, for example, it is aimed to form a fine pattern of several tens of nanometers in lithography by EUV and EB. As the resist pattern size becomes smaller as described above, good lithography characteristics such as the high sensitivity to the exposure light source, the critical dimension uniformity (CDU) of the pattern size, and the resolution are required.

However, in the resist composition containing such a conventional resin as described above, in a case where the sensitivity to an exposure light source was increased, a desired resist pattern shape or the like was not easily obtained, and thus it was difficult to achieve all of the above characteristics.

The present invention has been made in consideration of the above circumstances, and an object of the present invention is to provide a resist composition with which high sensitivity is further achieved and a resist pattern having good CDU and good resolution can be formed, a method of forming a resist pattern using the resist composition, a resin useful for the resist composition, and a compound useful for the production of the resin.

In order to achieve the above-described object, the present invention employs the following configurations.

That is, the first aspect according to the present invention is a resist composition that generates acid upon exposure and exhibits changed solubility in a developing solution under action of acid. The resist composition contains a resin component (A1) that exhibits changed solubility in a developing solution under action of acid. The resin component (A1) has a constitutional unit (a01) derived from a compound represented by General Formula (a0-1).

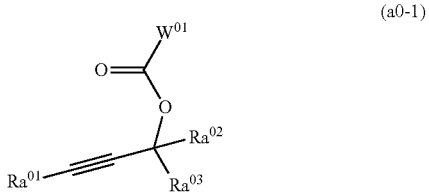

(a0-1)

[In the formula, $W^{01}$ represents a polymerizable group-containing group. $Ra^{01}$ represents a linear or branched hydrocarbon group. $Ra^{02}$ and $Ra^{03}$ each independently represent a hydrocarbon group which may have a substituent.]

The second aspect according to the present invention is a method of forming a resist pattern, including a step of forming a resist film on a support using the resist composition according to the first aspect, a step of exposing the resist film, and a step of developing the exposed resist film to form a resist pattern.

The third aspect of the present invention is a compound represented by General Formula (a0-1).

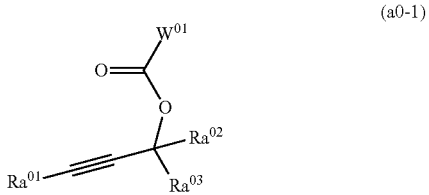

(a0-1)

[In the formula, $W^{01}$ represents a polymerizable group-containing group. $Ra^{01}$ represents a linear or branched hydrocarbon group. $Ra^{02}$ and $Ra^{03}$ each independently represent a hydrocarbon group which may have a substituent.]

The fourth aspect of the present invention is a resin having a constitutional unit (a01) derived from a compound represented by General Formula (a0-1).

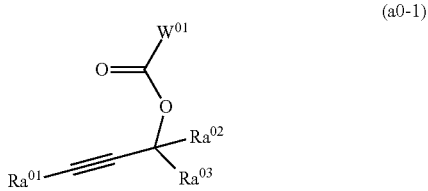

(a0-1)

[In the formula, $W^{01}$ represents a polymerizable group-containing group. $Ra^{01}$ represents a linear or branched hydrocarbon group. $Ra^{02}$ and $Ra^{03}$ each independently represent a hydrocarbon group which may have a substituent.]

According to the present invention, it is possible to provide a resist composition with which high sensitivity is further achieved and a resist pattern having good CDU and good resolution can be formed, a method of forming a resist pattern using the resist composition, a resin useful for the resist composition, and a compound useful for the production of the resin.

DETAILED DESCRIPTION OF THE INVENTION

In the present specification and the scope of the present claims, the term "aliphatic" is a relative concept that is used with respect to the term "aromatic", and it defines a group or compound that has no aromaticity.

The "alkyl group" includes a monovalent saturated hydrocarbon group that is linear, branched, or cyclic, unless otherwise specified. The same applies to the alkyl group of the alkoxy group.

The "alkylene group" includes a divalent saturated hydrocarbon group that is linear, branched, or cyclic, unless otherwise specified.

Examples of the "halogen atom" include a fluorine atom, a chlorine atom, a bromine atom, and an iodine atom.

The "constitutional unit" means a monomer unit (monomeric unit) that contributes to the formation of a polymeric compound (a resin, a polymer, or a copolymer).

In a case where "may have a substituent" is described, both of a case where a hydrogen atom (—H) is substituted with a monovalent group and a case where a methylene group (—$CH_2$—) is substituted with a divalent group are included.

The "exposure" is used as a general concept that includes irradiation with any form of radiation.

The "acid decomposable group" indicates a group in which at least part of bonds in the structure of the acid decomposable group can be cleaved under action of acid.

Examples of the acid decomposable group having a polarity that is increased under action of acid include groups which decompose under action of acid to generate a polar group.

Examples of the polar group include a carboxy group, a hydroxyl group, an amino group, and a sulfo group (—$SO_3H$).

More specific examples of the acid decomposable group include a group in which the above-described polar group has been protected with an acid dissociable group (for example, a group in which a hydrogen atom of the OH-containing polar group has been protected with an acid dissociable group).

The "acid dissociable group" indicates any one of (i) a group in which a bond between the acid dissociable group and an atom adjacent to the acid dissociable group can be cleaved under action of acid; and (ii) a group in which parts of bonds are cleaved under action of acid, and then a decarboxylation reaction occurs, thereby cleaving the bond between the acid dissociable group and the atom adjacent to the acid dissociable group.

It is necessary that the acid dissociable group that constitutes the acid decomposable group be a group that exhibits a lower polarity than the polar group generated by the dissociation of the acid dissociable group. Thus, in a case where the acid dissociable group is dissociated under action of acid, a polar group exhibiting a higher polarity than the acid dissociable group is generated, thereby increasing the polarity. As a result of the above, the polarity of the entire component (A1) is increased. By the increase in the polarity, the solubility in a developing solution relatively changes. The solubility in a developing solution is increased in a case where the developing solution is an alkali developing solution, whereas the solubility in a developing solution is decreased in a case where the developing solution is an organic developing solution.

The "base material component" is an organic compound having a film-forming ability. The organic compounds used as the base material component are roughly classified into a non-polymer and a polymer. As the non-polymer, those having a molecular weight of 500 or more and less than 4,000 are usually used. Hereinafter, a "low molecular weight compound" refers to a non-polymer having a molecular weight of 500 or more and less than 4,000. As the polymer, those having a molecular weight of 1,000 or more are usually used. Hereinafter, a "resin", a "polymeric compound", or a "polymer" refers to a polymer having a molecular weight of 1,000 or more. As the molecular weight of the polymer, a polystyrene-equivalent weight average molecular weight determined by gel permeation chromatography (GPC) is used.

A "constitutional unit derived from" means a constitutional unit that is formed by the cleavage of a multiple bond between carbon atoms, for example, an ethylenic double bond.

In the "acrylic acid ester", the hydrogen atom bonded to the carbon atom at the α-position may be substituted with a substituent. The substituent ($R^{\alpha x}$) that is substituted for the hydrogen atom bonded to the carbon atom at the α-position is an atom other than a hydrogen atom or a group. Further, itaconic acid diester in which the substituent ($R^{\alpha x}$) is substituted with a substituent having an ester bond or α-hydroxyacryl ester in which the substituent ($R^{\alpha x}$) is substituted with a hydroxyalkyl group or a group in which a hydroxyl group thereof is modified can be mentioned as an acrylic acid ester. A carbon atom at the α-position of acrylic acid ester indicates the carbon atom bonded to the carbonyl group of acrylic acid, unless otherwise specified.

Hereinafter, acrylic acid ester in which the hydrogen atom bonded to the carbon atom at the α-position is substituted with a substituent is also referred to as an "α-substituted acrylic acid ester".

The "derivative" includes a compound in which the hydrogen atom at the α-position of the object compound has been substituted with another substituent such as an alkyl group or a halogenated alkyl group; and derivatives thereof. Examples of the derivatives thereof include a derivative in which the hydrogen atom of the hydroxyl group of the object compound in which the hydrogen atom at the α-position may be substituted with a substituent is substituted with an organic group; and a derivative in which a substituent other than a hydroxyl group is bonded to the object compound in which the hydrogen atom at the α-position may be substituted with a substituent. The α-position refers to the first carbon atom adjacent to the functional group unless otherwise specified.

Examples of the substituent that is substituted for the hydrogen atom at the α-position of hydroxystyrene include the same one as $R^{\alpha x}$.

In the present specification and the scope of the present claims, asymmetric carbon atoms may be present, and thus enantiomers or diastereomers may be present depending on the structures represented by the chemical formula. In that case, these isomers are represented by one chemical formula. These isomers may be used alone or in the form of a mixture.

(Resist Composition)

The resist composition according to the present embodiment is a resist composition that generates acid upon exposure and exhibits changed solubility in a developing solution under action of acid.

The resist composition contains a base material component (A) (hereinafter, also referred to as a "component (A)") that exhibits changed solubility in a developing solution under action of acid.

In a case where a resist film is formed using the resist composition according to the present embodiment and the formed resist film is subjected to selective exposure, an acid is generated at exposed portions of the resist film, and the generated acid acts on the component (A) to change the solubility of the component (A) in a developing solution. On the other hand, the solubility of the component (A) in a developing solution is not changed at unexposed portions of the resist film, which generates the difference in solubility in the developing solution between exposed portions and unexposed portions of the resist film.

The resist composition according to the present embodiment may be a positive-tone resist composition or a negative-tone resist composition.

Further, in the formation of a resist pattern, the resist composition according to the present embodiment can be applied to an alkali developing process using an alkali developing solution in the developing treatment, or a solvent developing process using an organic developing solution in the developing treatment.

That is, the resist composition according to the present embodiment is a "positive-tone resist composition for an alkali developing process" that forms a positive-tone resist pattern in an alkali developing process and is a "negative-tone resist composition for a solvent developing process" that forms a negative-tone resist pattern in a solvent developing process.

<Component (A)>

In the resist composition according to the present embodiment, the component (A) contains a resin component (A1) (hereinafter, also referred to as a "component (A1))" that exhibits changed solubility in a developing solution under action of acid, and the resin component (A1) has a constitutional unit (a01) derived from a compound represented by General Formula (a0-1).

As the component (A), at least the component (A1) is used, and at least one of another polymeric compound and another low molecular weight compound may be used in combination with the component (A1).

In the resist composition according to the present embodiment, the component (A) may be used alone or in a combination of two or more kinds thereof.

In Regard to Component (A1)

The component (A1) has a constitutional unit (a01).

<<Constitutional Unit (a01)>>

The constitutional unit (a01) is a constitutional unit derived from a compound represented by General Formula (a0-1).

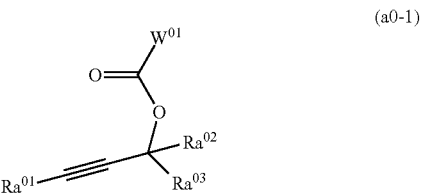

(a0-1)

[In the formula, $W^{01}$ represents a polymerizable group-containing group. $Ra^{01}$ represents a linear or branched hydrocarbon group. $Ra^{02}$ and $Ra^{03}$ each independently represent a hydrocarbon group which may have a substituent.]

In General Formula (a0-1), $W^{01}$ represents a polymerizable group-containing group.

The "polymerizable group" as $W^{01}$ is a group that enables a compound having the polymerizable group to be polymerized by radical polymerization or the like, and includes a group containing a multiple bond between carbon atoms, such as an ethylenic double bond.

In the constitutional unit (a01), the multiple bonds in the polymerizable group are cleaved to form a main chain.

Examples of the polymerizable group as $W^{01}$ include a vinyl group, an allyl group, acryloyl group, a methacryloyl group, a fluorovinyl group, a difluorovinyl group, a trifluorovinyl group, a difluorotrifluoromethylvinyl group, a trifluoroallyl group, a perfluoroallyl group, a trifluoromethylacryloyl group, a nonylfluorobutylacryloyl group, a vinyl ether group, a fluorine-containing vinyl ether group, an allyl ether group, a fluorine-containing allyl ether group, a styryl group, and a vinylnaphthyl group, a fluorine-containing styryl group, a fluorine-containing vinylnaphthyl group, a norbornyl group, a fluorine-containing norbornyl group, and a silyl group.

The "polymerizable group-containing group" as $W^{01}$ may be a group composed of only a polymerizable group, or a group composed of a polymerizable group and a group other than the polymerizable group. Examples of the group other than the polymerizable group include a divalent hydrocarbon group which may have a substituent and a divalent linking group containing a hetero atom.

Divalent Hydrocarbon Group which May have Substituent:

In a case where the group other than the polymerizable group represents a divalent hydrocarbon group which may have a substituent, the hydrocarbon group may be an aliphatic hydrocarbon group or an aromatic hydrocarbon group.

Aliphatic Hydrocarbon Group as a Group Other than the Polymerizable Group

The aliphatic hydrocarbon group indicates a hydrocarbon group that has no aromaticity. The aliphatic hydrocarbon group may be saturated or unsaturated. In general, it is preferable that the aliphatic hydrocarbon group is saturated.

Examples of the aliphatic hydrocarbon group include a linear or branched aliphatic hydrocarbon group, and an aliphatic hydrocarbon group containing a ring in the structure thereof.

Linear or Branched Aliphatic Hydrocarbon Group

The linear aliphatic hydrocarbon group described above preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group described above preferably has 2 to 10 carbon atoms, more preferably 3 to 6 carbon atoms, still more preferably 3 or 4 carbon atoms, and most preferably 3 carbon atoms.

The branched aliphatic hydrocarbon group is preferably a branched alkylene group, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

The above linear or branched aliphatic hydrocarbon group may have or may not have a substituent. Examples of the substituent include a fluorine atom, a fluorinated alkyl group having 1 to 5 carbon atoms, which has been substituted with a fluorine atom, and a carbonyl group.

Aliphatic Hydrocarbon Group Containing Ring in Structure Thereof

Examples of the aliphatic hydrocarbon group containing a ring in the structure thereof include a cyclic aliphatic hydrocarbon group which may have a substituent containing a hetero atom in the ring structure thereof (a group obtained by removing two hydrogen atoms from an aliphatic hydrocarbon ring), a group obtained by bonding a cyclic aliphatic hydrocarbon group to the terminal of a linear or branched aliphatic hydrocarbon group, and a group obtained by interposing a cyclic aliphatic hydrocarbon group in a linear or branched aliphatic hydrocarbon group. Examples of the above linear or branched aliphatic hydrocarbon group include the same ones as those described above.

The cyclic aliphatic hydrocarbon group preferably has 3 to 20 carbon atoms and more preferably 3 to 12 carbon atoms.

The cyclic aliphatic hydrocarbon group may be a polycyclic group or a monocyclic group. The monocyclic alicyclic hydrocarbon group is preferably a group obtained by removing two hydrogen atoms from a monocycloalkane. The monocycloalkane preferably has 3 to 6 carbon atoms, and specific examples thereof include cyclopentane and cyclohexane. The polycyclic alicyclic hydrocarbon group is preferably a group obtained by removing two hydrogen atoms from a polycycloalkane, and the polycycloalkane is preferably a group having 7 to 12 carbon atoms. Specific examples thereof include adamantane, norbornane, isobornane, tricyclodecane, and tetracyclododecane.

The cyclic aliphatic hydrocarbon group may have or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and most preferably a methyl group, an ethyl group, a propyl group, an n-butyl group, or a tert-butyl group.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom for the substituent include a fluorine atom, a chlorine atom, a bromine atom, and an iodine atom, and a fluorine atom is preferable.

Examples of the halogenated alkyl group as the substituent include a group obtained by substituting part or all of hydrogen atoms in the above-described alkyl group with the above-described halogen atom.

In the cyclic aliphatic hydrocarbon group, part of carbon atoms constituting the ring structure thereof may be substituted with a substituent containing a hetero atom. The substituent containing a hetero atom is preferably —O—, —C(=O)—O—, —S—, —S(=O)$_2$—, or —S(=O)$_2$—O—.

Aromatic Hydrocarbon Group as Group Other than the Polymerizable Group

The aromatic hydrocarbon group is a hydrocarbon group having at least one aromatic ring.

The aromatic ring is not particularly limited as long as it is a cyclic conjugated system having $(4n+2)\pi$ electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Here, the number of carbon atoms in a substituent is not included in the number of carbon atoms. Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group include a group (an arylene group or a heteroarylene group) obtained by removing two hydrogen atoms from the above-described aromatic hydrocarbon ring or the above-described aromatic heterocyclic ring; a group obtained by removing two hydrogen atoms from an aromatic compound (for example, biphenyl or fluorene) having two or more aromatic rings; and a group (for example, a group obtained by further removing one hydrogen atom from an aryl group in the arylalkyl group such as a benzyl group, a phenethyl group, a 1-naphthylmethyl group, a 2-naphthylmethyl group, a 1-naphthylethyl group, or a 2-naphthylethyl group) obtained by substituting one hydrogen atom of a group (an aryl group or a heteroaryl group) obtained by removing one hydrogen atom from the above aromatic hydrocarbon ring or the above aromatic heterocyclic ring, with an alkylene group. The above alkylene group bonded to the aryl group or the heteroaryl group preferably has 1 to 4 carbon atoms, more preferably 1 or 2 carbon atoms, and particularly preferably 1 carbon atom.

With respect to the aromatic hydrocarbon group, the hydrogen atom contained in the aromatic hydrocarbon group may be substituted with a substituent. For example, the hydrogen atom bonded to the aromatic ring in the aromatic hydrocarbon group may be substituted with a substituent.

Examples of substituents include an alkyl group, an alkoxy group, a halogen atom, a halogenated alkyl group, and a hydroxyl group.

The alkyl group as the substituent is preferably an alkyl group having 1 to 5 carbon atoms, and most preferably a methyl group, an ethyl group, a propyl group, an n-butyl group, or a tert-butyl group.

Examples of the alkoxy group, the halogen atom, and the halogenated alkyl group, as the substituent, include the same groups as those exemplified as the substituent that is substituted for a hydrogen atom contained in the cyclic aliphatic hydrocarbon group.

Divalent Linking Group Containing Hetero Atom:

In a case where the group other than the polymerizable group represents a divalent linking group containing a hetero atom, preferred examples of the linking group include —O—, —C(=O)—O—, —C(=O)—, —O—C(=O)—O— —C(=O)—NH—, —NH—, —NH—C(=NH)—(H may be substituted with a substituent such as an alkyl group, an acyl group, or the like), —S—, —S(=O)$_2$—, —S(=O)$_2$—O—, and a group represented by General Formula: —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$— or—Y$^{21}$—S(=O)$_2$—O—Y$^{22}$— [in the formulae, Y$^2$ and Y$^{22}$ each independently represent a divalent hydrocarbon group which may have a substituent, O represents an oxygen atom, and m" represents an integer in a range of 0 to 3].

In a case where the above divalent linking group containing a hetero atom is —C(=O)—NH—, —C(=O)—NH—C(=O)—, —NH—, or —NH—C(=NH)—, H may be substituted with a substituent such as an alkyl group, an acyl group, or the like. The substituent (an alkyl group, an acyl group, or the like) preferably has 1 to 10 carbon atoms, more preferably 1 to 8 carbon atoms, and particularly preferably 1 to 5 carbon atoms.

In General Formulae —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$—, and —Y$^{21}$—S(=O)$_2$—O—Y$^{22}$—, and Y$^{21}$, and Y$^{22}$ each independently represent a divalent hydrocarbon group which may have a substituent. Examples of the divalent hydrocarbon group include the same one as the divalent hydrocarbon group which may have a substituent, mentioned in the explanation of the above-described divalent linking group.

Y$^{21}$ is preferably a linear aliphatic hydrocarbon group, more preferably a linear alkylene group, still more preferably a linear alkylene group having 1 to 5 carbon atoms, and particularly preferably a methylene group or an ethylene group.

Y$^{22}$ is preferably a linear or branched aliphatic hydrocarbon group and more preferably a methylene group, an ethylene group, or an alkylmethylene group. The alkyl group in the alkylmethylene group is preferably a linear alkyl group having 1 to 5 carbon atoms, more preferably a linear alkyl group having 1 to 3 carbon atoms, and most preferably a methyl group.

In the group represented by General Formula —[Y$^{21}$—C(=O)—O]$_{m''}$—Y$^{22}$—, —, m" represents an integer in a range of 0 to 3, preferably an integer in a range of 0 to 2, more preferably 0 or 1, and particularly preferably 1. In other words, it is particularly preferable that the group represented by Formula —[Y$^{21}$—C(=O)—O]$_{m''}$—Y$^{22}$— represents a group represented by Formula —Y$^{21}$—C(=O)—O—Y$^{22}$—. Among them, a group represented by Formula —(CH$_2$)$_{a'}$—C(=O)—O—(CH$_2$)$_{b'}$— is preferable. In the formula, a' represents an integer in a range of 1 to 10, preferably an integer in a range of 1 to 8, more preferably an integer in a range of 1 to 5, still more preferably 1 or 2, and most preferably 1. b' represents an integer in a range of 1 to 10, preferably an integer in a range of 1 to 8, more preferably an integer in a range of 1 to 5, still more preferably 1 or 2, and most preferably 1.

Suitable examples of W$^{01}$ include a group represented by a chemical formula: C(R$^{X11}$)(R$^{X12}$)=C(R$^{X13}$)-Ya$^{x0}$.

In the chemical formula, R$^{X11}$, R$^{X12}$, and R$^{X13}$ each represent a hydrogen atom, an alkyl group having 1 to 5 carbon atoms, or a halogenated alkyl group having 1 to 5 carbon atoms, and Ya$^{x0}$ represents a single bond or a divalent linking group.

The alkyl group having 1 to 5 carbon atoms as R$^{X11}$, R$^{X12}$, and R$^{X13}$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group obtained by substituting part or all of hydrogen atoms in the alkyl group having 1 to 5 carbon atoms with a halogen atom. The halogen atom is particularly preferably a fluorine atom.

Among these, R$^{X11}$ and R$^{X12}$ are each preferably a hydrogen atom, an alkyl group having 1 to 5 carbon atoms, or a fluorinated alkyl group having 1 to 5 carbon atoms, and in terms of industrial availability, a hydrogen atom or a methyl group is more preferable, and a hydrogen atom is particularly preferable.

In addition, R$^{X13}$ is preferably a hydrogen atom, an alkyl group having 1 to 5 carbon atoms, or a fluorinated alkyl group having 1 to 5 carbon atoms, and in terms of industrial availability, a hydrogen atom or a methyl group is more preferable, and a methyl group is particularly preferable.

The divalent linking group as Ya$^{x0}$ is not particularly limited, and suitable examples thereof include a divalent hydrocarbon group which may have a substituent and a divalent linking group having a hetero atom, each of which is the same as that described above.

Among the above, Ya$^{x0}$ is preferably an ester bond [—C(=O)—O— or —O—C(=O)—], an ether bond (—O—), a linear or branched alkylene group, an aromatic hydrocarbon group, or a combination thereof, or a single bond. Among these, Ya$^{x0}$ is more preferably a combination of an ester bond [—C(=O)—O— or —O—C(=O)—] with a linear alkylene group, or a single bond, and still more preferably a single bond.

In General Formula (a0-1), Ra$^{01}$ represents a linear or branched hydrocarbon group.

The linear or branched hydrocarbon group preferably has 1 to 10 carbon atoms, more preferably 1 to 6 carbon atoms, and still more preferably 1 to 4 carbon atoms.

Specific examples of the linear or branched hydrocarbon group as Ra$^{01}$ include a linear or branched saturated hydrocarbon group (an alkyl group) and a linear or branched unsaturated hydrocarbon group.

Specific examples of the linear or branched alkyl group include a methyl group, an ethyl group, a propyl group, an isopropyl group, an n-butyl group, an isobutyl group, a tert-butyl group, a pentyl group, an isopentyl group, and a neopentyl group.

More specific examples of the unsaturated hydrocarbon group in the linear or branched unsaturated hydrocarbon group include an unsaturated hydrocarbon group having a double bond, such as an alkenyl group, an alkadienyl group, or an alkatrienyl group; and an unsaturated hydrocarbon group having a triple bond, such as an alkynyl group, a group obtained by removing one hydrogen atom from a dialkyne, or a group obtained by removing one hydrogen atom from a trialkyne.

Specific examples of the linear or branched alkenyl group include a linear alkenyl group such as a vinyl group, a propenyl group (an allyl group), or a 2-butenyl group; and a branched alkenyl group such as a 1-methylvinyl group, a 2-methylvinyl group, a 1-methylpropenyl group, or 2-methylpropenyl group.

Specific examples of the alkadienyl group include a propadienyl group and a butadienyl group.

Specific examples of the alkatrienyl group include a butatrienyl group.

Specific examples of the linear or branched alkynyl group include a linear alkynyl group such as an ethynyl group, a propargyl group, or a 3-pentynyl group; and a branched alkynyl group such as a 1-methylpropargyl group.

Specific examples of the group obtained by removing one hydrogen atom from the dialkyne include a group obtained by removing one hydrogen atom from diacetylene.

Specific examples of the group obtained by removing one hydrogen atom from the trialkyne include a group obtained by removing one hydrogen atom from hexa-1,3,5-triyne.

In General Formula (a0-1), $Ra^{o1}$ is, among them, preferably a linear or branched alkyl group or a linear or branched alkenyl group, and it is more preferably a linear or branched alkyl group.

In General Formula (a0-1), $Ra^{o2}$ and $Ra^{o3}$ each independently represent a hydrocarbon group which may have a substituent.

Examples of the hydrocarbon group as $Ra^{o2}$ and $Ra^{o3}$ include a linear, branched, or cyclic hydrocarbon group.

Examples of the linear or branched hydrocarbon group as $Ra^{o2}$ and $Ra^{o3}$ include the same one as the linear or branched hydrocarbon group as $Ra^{o1}$.

Examples of the cyclic hydrocarbon group as $Ra^{o2}$ and $Ra^{o3}$ include an aliphatic hydrocarbon group and an aromatic hydrocarbon group.

The aliphatic hydrocarbon group may be a polycyclic group or a monocyclic group.

The aliphatic hydrocarbon group which is a monocyclic group is preferably a group obtained by removing one hydrogen atom from a monocycloalkane. The monocycloalkane preferably has 3 to 6 carbon atoms, and specific examples thereof include cyclopentane and cyclohexane.

The aliphatic hydrocarbon group which is a polycyclic group is preferably a group obtained by removing one hydrogen atom from a polycycloalkane, where the polycycloalkane preferably has 7 to 12 carbon atoms. Specific examples thereof include adamantane, norbornane, isobornane, tricyclodecane, and tetracyclododecane.

The aromatic hydrocarbon group is a hydrocarbon group having at least one aromatic ring.

The aromatic ring is not particularly limited as long as it is a cyclic conjugated system having $(4n+2)\pi$ electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms.

Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom.

Specific examples of the aromatic heterocyclic ring include a pyridine ring and a thiophene ring.

Specific examples of the aromatic hydrocarbon group include a group obtained by removing one hydrogen atom from the above-described aromatic hydrocarbon ring or aromatic heterocyclic ring (an aryl group or a heteroaryl group); a group obtained by removing one hydrogen atom from an aromatic compound having two or more aromatic rings (biphenyl, fluorene or the like); and a group obtained by substituting one hydrogen atom of the above-described aromatic hydrocarbon ring or aromatic heterocyclic ring with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aromatic hydrocarbon ring or aromatic heterocyclic ring preferably has 1 to 4 carbon atoms, more preferably 1 or 2 carbon atoms, and particularly preferably 1 carbon atom.

The hydrocarbon group as $Ra^{o2}$ and $Ra^{o3}$ may have a substituent. Examples of the substituent include, $-R^{P1}$, $-R^{P2}-O-R^{P1}$, $-R^{P2}-CO-R^{P1}$, $-R^{P2}-CO-OR^{P1}$, $-R^{P2}-O-CO-R^{P1}$, $-R^{P2}-OH$, $-R^{P2}-CN$, and $-R^{P2}-COOH$ (hereinafter, these substituents are also collectively referred to as "$Ra^{x5}$").

Here, $R^{P1}$ represents a monovalent chain saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. In addition, $R^{P2}$ represents a single bond, a divalent chain saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms. However, part or all of hydrogen atoms included in the chain saturated hydrocarbon group, the aliphatic cyclic saturated hydrocarbon group, and the aromatic hydrocarbon group of $R^{P1}$ and $R^{P2}$ may be substituted with a fluorine atom. In the aliphatic cyclic hydrocarbon group, one or more of the above-described substituents may be included as a single kind, or one or more of the above-described substituents may be included as a plurality of kinds.

Examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include monocyclic aliphatic saturated hydrocarbon groups such as a cyclopropyl group, a cyclobutyl group, a cyclopentyl group, a cyclohexyl group, a cycloheptyl group, a cyclooctyl group, a cyclodecyl group, and cyclododecyl group; and polycyclic aliphatic saturated hydrocarbon groups such as a bicyclo[2.2.2]octanyl group, a tricyclo[5.2.1.02,6]decanyl group, a tricyclo [3.3.1.13,7]decanyl group, a tetracyclo [6.2.1.13,6.02,7] dodecanyl group, and an adamantyl group.

Examples of the monovalent aromatic hydrocarbon group having 6 to 30 carbon atoms include a group obtained by removing one hydrogen atom from an aromatic hydrocarbon ring such as benzene, biphenyl, fluorene, naphthalene, anthracene, or phenanthrene.

In General Formula (a0-1), $Ra^{o2}$ and $Ra^{o3}$ are each independently preferably a linear or branched hydrocarbon group, more preferably a linear or branched alkyl group or a linear or branched alkenyl group, and still more preferably a linear or branched alkyl group. The total number of carbon atoms of the linear or branched alkyl group as $Ra^{02}$ and $Ra^{03}$ is preferably 2 to 6 and more preferably 2 to 4.

Among the above, the constitutional unit (a01) is more preferably a constitutional unit represented by General Formula (a01-1).

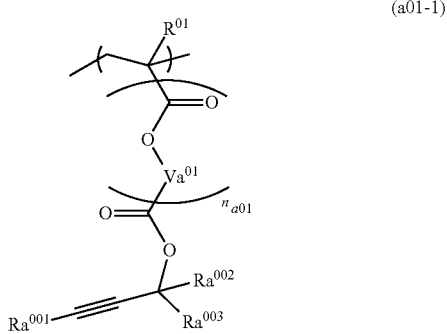

(a01-1)

[In the formula, $R^{01}$ represents a hydrogen atom, an alkyl group having 1 to 5 carbon atoms, or a halogenated alkyl group having 1 to 5 carbon atoms. $Va^{01}$ represents a divalent linking group. $n_{a01}$ represents an integer in a range of 0 to 2. $Ra^{001}$ to $Ra^{003}$ each independently represent a linear or branched alkyl group.

In General Formula (a01-1), $R^{01}$ represents a hydrogen atom, an alkyl group having 1 to 5 carbon atoms, or a halogenated alkyl group having 1 to 5 carbon atoms.

The alkyl group having 1 to 5 carbon atoms as $R^{01}$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group obtained by substituting part or all of hydrogen atoms in the alkyl group having 1 to 5 carbon atoms with a halogen atom. The halogen atom is particularly preferably a fluorine atom.

$R^{01}$ is preferably a hydrogen atom, an alkyl group having 1 to 5 carbon atoms, or a fluorinated alkyl group having 1 to 5 carbon atoms, and it is most preferably a hydrogen atom or a methyl group in terms of industrial availability.

In General Formula (a01-1), $Va^{01}$ represents a divalent linking group. The divalent hydrocarbon group as $Va^{01}$ may be an aliphatic hydrocarbon group or an aromatic hydrocarbon group.

The aliphatic hydrocarbon group as the divalent hydrocarbon group represented by $Va^{01}$ may be saturated or unsaturated. In general, it is preferable that the aliphatic hydrocarbon group is saturated.

Specific examples of the aliphatic hydrocarbon group include a linear or branched aliphatic hydrocarbon group, and an aliphatic hydrocarbon group containing a ring in the structure thereof.

The linear aliphatic hydrocarbon group described above preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group described above preferably has 2 to 10 carbon atoms, more preferably 3 to 6 carbon atoms, still more preferably 3 or 4 carbon atoms, and most preferably 3 carbon atoms.

The branched aliphatic hydrocarbon group is preferably a branched alkylene group, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

Examples of the aliphatic hydrocarbon group containing a ring in the structure thereof include an alicyclic hydrocarbon group (a group obtained by removing two hydrogen atoms from an aliphatic hydrocarbon ring), a group obtained by bonding an alicyclic hydrocarbon group to the terminal of the linear or branched aliphatic hydrocarbon group, and a group obtained by interposing an alicyclic hydrocarbon group in the linear or branched aliphatic hydrocarbon group. Examples of the linear or branched aliphatic hydrocarbon group include the same one as the above-described linear aliphatic hydrocarbon group or the above-described branched aliphatic hydrocarbon group.

The alicyclic hydrocarbon group preferably has 3 to 20 carbon atoms and more preferably 3 to 12 carbon atoms.

The alicyclic hydrocarbon group may be a polycyclic group or a monocyclic group. The monocyclic alicyclic hydrocarbon group is preferably a group obtained by removing two hydrogen atoms from a monocycloalkane. The monocycloalkane preferably has 3 to 6 carbon atoms, and specific examples thereof include cyclopentane and cyclohexane. The polycyclic alicyclic hydrocarbon group is preferably a group obtained by removing two hydrogen atoms from a polycycloalkane, and the polycycloalkane is preferably a group having 7 to 12 carbon atoms. Specific examples of the polycycloalkane include adamantane, norbornane, isobornane, tricyclodecane, and tetracyclododecane.

The aromatic hydrocarbon group as the divalent hydrocarbon group represented by $Va^{01}$ is a hydrocarbon group having an aromatic ring.

The aromatic hydrocarbon group preferably has 3 to 30 carbon atoms, more preferably 5 to 30 carbon atoms, still more preferably 5 to 20 carbon atoms, particularly preferably 6 to 15 carbon atoms, and most preferably 6 to 12 carbon atoms. Here, the number of carbon atoms in a substituent is not included in the number of carbon atoms.

Specific examples of the aromatic ring contained in the aromatic hydrocarbon group include aromatic hydrocarbon rings such as benzene, biphenyl, fluorene, naphthalene, anthracene, and phenanthrene; and an aromatic heterocyclic ring obtained by substituting part of carbon atoms constituting the above-described aromatic hydrocarbon rings with a hetero atom. Examples of the hetero atom in the aromatic heterocyclic rings include an oxygen atom, a sulfur atom, and a nitrogen atom.

Specific examples of the aromatic hydrocarbon group include a group obtained by removing two hydrogen atoms from the above-described aromatic hydrocarbon ring (an arylene group); and a group (for example, a group obtained by removing one hydrogen atom from an aryl group in arylalkyl groups such as a benzyl group, a phenethyl group, a 1-naphthylmethyl group, a 2-naphthylmethyl group, a 1-naphthylethyl group, or a 2-naphthylethyl group) obtained by substituting one hydrogen atom of a group (an aryl group), in which one hydrogen atom has been removed from the aromatic hydrocarbon ring, with an alkylene group. The alkylene group (an alkyl chain in the arylalkyl group) preferably has 1 to 4 carbon atoms, more preferably 1 or 2 carbon atoms, and particularly preferably 1 carbon atom.

In General Formula (a01-1), $n_{a01}$ represents an integer in a range of 0 to 2, preferably 0 or 1, and more preferably 0.

In General Formula (a01-1), $Ra^{001}$ to $Ra^{003}$ each independently represent a linear or branched alkyl group. Examples of the linear or branched alkyl group as $Ra^{001}$ to $Ra^{003}$ include the same one as the linear branched alkyl group as $Ra^{01}$ in General Formula (a0-1).

Among the above, $Ra^{001}$ in General Formula (a01-1) is preferably a linear or branched alkyl group having 1 to 5 carbon atoms and more preferably a linear or branched alkyl group having 1 to 3 carbon atoms.

Among the above, $Ra^{002}$ and $Ra^{003}$ in General Formula (a01-1) are each independently preferably a linear or branched alkyl group having 1 to 5 carbon atoms and more preferably a linear or branched alkyl group having 1 to 3 carbon atoms. The total number of carbon atoms of the linear or branched alkyl group as $Ra^{002}$ and $Ra^{003}$ is preferably in a range of 2 to 6 and more preferably in a range of 2 to 4.

Specific examples of the constitutional unit (a01) are shown below. In each of the formulae shown below, $R^{\alpha}$ represents a hydrogen atom, a methyl group, or a trifluoromethyl group.

(a01-1a-1)

(a01-1a-2)

(a01-1a-3)

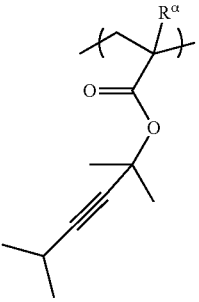

(a01-1a-4)

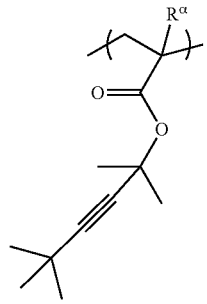

(a01-1a-5)

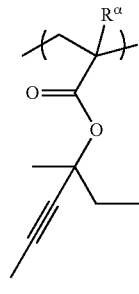

(a01-1a-6)

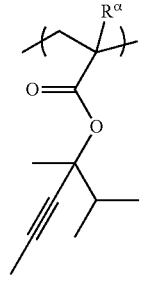

(a01-1a-7)

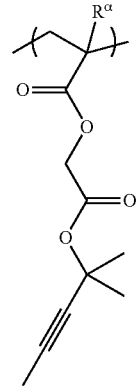

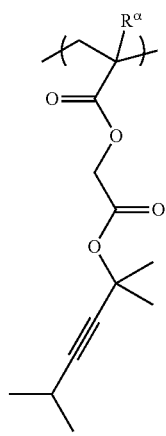 (a01-1a-8)
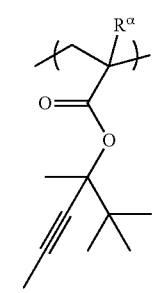 (a01-1a-9)
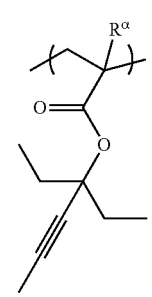 (a01-1a-10)
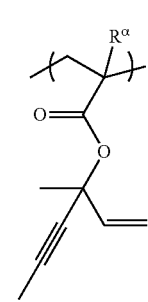 (a01-1a-11)
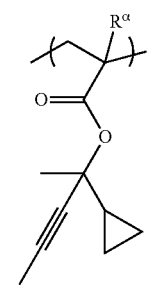 (a01-1a-12)
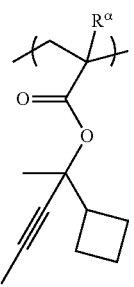 (a01-1a-13)
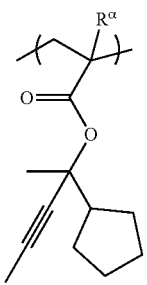 (a01-1a-14)
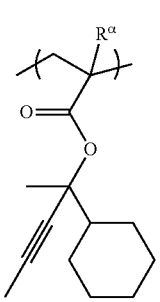 (a01-1a-15)
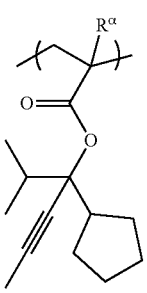 (a01-1a-16)
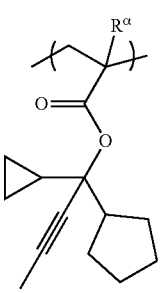 (a01-1a-17)

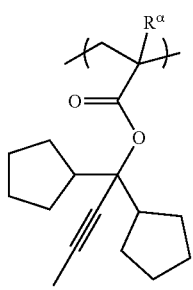 (a01-1a-18)
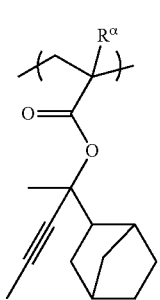 (a01-1a-19)
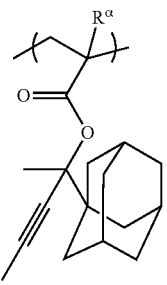 (a01-1a-20)
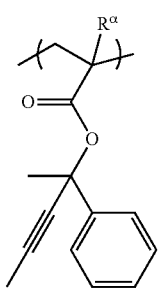 (a01-1a-21)
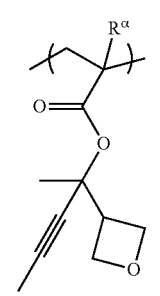 (a01-1a-22)
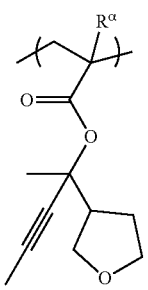 (a01-1a-23)
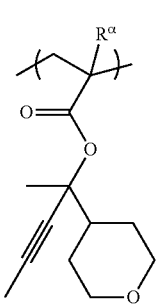 (a01-1a-24)
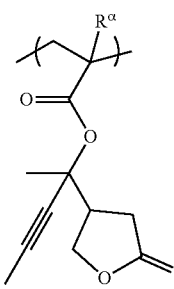 (a01-1a-25)
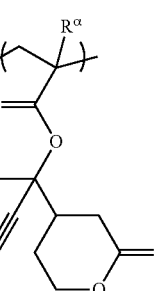 (a01-1a-26)
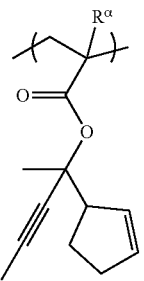 (a01-1a-27)

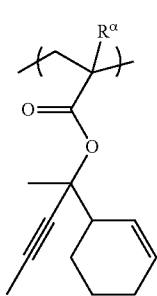

(a01-1a-28)

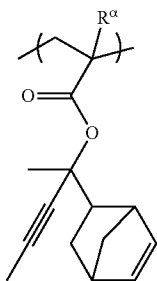

(a01-1a-29)

The constitutional unit (a01) in the resist composition according to the present embodiment is, among the above, preferably a constitutional unit represented by any of General Formula (a01-1a-1) to (a01-1a-11), more preferably a constitutional unit represented by any of General Formulae (a01-1a-1) to (a01-1a-6) and (a01-1a-9) to (a01-1a-11), and still more preferably a constitutional unit represented by any one of General Formulae (a01-1a-1) to (a01-1a-3) and (a01-1a-6).

The constitutional unit (a01) contained in the component (A1) may be one kind or may be two or more kinds.

The proportion of the constitutional unit (a01) in the component (A1) is preferably in a range of 20% to 80% by mole, more preferably in a range of 40% to 80% by mole, and still more preferably in a range of 40% to 80% by mole, with respect to the total (100% by mole) of all constitutional units constituting the component (A1).

The constitutional unit (a01) contained in the component (A1) may be one kind or may be two or more kinds.

The proportion of the constitutional unit (a01) in the component (A1) is preferably in a range of 20% to 80% by mole, and more preferably in a range of 40% to 80% by mole, with respect to the total (100% by mole) of all constitutional units constituting the component (A1).

In a case where the proportion of the constitutional unit (a01) is set equal to or larger than the lower limit value of the above preferred range, the efficiency of the deprotection reaction and the solubility of the developing solution can be appropriately ensured, and thus the effects according to the present invention can be more easily obtained. On the other hand, in a case where the proportion is equal to or smaller than the upper limit value of the above preferred range, balance with other constitutional units can be obtained, and various lithography characteristics are improved.

<<Other Constitutional Units>>

The component (A1) may have other constitutional units as necessary in addition to the constitutional unit (a01).

Examples of the other constitutional units include a constitutional unit (a1) containing an acid decomposable group having a polarity that is increased under action of acid (provided that a constitutional unit corresponding to the constitutional unit (a01) is excluded); a constitutional unit (a10) represented by General Formula (a10-1) described later; a constitutional unit (a8) derived from a compound represented by General Formula (a8-1) described later; a constitutional unit (a2) containing a lactone-containing cyclic group, a —$SO_2$—-containing cyclic group, or a carbonate-containing cyclic group (provided that a constitutional unit corresponding to the constitutional unit (a01) or the constitutional unit (a1) is excluded); a constitutional unit (a3) containing a polar group-containing aliphatic hydrocarbon group (provided that a constitutional unit corresponding to the constitutional unit (a01), the constitutional unit (a1), or the constitutional unit (a2) is excluded); a constitutional unit (a4) containing an acid non-dissociable aliphatic cyclic group; and a constitutional unit (st) derived from styrene or a styrene derivative.

In Regard to Constitutional Unit (a1):

The constitutional unit (a1) is a constitutional unit that contains an acid decomposable group having a polarity that is increased under action of acid.

Examples of the acid dissociable group are the same as those which have been proposed so far as acid dissociable groups for the base resin for a chemically amplified resist composition.

Specific examples of acid dissociable groups of the base resin proposed for a chemically amplified resist composition contains an "acetal-type acid dissociable group", a "tertiary alkyl ester-type acid dissociable group", and a "tertiary alkyloxycarbonyl acid dissociable group" described below.

Acetal-Type Acid Dissociable Group:

Examples of the acid dissociable group for protecting a carboxy group or a hydroxyl group as a polar group include the acid dissociable group represented by General Formula (a1-r-1) shown below (hereinafter, also referred to as an "acetal-type acid dissociable group").

(a1-r-1)

[In the formula, $Ra'^1$ to $Ra'^2$ represent hydrogen atoms or alkyl groups. $Ra'^3$ represents a hydrocarbon group, and $Ra'^3$ may be bonded to $Ra'^1$ or $Ra'^2$ to form a ring.]

In General Formula (a1-r-1), it is preferable that at least one of $Ra'^1$ and $Ra'2$ represents a hydrogen atom, and it is more preferable that both $Ra'^1$ and $Ra'^2$ represent hydrogen atoms.

In a case where $Ra'^1$ or $Ra'^2$ represents an alkyl group, examples of the alkyl group include the same one as the alkyl group mentioned as the substituent which may be bonded to the carbon atom at the α-position in the description on the α-substituted acrylic acid ester, and the alkyl group preferably has 1 to 5 carbon atoms. Specific examples thereof preferably include a linear or branched alkyl group. More specific examples thereof include a methyl group, an ethyl group, a propyl group, an isopropyl group, an n-butyl group, an isobutyl group, a tert-butyl group, a pentyl group, an isopentyl group, and a neopentyl group. Among these, a methyl group or an ethyl group is preferable, and a methyl group is particularly preferable.

In General Formula (a1-r-1), examples of the hydrocarbon group as $Ra'^3$ include a linear or branched alkyl group and a cyclic hydrocarbon group.

The linear alkyl group has preferably 1 to 5 carbon atoms, more preferably 1 to 4 carbon atoms, and still more preferably 1 or 2 carbon atoms. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The branched alkyl group has preferably 3 to 10 carbon atoms and more preferably 3 to 5 carbon atoms. Specific examples thereof include an isopropyl group, an isobutyl group, a tert-butyl group, an isopentyl group, a neopentyl group a 1,1-diethylpropyl group, and a 2,2-dimethylbutyl group. Among these, an isopropyl group is preferable.

In a case where $Ra'^3$ represents a cyclic hydrocarbon group, the cyclic hydrocarbon group may be an aliphatic hydrocarbon group or an aromatic hydrocarbon group and may be a polycyclic group or a monocyclic group.

The aliphatic hydrocarbon group which is a monocyclic group is preferably a group obtained by removing one hydrogen atom from a monocycloalkane. The monocycloalkane preferably has 3 to 6 carbon atoms, and specific examples thereof include cyclopentane and cyclohexane.

The aliphatic hydrocarbon group which is a polycyclic group is preferably a group obtained by removing one hydrogen atom from a polycycloalkane, where the polycycloalkane preferably has 7 to 12 carbon atoms. Specific examples thereof include adamantane, norbornane, isobornane, tricyclodecane, and tetracyclododecane.

In a case where the cyclic hydrocarbon group as $Ra'^3$ is an aromatic hydrocarbon group, the aromatic hydrocarbon group is a hydrocarbon group having at least one aromatic ring.

The aromatic ring is not particularly limited as long as it is a cyclic conjugated system having $(4n+2)\pi$ electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms.

Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group as $Ra'^3$ include a group obtained by removing one hydrogen atom from the above-described aromatic hydrocarbon ring or aromatic heterocyclic ring (an aryl group or a heteroaryl group); a group obtained by removing one hydrogen atom from an aromatic compound having two or more aromatic rings (for example, biphenyl or fluorene); and a group (for example, an arylalkyl group such as a benzyl group, a phenethyl group, a 1-naphthylmethyl group, a 2-naphthylmethyl group, a 1-naphthylethyl group, or a 2-naphthylethyl group) obtained by substituting one hydrogen atom of the above-described aromatic hydrocarbon ring or aromatic heterocyclic ring with an alkylene group. The alkylene group bonded to the aromatic hydrocarbon ring or aromatic heterocyclic ring preferably has 1 to 4 carbon atoms, more preferably 1 or 2 carbon atoms, and particularly preferably 1 carbon atom.

The cyclic hydrocarbon group as $Ra'^3$ may have a substituent. Examples of this substituent include the same one as $Ra^{x5}$ described above.

In a case where $R'^3$ is bonded to $R'^1$ or $R'^2$ to form a ring, the cyclic group is preferably a 4-membered to 7-membered ring, and more preferably a 4-membered to 6-membered ring. Specific examples of the cyclic group include a tetrahydropyranyl group and a tetrahydrofuranyl group.

Tertiary Alkyl Ester-Type Acid Dissociable Group:

Among the above polar groups, examples of the acid dissociable group for protecting the carboxy group include the acid dissociable group represented by General Formula (a1-r-2) shown below.

Among the acid dissociable groups represented by General Formula (a1-r-2), for convenience, a group which is constituted of alkyl groups is referred to as a "tertiary alkyl ester-type acid dissociable group".

(a1-r-2)

[In the formula, $R'^4$ to $R'^6$ each represents a hydrocarbon group, and $R'^5$ and $R'^6$ may be bonded to each other to form a ring.]

Examples of the hydrocarbon group as $R'^4$ include a linear or branched alkyl group, a linear or cyclic alkenyl group, and a cyclic hydrocarbon group.

Examples of the linear or branched alkyl group and the cyclic hydrocarbon group (the aliphatic hydrocarbon group which is a monocyclic group, the aliphatic hydrocarbon group which is a polycyclic group, or the aromatic hydrocarbon group), as $R'^4$, include the same one as $Ra'^3$ described above.

The chain or cyclic alkenyl group as $R'^4$ is preferably an alkenyl group having 2 to 10 carbon atoms.

Examples of the hydrocarbon group as $R'^5$ or $R'^6$ include the same one as $R'^3$ described above.

In a case where $R'^5$ to $R'^6$ are bonded to each other to form a ring, suitable examples thereof include groups represented by General Formula (a1-r2-1), General Formula (a1-r2-2), and General Formula (a1-r2-3).

On the other hand, in a case where $R'^4$ to $R'^6$ are not bonded to each other and represent an independent hydrocarbon group, suitable examples thereof include a group represented by General Formula (a1-r2-4).

(a1-r2-1)

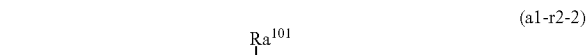

(a1-r2-2)

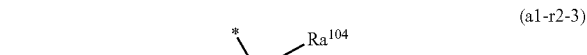

(a1-r2-3)

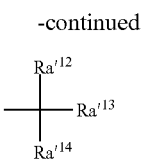

(a1-r2-4)

[In General Formula (a1-r2-1), $Ra'^{10}$ represents a linear or branched alkyl group having 1 to 12 carbon atoms, part of which may be substituted with a halogen atom or a hetero atom-containing group. $R'^{11}$ represents a group that forms an aliphatic cyclic group together with a carbon atom to which $R'^{10}$ is bonded. In General Formula (a1-r2-2), Ya represents a carbon atom. Xa is a group that forms a cyclic hydrocarbon group together with Ya. Part or all of hydrogen atoms contained in the cyclic hydrocarbon group may be substituted. $Ra^{101}$ to $Ra^{103}$ each independently represent a hydrogen atom, a monovalent chain saturated hydrocarbon group having 1 to 10 carbon atoms, or a monovalent aliphatic cyclic saturated hydrocarbon group having 3 to 20 carbon atoms. Part or all of hydrogen atoms contained in the chain saturated hydrocarbon group and the aliphatic cyclic saturated hydrocarbon group may be substituted. Two or more of $Ra^{101}$ to $Ra^{103}$ may be bonded to each other to form a ring structure. In General Formula (a1-r2-3), Yaa represents a carbon atom. Xaa is a group that forms an aliphatic cyclic group together with Yaa. $Ra^{104}$ represents an aromatic hydrocarbon group which may have a substituent. In General Formula (a1-r2-4), $R'^{12}$ and $R'^{13}$ each independently represent a monovalent chain saturated hydrocarbon group having 1 to 10 carbon atoms or a hydrogen atom. Part or all of hydrogen atoms contained in the chain saturated hydrocarbon group may be substituted. $Ra'^{14}$ represents a hydrocarbon group which may have a substituent. * represents a bonding site.]

In General Formula (a1-r2-1), $Ra'^{10}$ represents a linear or branched alkyl group having 1 to 12 carbon atoms, part of which may be substituted with a halogen atom or a hetero atom-containing group.

The linear alkyl group as $Ra'^{10}$ has 1 to 12 carbon atoms, and preferably has 1 to 10 carbon atoms and particularly preferably 1 to 5 carbon atoms.

Examples of the branched alkyl group as $Ra'^{10}$ include the same one as $R'^3$.

A part of the alkyl group as $Ra'^{10}$ may be substituted with a halogen atom or a hetero atom-containing group. For example, part of hydrogen atoms constituting the alkyl group may be substituted with a halogen atom or a hetero atom-containing group. Further, part of carbon atoms (such as a methylene group) constituting the alkyl group may be substituted with a hetero atom-containing group.

Examples of the hetero atom mentioned here include an oxygen atom, a sulfur atom, and a nitrogen atom. Examples of the hetero atom-containing group include (—O—), —C(=O)—O—, —O—C(=O)—, —C(=O)—, —O—C(=O)—O—, —C(=O)—NH—, —NH—, —S—, —S(=O)$_2$—, and —S(=O)$_2$—O—.

In General Formula (a1-r2-1), $R'^{11}$ (a group that forms an aliphatic cyclic group together with a carbon atom to which $R'^{10}$ is bonded) is preferably the group mentioned as the aliphatic hydrocarbon group (the alicyclic hydrocarbon group) which is a monocyclic group or a polycyclic group as $R'^3$ in General Formula (a1-r-1). Among them, a monocyclic alicyclic hydrocarbon group is preferable, specifically, a cyclopentyl group or a cyclohexyl group is more preferable, and a cyclopentyl group is still more preferable.

In General Formula (a1-r2-2), examples of the cyclic hydrocarbon group that is formed by Xa together with Ya include a group obtained by further removing one or more hydrogen atoms from a cyclic monovalent hydrocarbon group (an aliphatic hydrocarbon group) as $R'^3$ in General Formula (a1-r-1).

The cyclic hydrocarbon group that is formed by Xa together with Ya may have a substituent. Examples of this substituent include the same one as the substituent which may be contained in the cyclic hydrocarbon group as $R'^3$.

In General Formula (a1-r2-2), as $Ra^{101}$ to $Ra^{103}$, examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms, as $Ra^{101}$ to $Ra^{103}$, include monocyclic aliphatic saturated hydrocarbon groups such as a cyclopropyl group, a cyclobutyl group, a cyclopentyl group, a cyclohexyl group, a cycloheptyl group, a cyclooctyl group, a cyclodecyl group, and cyclododecyl group; and polycyclic aliphatic saturated hydrocarbon groups such as a bicyclo[2.2.2]octanyl group, a tricyclo[5.2.1.02,6]decanyl group, a tricyclo[3.3.1.13,7]decanyl group, a tetracyclo[6.2.1.13,6.02,7] dodecanyl group, and an adamantyl group.

Among them, $Ra^{101}$ to $Ra^{103}$ are preferably a hydrogen atom or a monovalent chain saturated hydrocarbon group having 1 to 10 carbon atoms, and among them, a hydrogen atom, a methyl group, and an ethyl group are more preferable, and a hydrogen atom is particularly preferable from the viewpoint of easy synthesis.

Examples of the substituent contained in the chain saturated hydrocarbon group represented by $R^{101}$ to $Ra^{103}$ or the aliphatic cyclic saturated hydrocarbon group include the same groups as $Ra^{x5}$ described above.

Examples of the group containing a carbon-carbon double bond generated by forming a ring structure, which is obtained by bonding two or more of $R^{101}$ to $Ra^{103}$ to each other, include a cyclopentenyl group, a cyclohexenyl group, a methylcyclopentenyl group, a methylcyclohexenyl group, a cyclopentylideneethenyl group, and a cyclohexylideneethenyl group. Among these, a cyclopentenyl group, a cyclohexenyl group, and a cyclopentylideneethenyl group are preferable from the viewpoint of easy synthesis.

In General Formula (a1-r2-3), an aliphatic cyclic group that is formed by Xaa together with Yaa is preferably the group mentioned as the aliphatic hydrocarbon group which is a monocyclic group or a polycyclic group as $R'^3$ in General Formula (a1-r-1).

In General Formula (a1-r2-3), examples of the aromatic hydrocarbon group as $Ra^{104}$ include a group obtained by removing one or more hydrogen atoms from an aromatic hydrocarbon ring having 5 to 30 carbon atoms. Among them, $Ra^{104}$ is preferably a group obtained by removing one or more hydrogen atoms from an aromatic hydrocarbon ring having 6 to 15 carbon atoms, more preferably a group obtained by removing one or more hydrogen atoms from benzene, naphthalene, anthracene, or phenanthrene, still more preferably a group obtained by removing one or more hydrogen atoms from benzene, naphthalene, or anthracene, particularly preferably a group obtained by removing one or more hydrogen atoms from benzene or naphthalene, and most preferably a group obtained by removing one or more hydrogen atoms from benzene.

Examples of the substituent which may be contained in $Ra^{104}$ in General Formula (a1-r2-3) include a methyl group, an ethyl group, propyl group, a hydroxy group, a carboxy group, a halogen atom, an alkoxy group (a methoxy group, an ethoxy group, a propoxy group, a butoxy group, and the like), and an alkyloxycarbonyl group.

In General Formula (a1-r2-4), $R'^{12}$ and $R'^{13}$ each independently represent a monovalent chain saturated hydrocarbon group having 1 to 10 carbon atoms or a hydrogen atom. Examples of the monovalent chain saturated hydrocarbon group having 1 to 10 carbon atoms as $Ra'^{12}$ and $R'^{13}$ include the same one as the monovalent chain saturated hydrocarbon group having 1 to 10 carbon atoms as $R^{101}$ to $Ra^{103}$ as described above. Part or all of hydrogen atoms contained in the chain saturated hydrocarbon group may be substituted.

Among them, $Ra'^{12}$ and $R'^{13}$ are preferably a hydrogen atom or an alkyl group having 1 to 5 carbon atoms, more preferably an alkyl group having 1 to 5 carbon atoms, still more preferably a methyl group or an ethyl group, and particularly preferably a methyl group.

In a case where the chain saturated hydrocarbon groups represented by $R'^{12}$ and $R'^{13}$ are substituted, examples of the substituent include the same group as $Ra^{x5}$ described above.

In General Formula (a1-r2-4), $Ra'^{14}$ represents a hydrocarbon group which may have a substituent. Examples of the hydrocarbon group as $R'^{14}$ include a linear or branched alkyl group and a cyclic hydrocarbon group.

The linear alkyl group as $Ra'^{14}$ has preferably 1 to 5 carbon atoms, more preferably 1 to 4 carbon atoms, and still more preferably 1 or 2 carbon atoms. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The branched alkyl group as $R'^{14}$ has preferably 3 to 10 carbon atoms and more preferably 3 to 5 carbon atoms. Specific examples thereof include an isopropyl group, an isobutyl group, a tert-butyl group, an isopentyl group, a neopentyl group a 1,1-diethylpropyl group, and a 2,2-dimethylbutyl group. Among these, an isopropyl group is preferable.

In a case where $R'^{14}$ represents a cyclic hydrocarbon group, the cyclic hydrocarbon group may be an aliphatic hydrocarbon group or an aromatic hydrocarbon group and may be a polycyclic group or a monocyclic group.

The aliphatic hydrocarbon group which is a monocyclic group is preferably a group obtained by removing one hydrogen atom from a monocycloalkane. The monocycloalkane preferably has 3 to 6 carbon atoms, and specific examples thereof include cyclopentane and cyclohexane.

The aliphatic hydrocarbon group which is a polycyclic group is preferably a group obtained by removing one hydrogen atom from a polycycloalkane, where the polycycloalkane preferably has 7 to 12 carbon atoms. Specific examples thereof include adamantane, norbornane, isobornane, tricyclodecane, and tetracyclododecane.

Examples of the aromatic hydrocarbon group as $Ra'^{14}$ include the same one as the aromatic hydrocarbon group as $Ra^{104}$. Among them, $R'^{14}$ is preferably a group obtained by removing one or more hydrogen atoms from an aromatic hydrocarbon ring having 6 to 15 carbon atoms, more preferably a group obtained by removing one or more hydrogen atoms from benzene, naphthalene, anthracene, or phenanthrene, still more preferably a group obtained by removing one or more hydrogen atoms from benzene, naphthalene, or anthracene, particularly preferably a group obtained by removing one or more hydrogen atoms from naphthalene or anthracene, and most preferably a group obtained by removing one or more hydrogen atoms from naphthalene.

Examples of the substituent which may be contained in $Ra'^{14}$ include the same one as the substituent which may be contained in $Ra^{104}$.

In a case where $Ra'^{14}$ in General Formula (a1-r2-4) is a naphthyl group, the position at which the tertiary carbon atom in General Formula (a1-r2-4) is bonded is any of the 1-position and the 2-position of the naphthyl group.

In a case where $Ra'^{14}$ in General Formula (a1-r2-4) is an anthryl group, the position at which the tertiary carbon atom in General Formula (a1-r2-4) is bonded is any of the 1-position, the 2-position, and 9-position of the anthryl group.

Specific examples of the group represented by General Formula (a1-r2-1) are shown below.

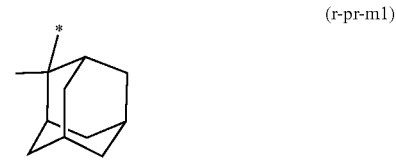

(r-pr-m1)

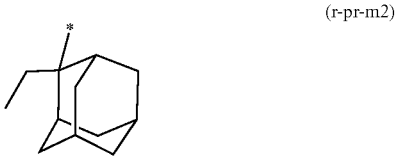

(r-pr-m2)

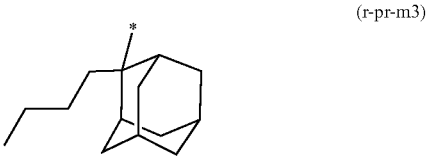

(r-pr-m3)

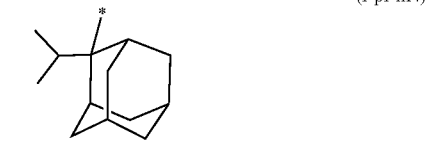

(r-pr-m4)

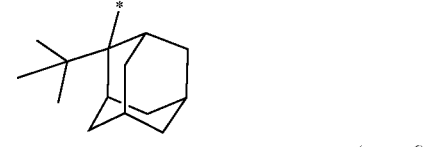

(r-pr-m5)

(r-pr-m6)

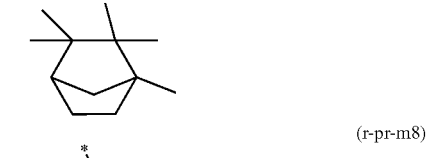

(r-pr-m7)

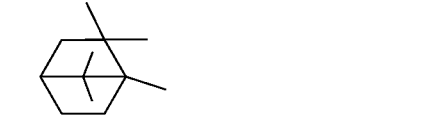

(r-pr-m8)

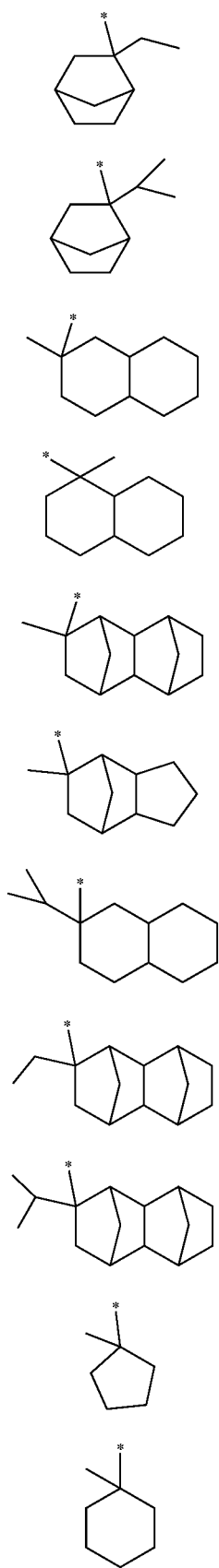
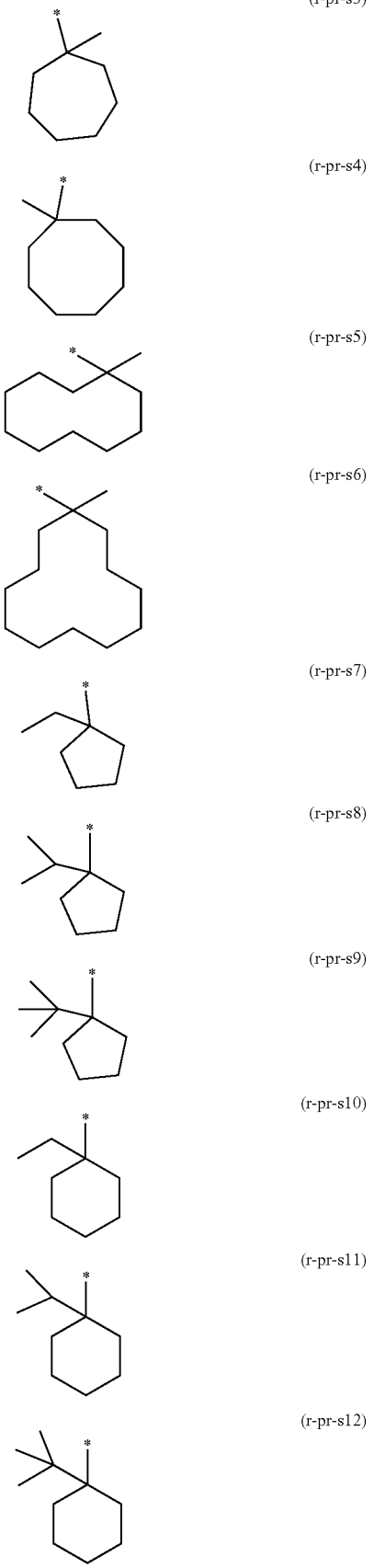

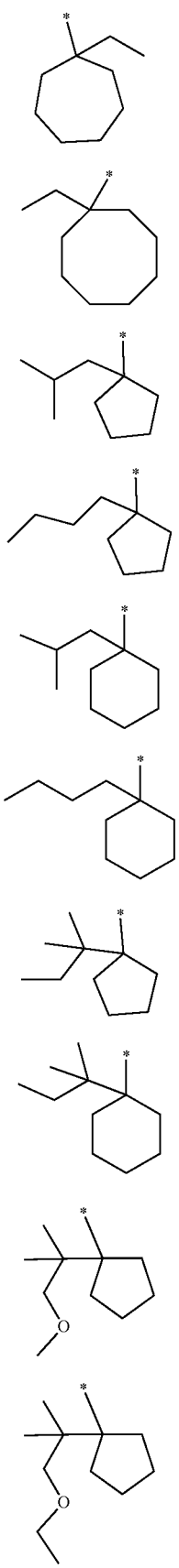
(r-pr-s13)
(r-pr-s14)
(r-pr-s15)
(r-pr-s16)
(r-pr-s17)
(r-pr-s18)
(r-pr-s19)
(r-pr-s20)
(r-pr-sp1)
(r-pr-sp2)
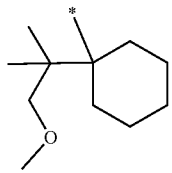
(r-pr-sp3)
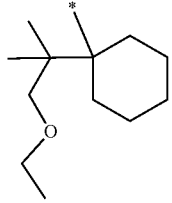
(r-pr-sp4)
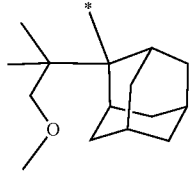
(r-pr-mp1)
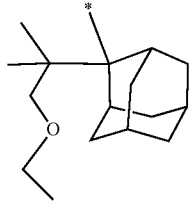
(r-pr-mp2)
Specific examples of the group represented by General Formula (a1-r2-2) are shown below.
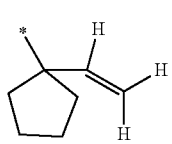
(r-pr-sv1)
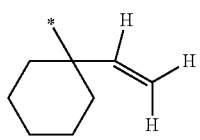
(r-pr-sv2)
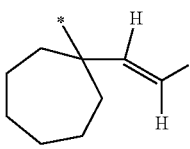
(r-pr-sv3)
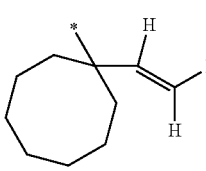
(r-pr-sv4)

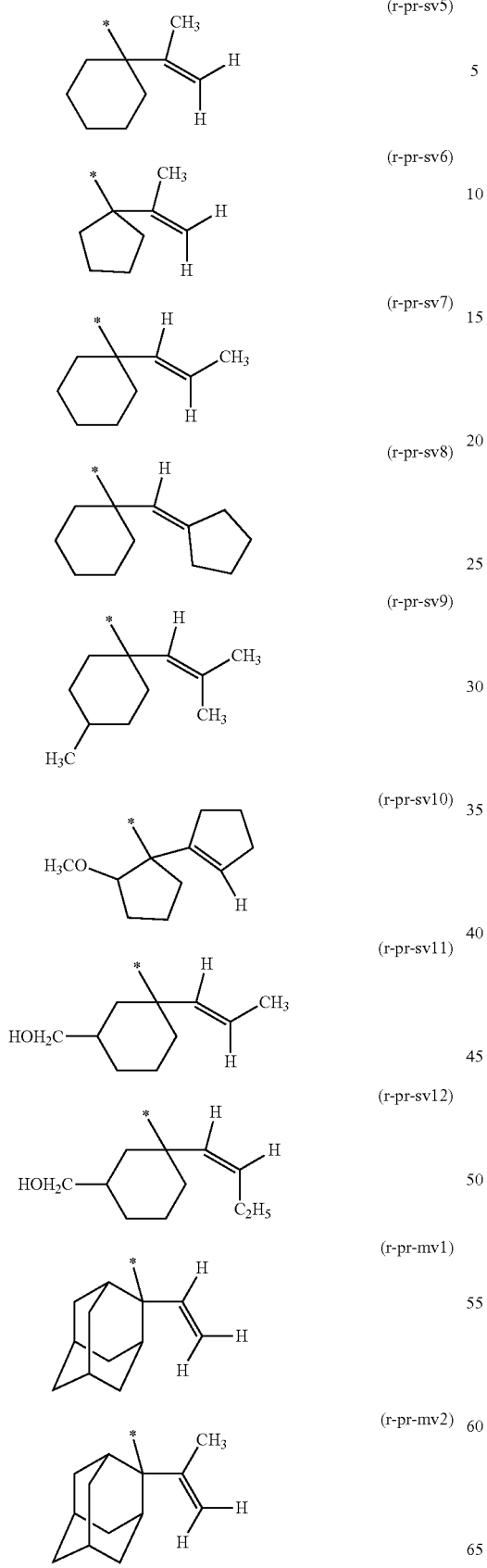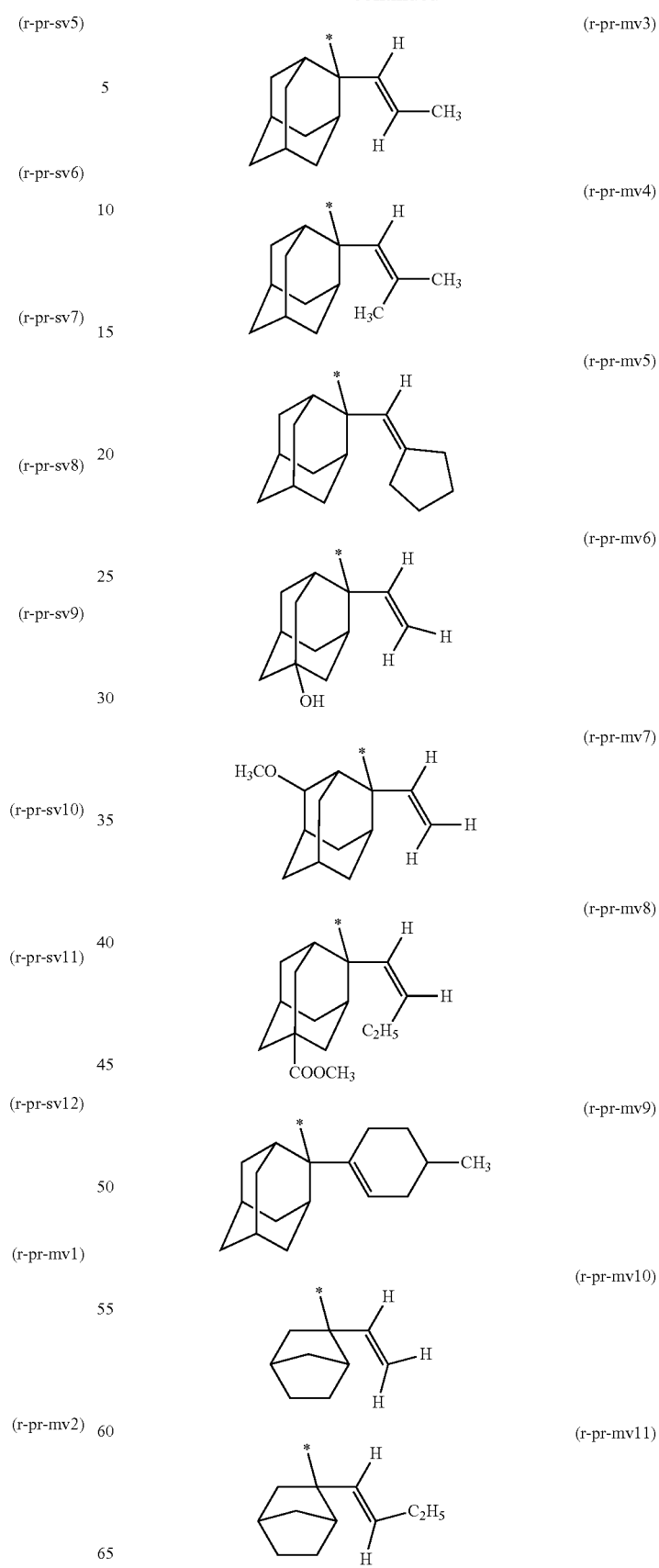

(r-pr-mv12) 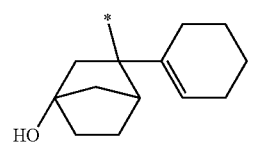
(r-pr-mv13) 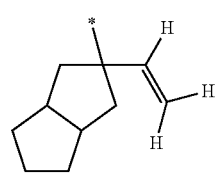
(r-pr-mv14) 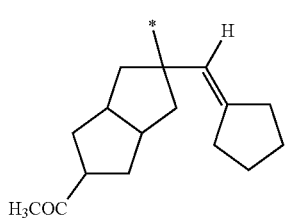
(r-pr-mv15) 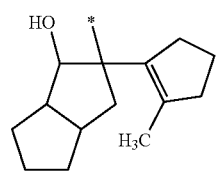
(r-pr-mv16) 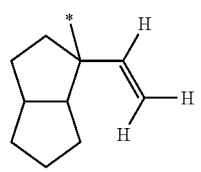
(r-pr-mv17) 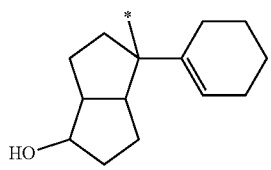
(r-pr-mv18) 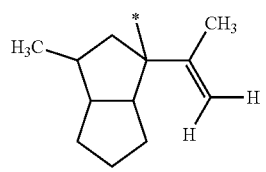
(r-pr-mv19) 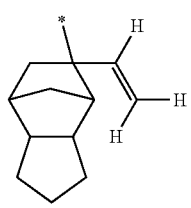
(r-pr-mv20) 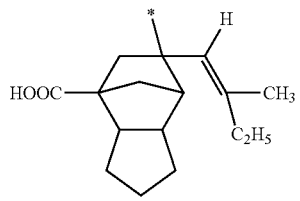
(r-pr-mv21) 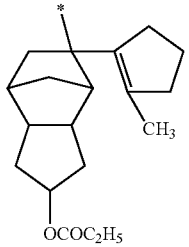
Specific examples of the group represented by General Formula (a1-r2-3) are shown below.
(r-pr-sa1) 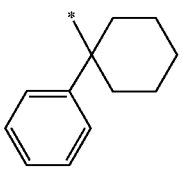
(r-pr-sa2) 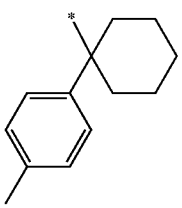
(r-pr-sa3) 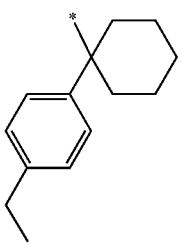
(r-pr-sa4) 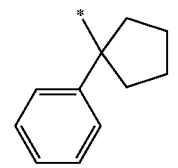
(r-pr-sa5) 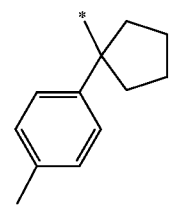

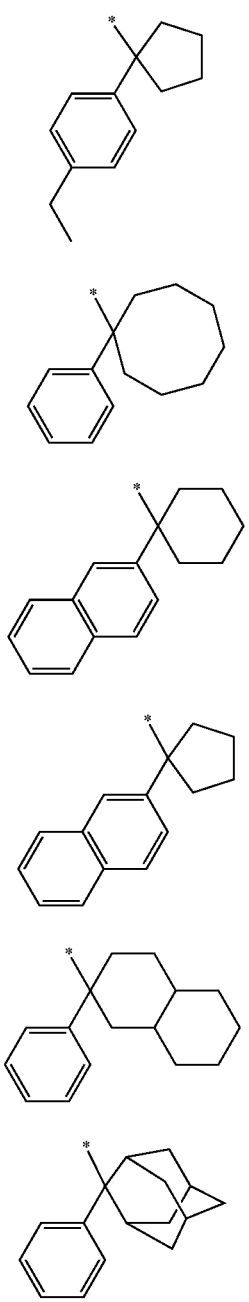
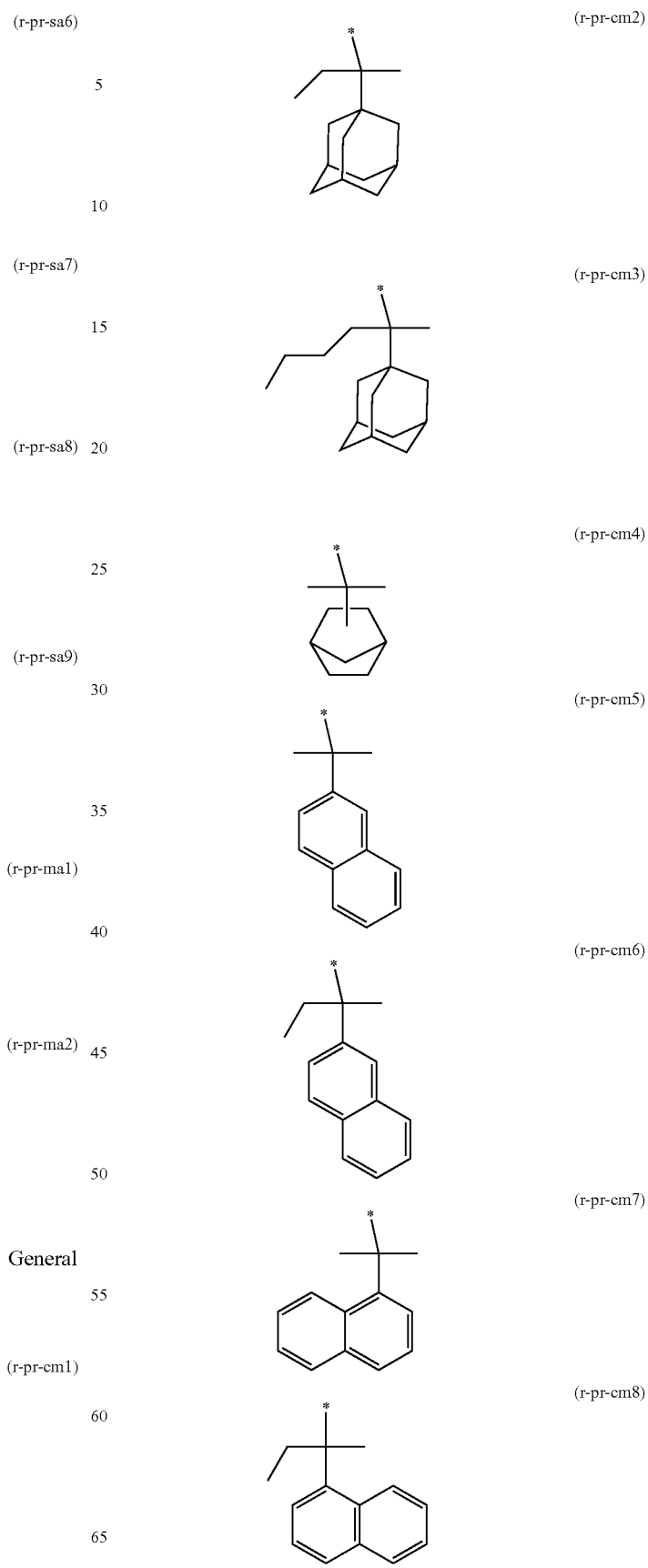
Specific examples of the group represented by General Formula (a1-r2-4) are shown below.

(r-pr-cs1)

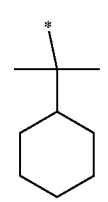

(r-pr-cs2)

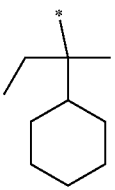

(r-pr-cs3)

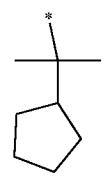

(r-pr-cs4)

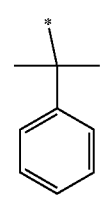

(r-pr-cs5)

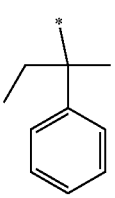

(r-pr-c1)

(r-pr-c2)

(r-pr-c3)

Tertiary Alkyloxycarbonyl Acid Dissociable Group:

Among the polar groups, examples of the acid dissociable group for protecting a hydroxyl group include an acid dissociable group (hereinafter, for convenience, also referred to as a "tertiary alkyloxycarbonyl acid dissociable group") represented by General Formula (a1-r-3) shown below.

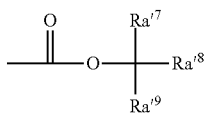

(a1-r-3)

[In the formula, $R'^7$ to $R'^9$ each represent an alkyl group.]

In General Formula (a1-r-3), $R'^7$ to $R'^9$ are each preferably an alkyl group having 1 to 5 carbon atoms and more preferably an alkyl group having 1 to 3 carbon atoms.

Further, the total number of carbon atoms in each of the alkyl groups is preferably in a range of 3 to 7, more preferably in a range of 3 to 5, and most preferably 3 or 4.

Examples of the constitutional unit (a1) include a constitutional unit derived from acrylic acid ester in which the hydrogen atom bonded to the carbon atom at the α-position may be substituted with a substituent; a constitutional unit derived from acrylamide; a constitutional unit in which at least part of hydrogen atoms in a hydroxyl group of a constitutional unit derived from hydroxystyrene or a hydroxystyrene derivative are protected by the substituent including an acid decomposable group; and a constitutional unit in which at least part of hydrogen atoms in —C(=O)—OH of a constitutional unit derived from vinylbenzoic acid or a vinylbenzoic acid derivative are protected by the substituent including an acid decomposable group.

Among the above, the constitutional unit (a1) is preferably a constitutional unit derived from acrylic acid ester in which the hydrogen atom bonded to the carbon atom at the α-position may be substituted with a substituent.

Preferred specific examples of such a constitutional unit (a1) include constitutional units represented by General Formula (a1-1) or (a1-2).

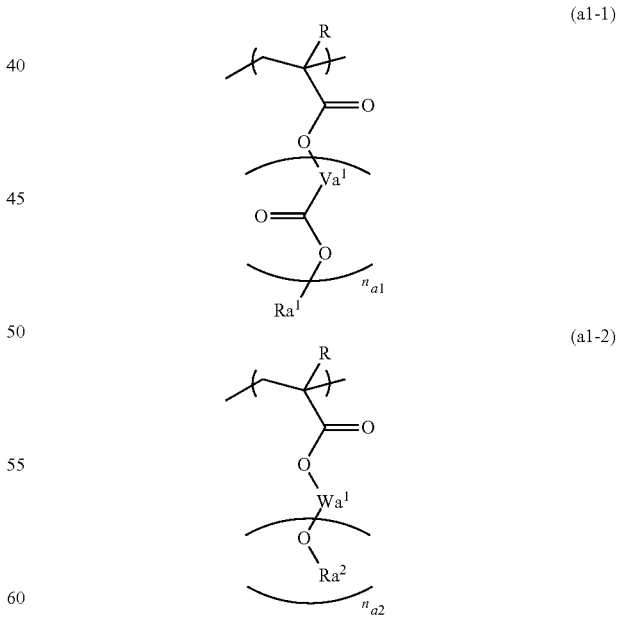

[In the formula, R represents a hydrogen atom, an alkyl group having 1 to 5 carbon atoms, or a halogenated alkyl group having 1 to 5 carbon atoms. $Va^1$ represents a divalent hydrocarbon group which may have an ether bond. $n_{a1}$ represents an integer in a range of 0 to 2. $Ra^1$ is an acid dissociable group represented by General Formula (a1-r-1) or (a1-r-2). $Wa^1$ represents an $(n_{a2}+1)$-valent hydrocarbon group, $n_{a2}$ represents an integer in a range of 1 to 3, and $Ra^2$ represents an acid dissociable group represented by General Formula (a1-r-1) or (a1-r-3).]

In General Formula (a1-1), the alkyl group having 1 to 5 carbon atoms as R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group obtained by substituting part or all of hydrogen atoms in the alkyl group having 1 to 5 carbon atoms with a halogen atom. The halogen atom is particularly preferably a fluorine atom.

R is preferably a hydrogen atom, an alkyl group having 1 to 5 carbon atoms, or a fluorinated alkyl group having 1 to 5 carbon atoms, and it is most preferably a hydrogen atom or a methyl group in terms of industrial availability.

In General Formula (a1-1), the divalent hydrocarbon group as $Va^1$ may be an aliphatic hydrocarbon group or an aromatic hydrocarbon group.

The aliphatic hydrocarbon group as the divalent hydrocarbon group represented by $Va^1$ may be saturated or unsaturated. In general, it is preferable that the aliphatic hydrocarbon group is saturated.

Specific examples of the aliphatic hydrocarbon group include a linear or branched aliphatic hydrocarbon group, and an aliphatic hydrocarbon group containing a ring in the structure thereof.

The linear aliphatic hydrocarbon group described above preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group described above preferably has 2 to 10 carbon atoms, more preferably 3 to 6 carbon atoms, still more preferably 3 or 4 carbon atoms, and most preferably 3 carbon atoms.

The branched aliphatic hydrocarbon group is preferably a branched alkylene group, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

Examples of the aliphatic hydrocarbon group containing a ring in the structure thereof include an alicyclic hydrocarbon group (a group obtained by removing two hydrogen atoms from an aliphatic hydrocarbon ring), a group obtained by bonding an alicyclic hydrocarbon group to the terminal of the linear or branched aliphatic hydrocarbon group, and a group obtained by interposing an alicyclic hydrocarbon group in the linear or branched aliphatic hydrocarbon group.

Examples of the linear or branched aliphatic hydrocarbon group include the same one as the above-described linear aliphatic hydrocarbon group or the above-described branched aliphatic hydrocarbon group.

The alicyclic hydrocarbon group preferably has 3 to 20 carbon atoms and more preferably 3 to 12 carbon atoms.

The alicyclic hydrocarbon group may be a polycyclic group or a monocyclic group. The monocyclic alicyclic hydrocarbon group is preferably a group obtained by removing two hydrogen atoms from a monocycloalkane. The monocycloalkane preferably has 3 to 6 carbon atoms, and specific examples thereof include cyclopentane and cyclohexane. The polycyclic alicyclic hydrocarbon group is preferably a group obtained by removing two hydrogen atoms from a polycycloalkane, and the polycycloalkane is preferably a group having 7 to 12 carbon atoms. Specific examples of the polycycloalkane include adamantane, norbornane, isobornane, tricyclodecane, and tetracyclododecane.

The aromatic hydrocarbon group as the divalent hydrocarbon group represented by $Va^1$ is a hydrocarbon group having an aromatic ring.

The aromatic hydrocarbon group preferably has 3 to 30 carbon atoms, more preferably 5 to 30 carbon atoms, still more preferably 5 to 20 carbon atoms, particularly preferably 6 to 15 carbon atoms, and most preferably 6 to 12 carbon atoms. Here, the number of carbon atoms in a substituent is not included in the number of carbon atoms.

Specific examples of the aromatic ring contained in the aromatic hydrocarbon group include aromatic hydrocarbon rings such as benzene, biphenyl, fluorene, naphthalene, anthracene, and phenanthrene; and an aromatic heterocyclic ring obtained by substituting part of carbon atoms constituting the above-described aromatic hydrocarbon rings with a hetero atom. Examples of the hetero atom in the aromatic heterocyclic rings include an oxygen atom, a sulfur atom, and a nitrogen atom.

Specific examples of the aromatic hydrocarbon group include a group obtained by removing two hydrogen atoms from the above-described aromatic hydrocarbon ring (an arylene group); and a group (for example, a group obtained by removing one hydrogen atom from an aryl group in arylalkyl groups such as a benzyl group, a phenethyl group, a 1-naphthylmethyl group, a 2-naphthylmethyl group, a 1-naphthylethyl group, or a 2-naphthylethyl group) obtained by substituting one hydrogen atom of a group (an aryl group), in which one hydrogen atom has been removed from the aromatic hydrocarbon ring, with an alkylene group. The alkylene group (an alkyl chain in the arylalkyl group) preferably has 1 to 4 carbon atoms, more preferably 1 or 2 carbon atoms, and particularly preferably 1 carbon atom.

In General Formula (a1-1), $Ra^1$ is an acid dissociable group represented by General Formula (a1-r-1) or (a1-r-2).

In General Formula (a1-2), the $(n_{a2}+1)$ valent hydrocarbon group as $Wa^1$ may be an aliphatic hydrocarbon group or an aromatic hydrocarbon group. The aliphatic hydrocarbon group indicates a hydrocarbon group that has no aromaticity and may be saturated or unsaturated. In general, it is preferable that the aliphatic hydrocarbon group is saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof.

The valency of $(n_{a2}+1)$ is preferably divalent, trivalent, or tetravalent, and more preferably divalent or trivalent.

In General Formula (a1-2), $Ra^2$ is an acid dissociable group represented by General Formula (a1-r-1) or (a1-r-3).
Specific examples of the constitutional unit represented by General Formula (a1-1) are shown below. In each of the formulae shown below, $R^\alpha$ represents a hydrogen atom, a methyl group, or a trifluoromethyl group.
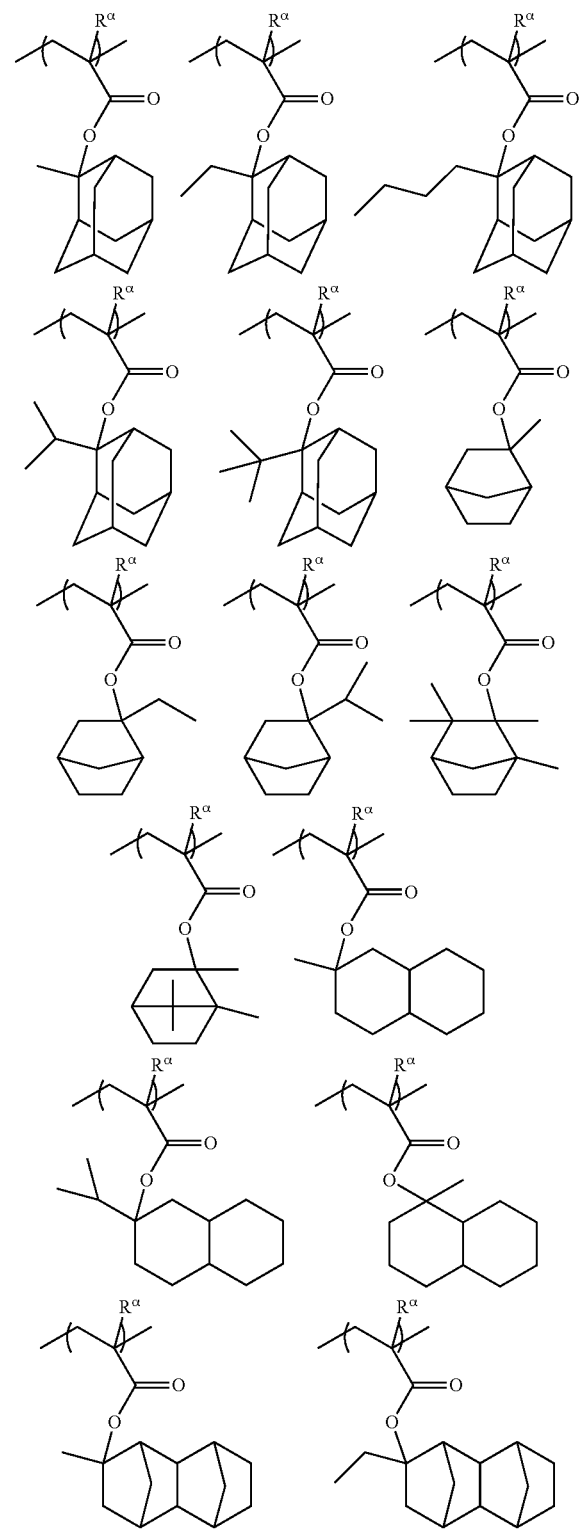
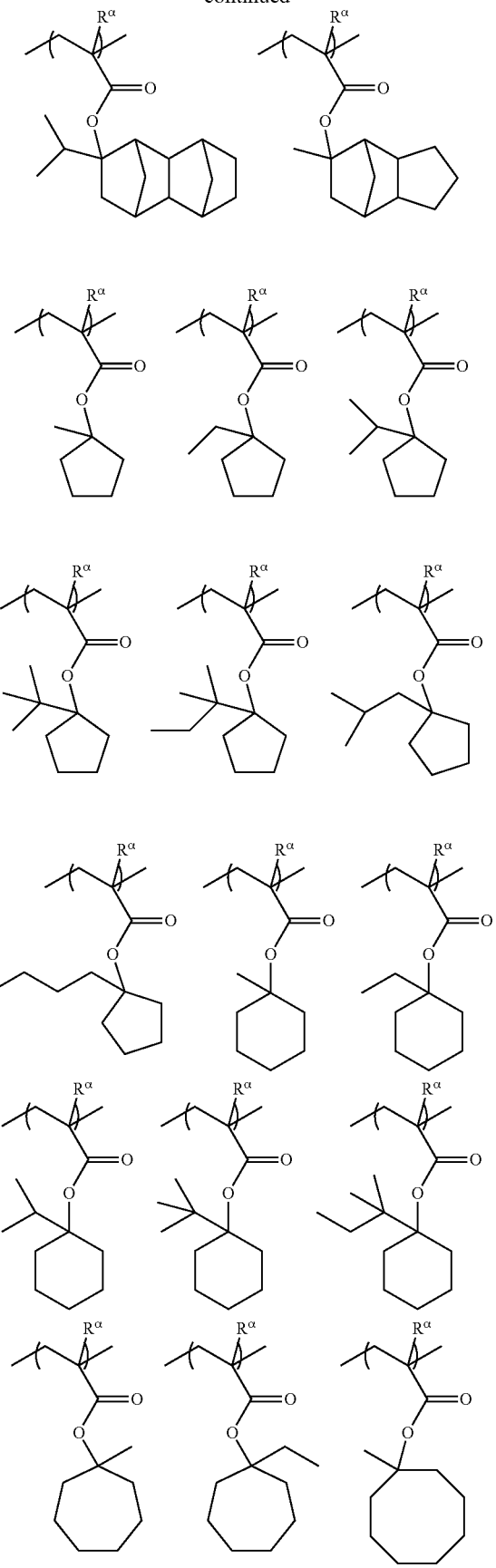

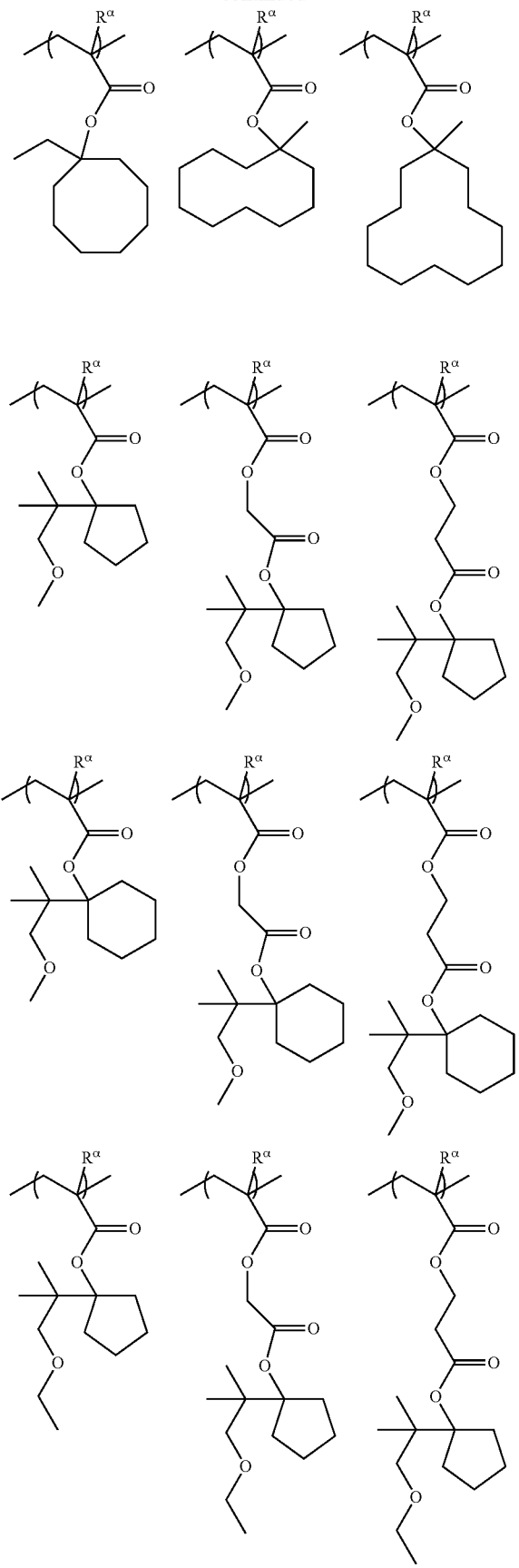
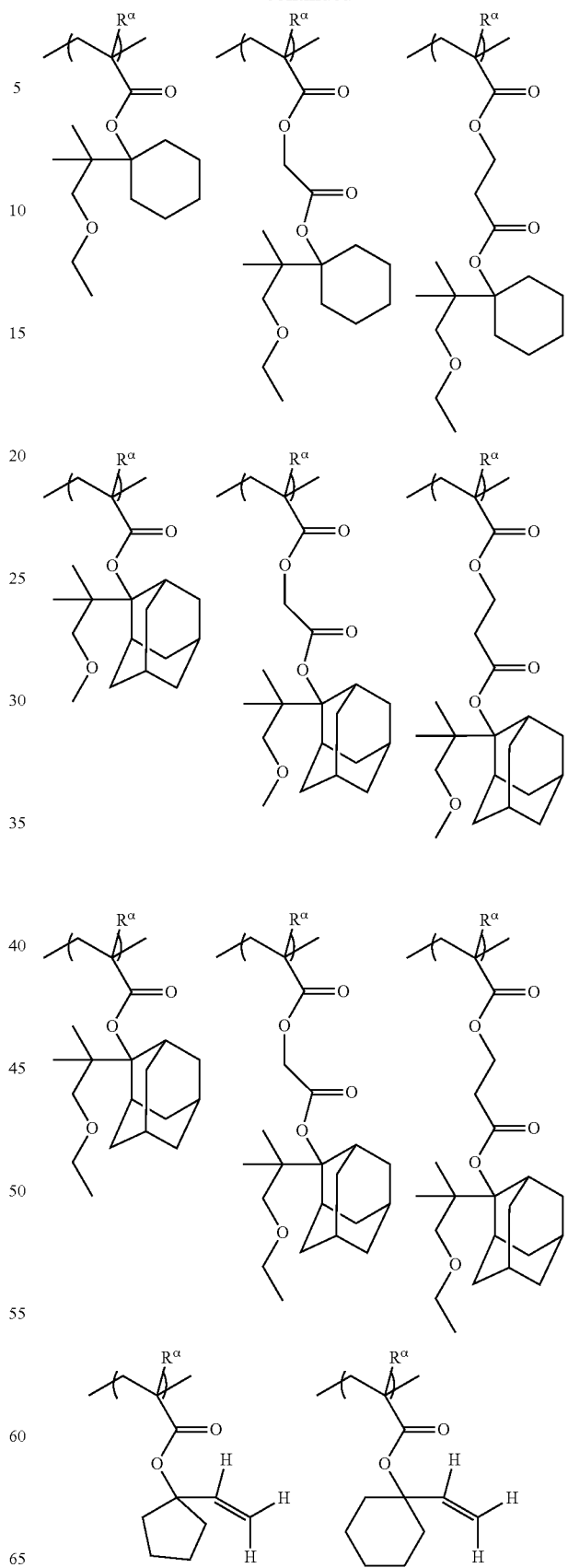

-continued
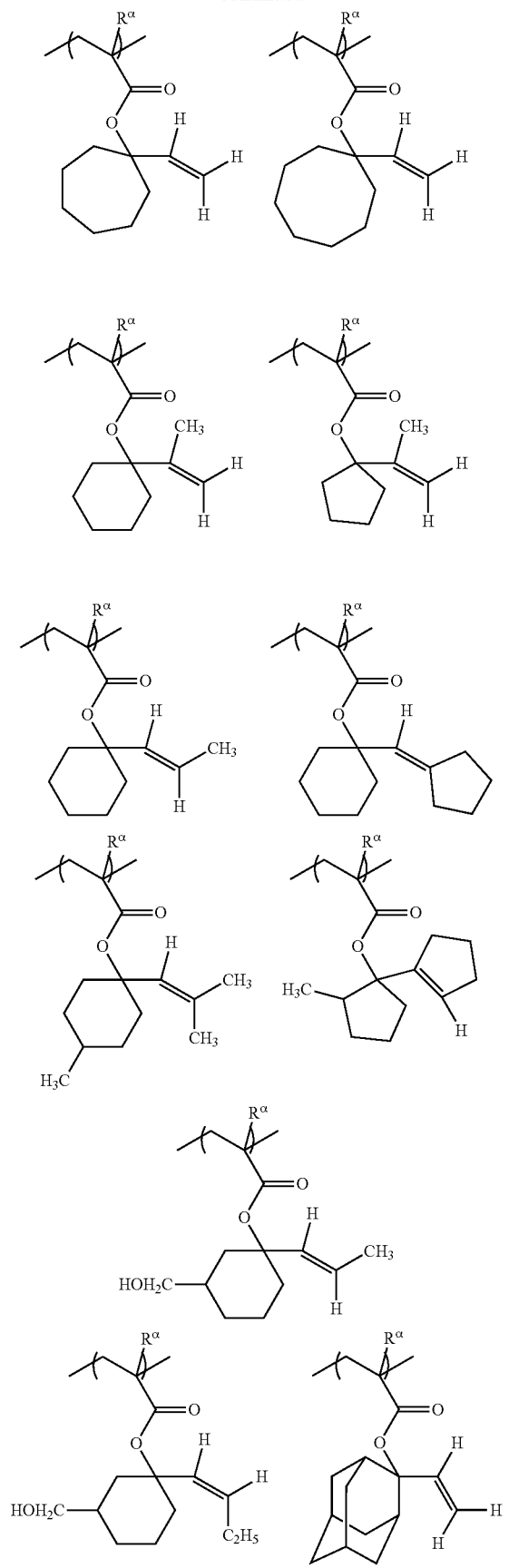
-continued
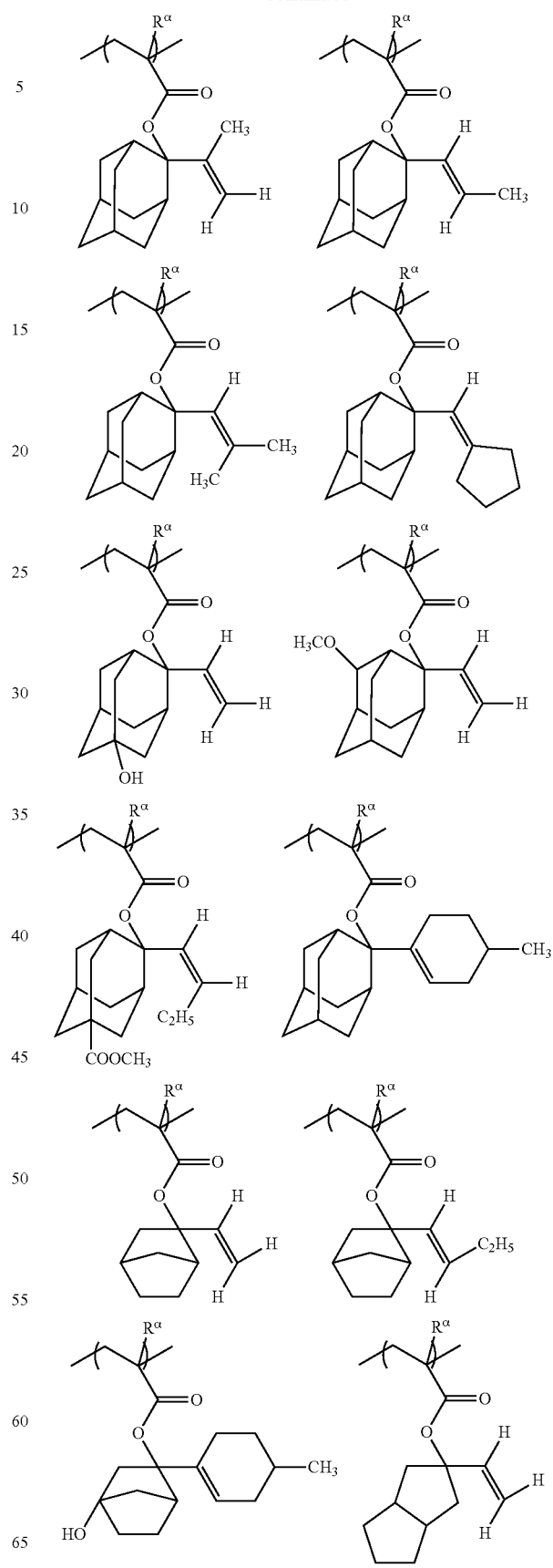

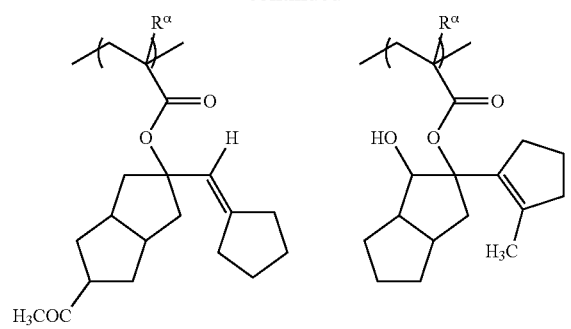
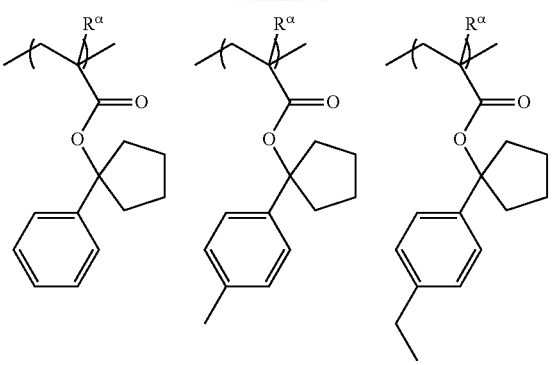
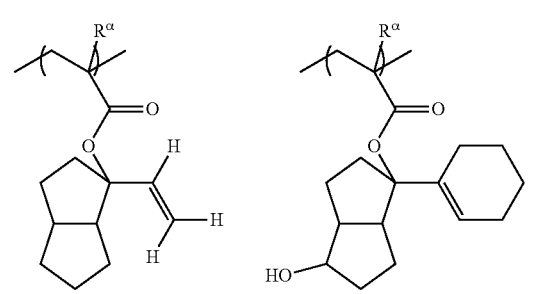
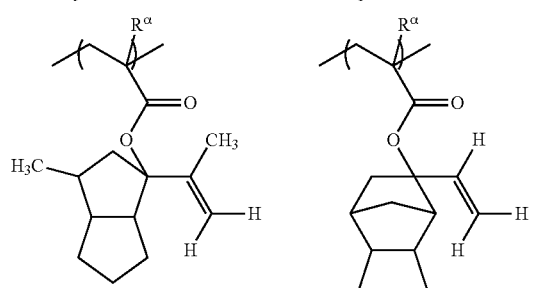
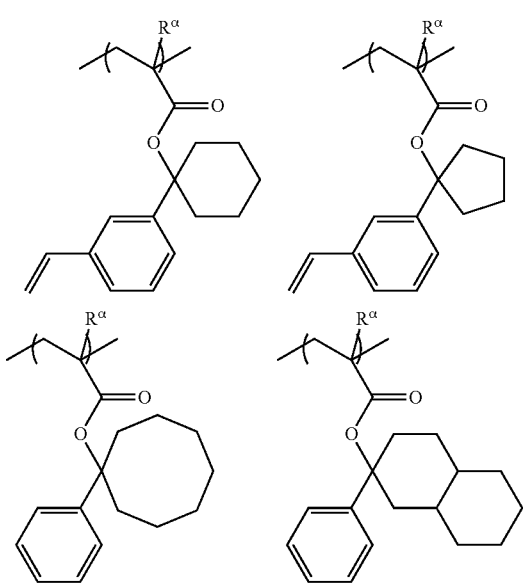
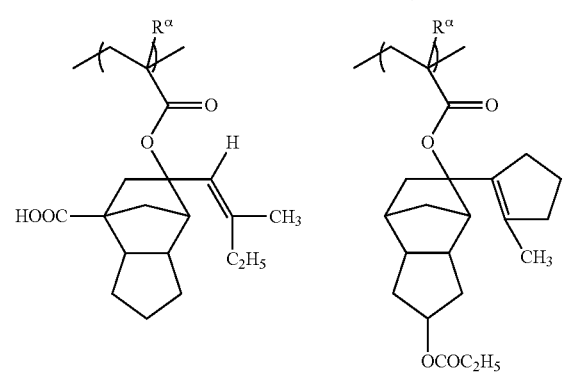
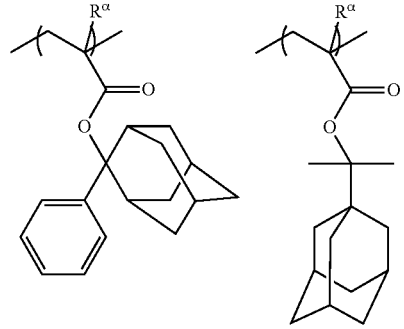
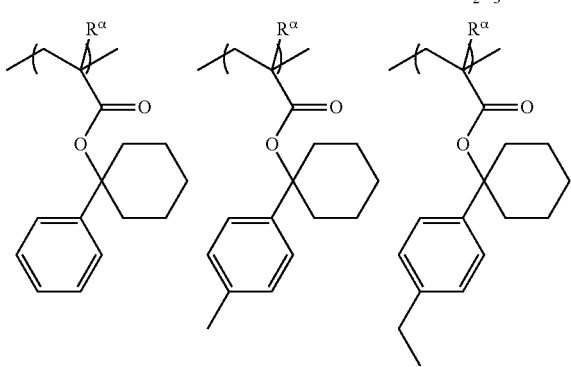

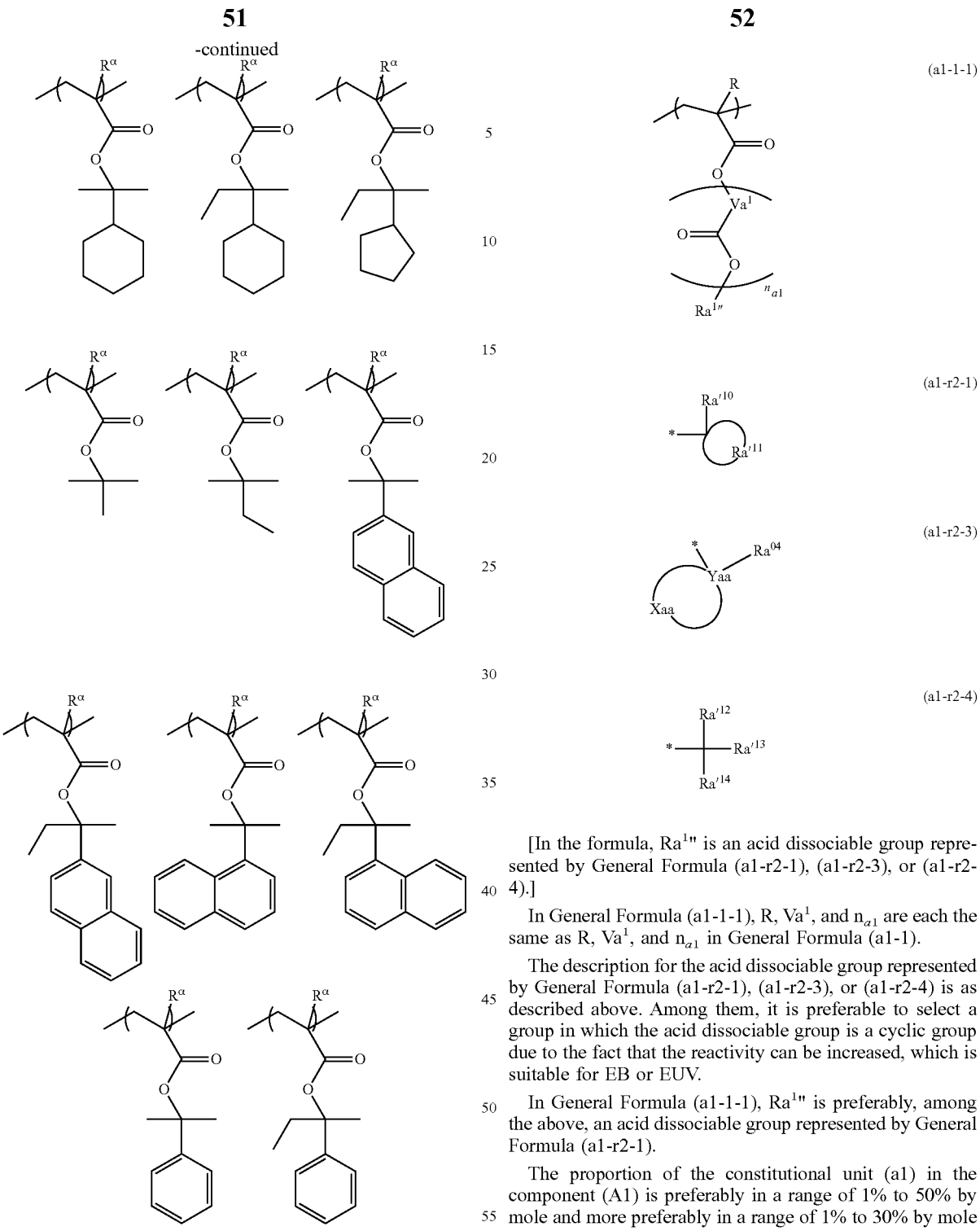

The constitutional unit (a1) contained in the component (A1) may be one kind or may be two or more kinds.

The constitutional unit (a1) is more preferably a constitutional unit represented by General Formula (a1-1) since lithography characteristics (sensitivity, shape, and the like) in lithography depending on an electron beam or EUV can be more easily increased.

Among these, the constitutional unit (a1) particularly preferably includes a constitutional unit represented by General Formula (a1-1-1) shown below.

[In the formula, $Ra^{1'''}$ is an acid dissociable group represented by General Formula (a1-r2-1), (a1-r2-3), or (a1-r2-4).]

In General Formula (a1-1-1), R, $Va^1$, and $n_{a1}$ are each the same as R, $Va^1$, and $n_{a1}$ in General Formula (a1-1).

The description for the acid dissociable group represented by General Formula (a1-r2-1), (a1-r2-3), or (a1-r2-4) is as described above. Among them, it is preferable to select a group in which the acid dissociable group is a cyclic group due to the fact that the reactivity can be increased, which is suitable for EB or EUV.

In General Formula (a1-1-1), $Ra^{1'''}$ is preferably, among the above, an acid dissociable group represented by General Formula (a1-r2-1).

The proportion of the constitutional unit (a1) in the component (A1) is preferably in a range of 1% to 50% by mole and more preferably in a range of 1% to 30% by mole with respect to the total (100% by mole) of all constitutional units constituting the component (A1).

In a case where the proportion of the constitutional unit (a1) is set within the preferred range described above, the efficiency of the deprotection reaction and the solubility of the developing solution can be appropriately ensured, and thus the effects according to the present invention can be more easily obtained.

In Regard to Constitutional Unit (a10):

The constitutional unit (a10) is a constitutional unit represented by General Formula (a10-1).

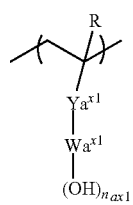

(a10-1)

[In the formula, R represents a hydrogen atom, an alkyl group having 1 to 5 carbon atoms, or a halogenated alkyl group having 1 to 5 carbon atoms. $Ya^{x1}$ represents a single bond or a divalent linking group. $Wa^{x1}$ represents an aromatic hydrocarbon group which may have a substituent. $n_{ax1}$ represents an integer of 1 or more.]

In General Formula (a10-1), R represents a hydrogen atom, an alkyl group having 1 to 5 carbon atoms, or a halogenated alkyl group having 1 to 5 carbon atoms.

The alkyl group having 1 to 5 carbon atoms as R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group.

The halogenated alkyl group having 1 to 5 carbon atoms as R is a group obtained by substituting part or all of hydrogen atoms of the above-described alkyl group having 1 to 5 carbon atoms with a halogen atom. The halogen atom is particularly preferably a fluorine atom.

R is preferably a hydrogen atom, an alkyl group having 1 to 5 carbon atoms, or a fluorinated alkyl group having 1 to 5 carbon atoms, and in terms of industrial availability, R is more preferably a hydrogen atom, a methyl group, or trifluoromethyl group, still more preferably a hydrogen atom or a methyl group, and particularly preferably a methyl group.

In General Formula (a10-1), $Ya^{x1}$ represents a single bond or a divalent linking group.

In the chemical formulae described above, the divalent linking group as $Ya^{x1}$ is not particularly limited, and suitable examples thereof include a divalent hydrocarbon group which may have a substituent and a divalent linking group having hetero atoms.

Divalent Hydrocarbon Group which May have Substituent:

In a case where $Ya^{x1}$ represents a divalent hydrocarbon group which may have a substituent, the hydrocarbon group may be an aliphatic hydrocarbon group or an aromatic hydrocarbon group.

Aliphatic Hydrocarbon Group as $Ya^{x1}$

The aliphatic hydrocarbon group indicates a hydrocarbon group that has no aromaticity. The aliphatic hydrocarbon group may be saturated or unsaturated. In general, it is preferable that the aliphatic hydrocarbon group is saturated.

Examples of the aliphatic hydrocarbon group include a linear or branched aliphatic hydrocarbon group, and an aliphatic hydrocarbon group containing a ring in the structure thereof.

Linear or Branched Aliphatic Hydrocarbon Group

The linear aliphatic hydrocarbon group described above preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group described above preferably has 2 to 10 carbon atoms, more preferably 3 to 6 carbon atoms, still more preferably 3 or 4 carbon atoms, and most preferably 3 carbon atoms.

The branched aliphatic hydrocarbon group is preferably a branched alkylene group, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

The linear or branched aliphatic hydrocarbon group may or may not have a substituent. Examples of the substituent include a fluorine atom, a fluorinated alkyl group having 1 to 5 carbon atoms, which has been substituted with a fluorine atom, and a carbonyl group.

Aliphatic Hydrocarbon Group Containing Ring in Structure Thereof

Examples of the aliphatic hydrocarbon group containing a ring in the structure thereof include a cyclic aliphatic hydrocarbon group which may have a substituent containing a hetero atom in the ring structure thereof (a group obtained by removing two hydrogen atoms from an aliphatic hydrocarbon ring), a group obtained by bonding a cyclic aliphatic hydrocarbon group to the terminal of a linear or branched aliphatic hydrocarbon group, and a group obtained by interposing a cyclic aliphatic hydrocarbon group in a linear or branched aliphatic hydrocarbon group. Examples of the linear or branched aliphatic hydrocarbon group include the same ones as those described above.

The cyclic aliphatic hydrocarbon group preferably has 3 to 20 carbon atoms and more preferably 3 to 12 carbon atoms.

The cyclic aliphatic hydrocarbon group may be a polycyclic group or a monocyclic group. The monocyclic alicyclic hydrocarbon group is preferably a group obtained by removing two hydrogen atoms from a monocycloalkane. The monocycloalkane preferably has 3 to 6 carbon atoms, and specific examples thereof include cyclopentane and cyclohexane. The polycyclic alicyclic hydrocarbon group is preferably a group obtained by removing two hydrogen atoms from a polycycloalkane, and the polycycloalkane is preferably a group having 7 to 12 carbon atoms. Specific examples thereof include adamantane, norbornane, isobornane, tricyclodecane, and tetracyclododecane.

The cyclic aliphatic hydrocarbon group may have or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and a methyl group, an ethyl group, a propyl group, an n-butyl group, or a tert-butyl group is more preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and still more preferably a methoxy group or an ethoxy group.

The halogen atom as the substituent is preferably a fluorine atom.

Examples of the halogenated alkyl group as the substituent include groups obtained by substituting part or all of hydrogen atoms in the above-described alkyl group with the above-described halogen atom.

In the cyclic aliphatic hydrocarbon group, part of carbon atoms constituting the ring structure thereof may be substituted with a substituent containing a hetero atom. The substituent containing a hetero atom is preferably —O—, —C(=O)—O—, —S—, —S(=O)$_2$—, or —S(=O)$_2$—O—.

Aromatic Hydrocarbon Group as Ya$^{x1}$

The aromatic hydrocarbon group is a hydrocarbon group having at least one aromatic ring.

The aromatic ring is not particularly limited as long as it is a cyclic conjugated system having (4n+2)π electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Here, the number of carbon atoms in a substituent is not included in the number of carbon atoms.

Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group include a group obtained by removing two hydrogen atoms from the above-described aromatic hydrocarbon ring or aromatic heterocyclic ring (an arylene group or a heteroarylene group); a group obtained by removing two hydrogen atoms from an aromatic compound having two or more aromatic rings (for example, biphenyl or fluorene); and a group (for example, a group obtained by further removing one hydrogen atom from an aryl group in an arylalkyl group such as a benzyl group, a phenethyl group, a 1-naphthylmethyl group, a 2-naphthylmethyl group, a 1-naphthylethyl group, or a 2-naphthylethyl group) obtained by substituting one hydrogen atom of a group (an aryl group or a heteroaryl group), in which one hydrogen atom has been removed from the above-described aromatic hydrocarbon ring or aromatic heterocyclic ring, with an alkylene group. The alkylene group bonded to the aryl group or the heteroaryl group preferably has 1 to 4 carbon atoms, more preferably 1 or 2 carbon atoms, and particularly preferably 1 carbon atom.

With respect to the aromatic hydrocarbon group, the hydrogen atom contained in the aromatic hydrocarbon group may be substituted with a substituent. For example, the hydrogen atom bonded to the aromatic ring in the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group having 1 to 5 carbon atoms, and a methyl group, an ethyl group, a propyl group, an n-butyl group, or a tert-butyl group is more preferable.

Examples of the alkoxy group, the halogen atom, and the halogenated alkyl group, as the substituent, include the same groups as those exemplified as the substituent that is substituted for a hydrogen atom contained in the cyclic aliphatic hydrocarbon group.

Divalent Linking Group Containing Hetero Atom:

In a case where Ya$^{x1}$ represents a divalent linking group containing a hetero atom, preferred examples of the linking group include —O—, —C(=O)—O—, —O—C(=O)—, —C(=O)—, —O—C(=O)—O—, —C(=O)—NH—, —NH—, —NH—C(=NH)— (H may be substituted with a substituent such as an alkyl group, an acyl group, or the like), —S—, —S(=O)$_2$—, —S(=O)$_2$—O—, and a group represented by General Formula —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represent a divalent hydrocarbon group which may have a substituent, O represents an oxygen atom, and m" represents an integer in a range of 0 to 3].

In a case where the divalent linking group containing a hetero atom is —C(=O)—NH—, —C(=O)—NH—C(=O)—, —NH—, or —NH—C(=NH)—, H may be substituted with a substituent such as an alkyl group, an acyl group, or the like. The substituent (an alkyl group, an acyl group, or the like) preferably has 1 to 10 carbon atoms, more preferably 1 to 8 carbon atoms, and particularly preferably 1 to 5 carbon atoms.

In General Formulae —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$—, and —Y$^{21}$—S(=O)$_2$—O—Y$^{22}$—, Y$^{21}$, and Y$^{22}$ each independently represent a divalent hydrocarbon group which may have a substituent. Examples of the divalent hydrocarbon group include the same ones as those (the divalent hydrocarbon groups which may have a substituent) described in the description of the above divalent linking group as Ya$^{x1}$.

Y$^{21}$ is preferably a linear aliphatic hydrocarbon group, more preferably a linear alkylene group, still more preferably a linear alkylene group having 1 to 5 carbon atoms, and particularly preferably a methylene group or an ethylene group.

Y$^{22}$ is preferably a linear or branched aliphatic hydrocarbon group and more preferably a methylene group, an ethylene group, or an alkylmethylene group. The alkyl group in the alkylmethylene group is preferably a linear alkyl group having 1 to 5 carbon atoms, more preferably a linear alkyl group having 1 to 3 carbon atoms, and most preferably a methyl group.

In the group represented by Formula —[Y$^{21}$—C(=O)—O]$_{m''}$—Y$^{22}$—, m" represents an integer in a range of 0 to 3, preferably an integer in a range of 0 to 2, more preferably 0 or 1, and particularly preferably 1. In other words, it is particularly preferable that the group represented by Formula —[Y$^{21}$—C(=O)—O]$_{m''}$—Y$^{22}$— represents a group represented by Formula —Y$^{21}$—C(=O)—O—Y$^{22}$—. Among these, a group represented by Formula —(CH$_2$)$_{a'}$—C(=O)≤O—(CH$_2$)$_{b'}$— is preferable. In the formula, a' represents an integer in a range of 1 to 10, preferably an integer in a range of 1 to 8, more preferably an integer in a range of 1 to 5, still more preferably 1 or 2, and most preferably 1. b' represents an integer in a range of 1 to 10, preferably an integer in a range of 1 to 8, more preferably an integer in a range of 1 to 5, still more preferably 1 or 2, and most preferably 1.

Among the above, $Ya^{x1}$ is preferably a single bond, an ester bond [—C(=O)—O—, —O—C(=O)—], an ether bond (—O—), a linear or branched alkylene group, or a combination thereof, and more preferably a single bond or an ester bond [—C(=O)—O—, —O—C(=O)—].

In General Formula (a10-1), $Wa^{x1}$ represents an aromatic hydrocarbon group which may have a substituent.

Examples of the aromatic hydrocarbon group as $Wa^{x1}$ include a group obtained by removing $(n_{ax1}+1)$ hydrogen atoms from an aromatic ring which may have a substituent. The aromatic ring is not particularly limited as long as it is a cyclic conjugated system having $(4n+2)\pi$ electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon rings with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Examples of the aromatic hydrocarbon group as $Wa^{x1}$ also include a group obtained by removing $(n_{ax1}+1)$ hydrogen atoms from an aromatic compound including an aromatic ring (for example, biphenyl or fluorene) which may have two or more substituents.

Among the above, $Wa^{x1}$ is preferably a group obtained by removing $(n_{ax1}+1)$ hydrogen atoms from benzene, naphthalene, anthracene, or biphenyl, more preferably a group obtained by removing $(n_{ax1}+1)$ hydrogen atoms from benzene or naphthalene, and still more preferably a group obtained by removing $(n_{ax1}+1)$ hydrogen atoms from benzene.

The aromatic hydrocarbon group as $Wa^{x1}$ may or may not have a substituent. Examples of the substituent include an alkyl group, an alkoxy group, a halogen atom, and a halogenated alkyl group. Examples of the alkyl group, the alkoxy group, the halogen atom, and the halogenated alkyl group, as the substituent, include the same ones as those described as the above-described substituent of the cyclic aliphatic hydrocarbon group as $Ya^{x1}$. The substituent is preferably a linear or branched alkyl group having 1 to 5 carbon atoms, more preferably a linear or branched alkyl group having 1 to 3 carbon atoms, still more preferably an ethyl group or a methyl group, and particularly preferably a methyl group. The aromatic hydrocarbon group as $Wa^{x1}$ preferably has no substituent.

In General Formula (a10-1), $n_{ax1}$ represents an integer of 1 or more, preferably an integer in a range of 1 to 10, more preferably an integer in a range of 1 to 5, still more preferably 1, 2, or 3, and particularly preferably 1 or 2.

Specific examples of the constitutional unit (a10) represented by General Formula (a10-1) are shown below.

In the formulae shown below, $R^\alpha$ represents a hydrogen atom, a methyl group, or a trifluoromethyl group.

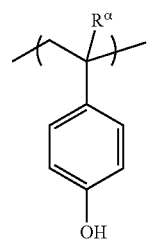

(a10-1-11)

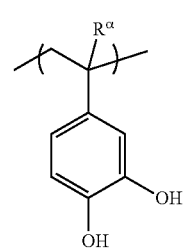

(a10-1-12)

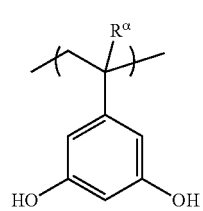

(a10-1-13)

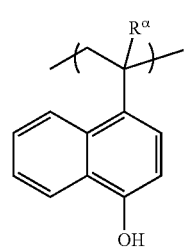

(a10-1-14)

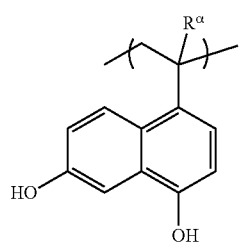

(a10-1-15)

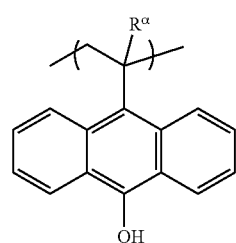

(a10-1-16)

(a10-1-17)
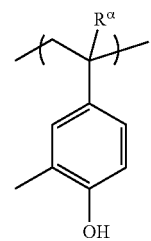
(a10-1-18)
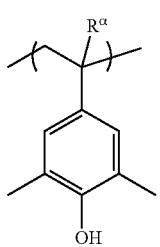
(a10-1-21)
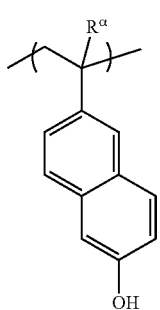
(a10-1-22)
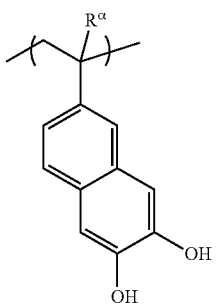
(a10-1-23)
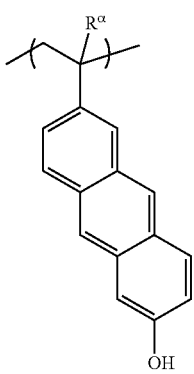
(a10-1-24)
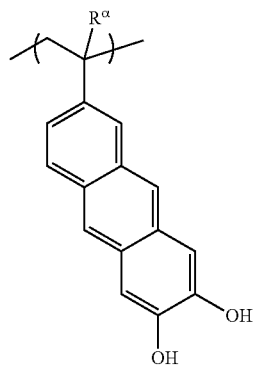
(a10-1-31)
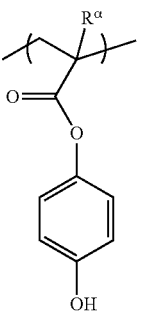
(a10-1-32)
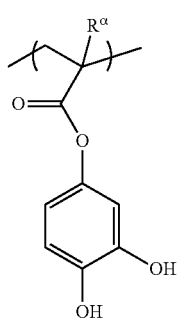
(a10-1-33)
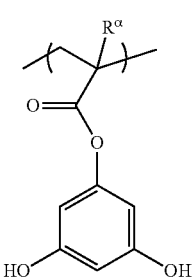
(a10-1-34)
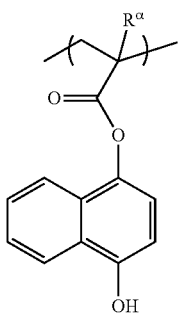

-continued (a10-1-35)
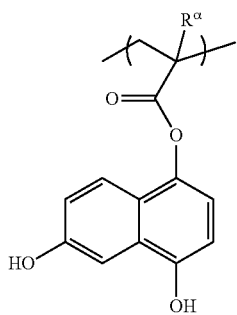

(a10-1-36)
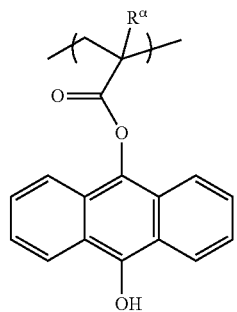

(a10-1-41)
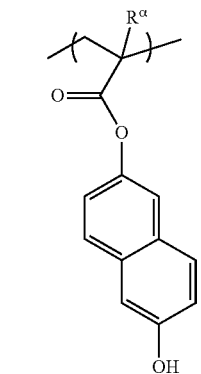

(a10-1-42)
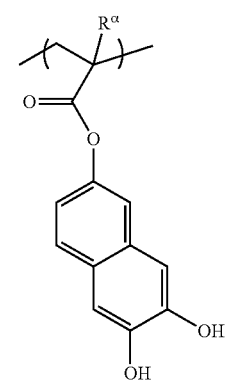

-continued (a10-1-43)
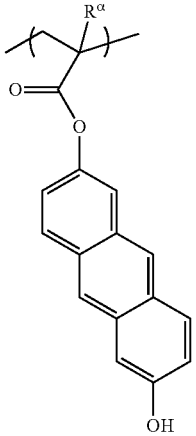

(a10-1-44)
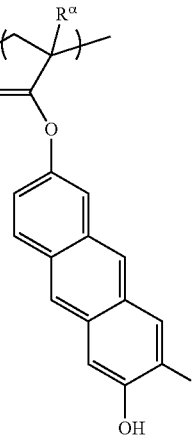

The constitutional unit (a10) contained in the component (A1) may be one kind or may be two or more kinds.

In a case where the component (A1) has the constitutional unit (a10), the proportion of the constitutional unit (a10) in the component (A1) is preferably in a range of 10% to 80% by mole, more preferably in a range of 20% to 60% by mole, and still more preferably in a range of 30% to 60% by mole, with respect to the total (100% by mole) of all constitutional units constituting the component (A1).

In a case where the proportion of the constitutional unit (a10) is set within the preferred range described above, the efficiency of supplying protons in the resist film can be improved and the solubility of the developing solution can be appropriately ensured, and thus the effects according to the present invention can be more easily obtained.

In Regard to Constitutional Unit (a8):

The constitutional unit (a8) is a constitutional unit derived from a compound represented by General Formula (a8-1).

(a8-1)
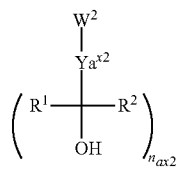

[In the formula, $W^2$ represents a polymerizable group-containing group. $Ya^{x2}$ represents a single bond or an ($n_{ax2}$+

1)-valent linking group. $Ya^{x2}$ and $W^2$ may form a condensed ring. $R^1$ represents a fluorinated alkyl group having 1 to 12 carbon atoms. $R^2$ represents an organic group having 1 to 12 carbon atoms, which may have a fluorine atom, or a hydrogen atom. $n_{ax2}$ represents an integer in a range of 1 to 3.]

In General Formula (a8-1), the polymerizable group-containing group as $W^2$ is the same as the polymerizable group-containing group as $W^{01}$ in General Formula (a0-1).

In General Formula (a8-1), $Ya^{x2}$ represents a single bond or an $(n_{ax2}+1)$-valent, that is, a divalent, trivalent, or tetravalent linking group.

Examples of the divalent linking group as $Ya^{x2}$ include the same ones as those described as the divalent linking group as $Ya^{x0}$ of $W^{01}$ in General Formula (a0-1). Examples of the trivalent linking group as $Ya^{x2}$ include a group obtained by removing one hydrogen atom from the above-described divalent linking group and a group obtained by bonding the divalent linking group to another divalent linking group. Examples of the tetravalent linking group include a group obtained by removing two hydrogen atoms from the divalent linking group.

$Ya^{x2}$ and $W^2$ may form a condensed ring.

In a case where $Ya^{x2}$ and $W^2$ form a condensed ring, examples of the ring structure of the condensed ring include a condensed ring of an alicyclic hydrocarbon with an aromatic hydrocarbon. The condensed ring formed by $Ya^{x2}$ and $W^2$ may have a hetero atom.

The alicyclic hydrocarbon moiety in the condensed ring formed by $Ya^{x2}$ and $W^2$ may be a monocyclic ring or a polycyclic ring.

Examples of the condensed ring formed by $Ya^{x2}$ and $W^2$ include a condensed ring formed by a polymerizable group of the $W^2$ moiety and by $Ya^{x2}$ and a condensed ring formed by a group other than the polymerizable group of the $W^2$ moiety and by $Ya^{x2}$. Specific examples thereof include a bicyclic condensed ring of a cycloalkene and an aromatic ring, a tricyclic condensed ring of a cycloalkene and two aromatic rings, and a bicyclic condensed ring of a cycloalkane having a polymerizable group as a substituent and an aromatic ring, and a tricyclic condensed ring of a cycloalkane having a polymerizable group as a substituent and an aromatic ring.

The condensed ring formed by $Ya^{x2}$ and $W^2$ may have a substituent. Examples of this substituent include a methyl group, an ethyl group, propyl group, a hydroxy group, a hydroxyalkyl group, a carboxy group, a halogen atom (a fluorine atom, a chlorine atom, a bromine atom, and the like), an alkoxy group (a methoxy group, an ethoxy group, a propoxy group, a butoxy group, and the like), an acyl group, an alkyloxycarbonyl group, and an alkylcarbonyloxy group.

Specific examples of the condensed ring formed by $Ya^{x2}$ and $W^2$ are shown below. $W^{\alpha}$ represents a polymerizable group.

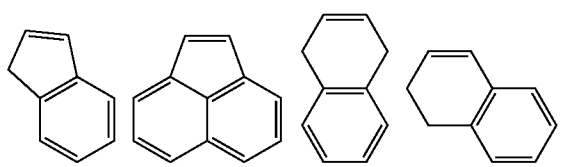

-continued

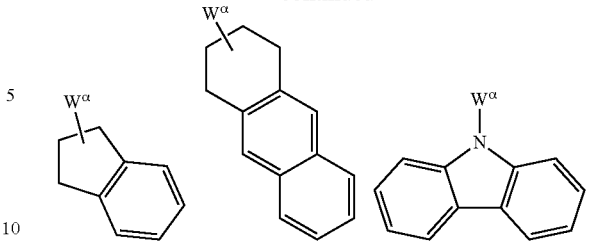

In General Formula (a8-1), $R^1$ represents a fluorinated alkyl group having 1 to 12 carbon atoms.

The fluorinated alkyl group having 1 to 12 carbon atoms is a group obtained by substituting part or all of hydrogen atoms in an alkyl group having 1 to 12 carbon atoms with a fluorine atom. The alkyl group may be linear or branched.

Specific examples of the linear fluorinated alkyl group having 1 to 12 carbon atoms include a methyl group, an ethyl group, a propyl group, a butyl group, a pentyl group, a hexyl group, a heptyl group, an octyl group, a nonyl group, a decyl group, and an undecyl group, a group obtained by substituting part or all of hydrogen atoms of a dodecyl group with a fluorine atom. Specific examples of the branched fluorinated alkyl group having 1 to 12 carbon atoms include a 1-methylethyl group, a 1,1-dimethylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a group obtained by substituting part or all of hydrogen atoms of a 4-methylpentyl group with a fluorine atom.

Among the above, the fluorinated alkyl group having 1 to 12 carbon atoms of $R^1$ is preferably a fluorinated alkyl group having 1 to 5 carbon atoms and particularly preferably a trifluoromethyl group.

In General Formula (a8-1), $R^2$ represents an organic group having 1 to 12 carbon atoms, which may have a fluorine atom, or a hydrogen atom.

Examples of the organic group having 1 to 12 carbon atoms as $R^2$, which may have a fluorine atom, include a monovalent hydrocarbon group having 1 to 12 carbon atoms, which may have a fluorine atom.

Examples of the hydrocarbon group include a linear or branched alkyl group and a cyclic hydrocarbon group.

Specific examples of the linear alkyl group include a methyl group, an ethyl group, a propyl group, a butyl group, a pentyl group, a hexyl group, a heptyl group, an octyl group, a nonyl group, a decyl group, an undecyl group, and a dodecyl group.

Specific examples of the branched alkyl group include a 1-methylethyl group, a 1,1-dimethylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

In a case where $R^2$ represents a cyclic hydrocarbon group, the cyclic hydrocarbon group may be an aliphatic hydrocarbon group or an aromatic hydrocarbon group and may be a polycyclic group or a monocyclic group.

The aliphatic hydrocarbon group which is a monocyclic group is preferably a group obtained by removing one hydrogen atom from a monocycloalkane. The monocycloalkane preferably has 3 to 6 carbon atoms, and specific examples thereof include cyclopentane and cyclohexane.

The aliphatic hydrocarbon group which is a polycyclic group is preferably a group obtained by removing one hydrogen atom from a polycycloalkane, where the polycycloalkane preferably has 7 to 12 carbon atoms. Specific examples thereof include adamantane, norbornane, isobornane, tricyclodecane, and tetracyclododecane.

In a case where the cyclic hydrocarbon group as $R^2$ is an aromatic hydrocarbon group, the aromatic hydrocarbon group is a hydrocarbon group having at least one aromatic ring. Specific examples of the aromatic hydrocarbon group include a group obtained by removing one hydrogen atom from an aromatic hydrocarbon ring such as benzene, naphthalene, anthracene, phenanthrene, biphenyl, and fluorene.

The organic group having 1 to 12 carbon atoms as $R^2$ may have a substituent other than a fluorine atom. Examples of the substituent include a hydroxy group, a carboxy group, a halogen atom (a chlorine atom, a bromine atom, and the like), an alkoxy group (a methoxy group, an ethoxy group, a propoxy group, a butoxy group, and the like), and an alkyloxycarbonyl group.

$R^2$ is preferably a fluorinated alkyl group having 1 to 12 carbon atoms, more preferably a fluorinated alkyl group having 1 to 5 carbon atoms, and still more preferably a trifluoromethyl group.

In General Formula (a8-1), $n_{ax2}$ represents an integer in a range of 1 to 3, preferably 1 or 2, and more preferably 1.

The constitutional unit (a8) is preferably a constitutional unit (a81) derived from a compound represented by General Formula (a8-1-1).

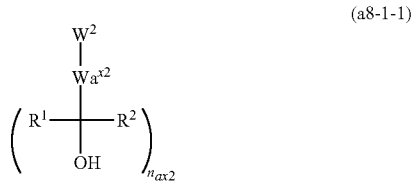

(a8-1-1)

[In General Formula (a8-1-1), $W^2$ represents a polymerizable group-containing group. $Wa^{x2}$ represents an $(n_{ax2}+1)$ valent cyclic group. $W^2$ and $Wa^{x2}$ may form a condensed ring. $R^1$ represents a fluorinated alkyl group having 1 to 12 carbon atoms. $R^2$ represents an organic group having 1 to 12 carbon atoms, which may have a fluorine atom, or a hydrogen atom. $n_{ax2}$ represents an integer in a range of 1 to 3.]

In General Formula (a8-1-1), $W^2$, $R^1$, $R^2$, and $n_{ax2}$ are each the same as $W^2$, R', $R^2$, and $n_{ax2}$ in General Formula (a8-1).

In General Formula (a8-1-1), $Wa^{x2}$ is a $(n_{ax2}+1)$ valent cyclic group.

Examples of the cyclic group as $Wa^{x2}$ include an aliphatic cyclic group and an aromatic cyclic group, and the cyclic group may be a monocyclic ring or a polycyclic ring.

The aliphatic cyclic group which is a monocyclic group is preferably a group obtained by removing one hydrogen atom from a monocycloalkane. The monocycloalkane preferably has 3 to 6 carbon atoms, and specific examples thereof include cyclopentane and cyclohexane.

The aliphatic cyclic group which is a polycyclic group is preferably a group obtained by removing one hydrogen atom from a polycycloalkane. The polycycloalkane preferably has 7 to 12 carbon atoms, and specific examples thereof include a group obtained by removing one or more hydrogen atoms from a polycycloalkane such as decalin, perhydroazulene, or perhydroanthracene.

The aromatic cyclic group is a hydrocarbon group having at least one aromatic ring. The aromatic ring is not particularly limited as long as it is a cyclic conjugated system having $(4n+2)\pi$ electrons. The aromatic ring preferably has 5 to 30 carbon atoms, more preferably 5 to 20 carbon atoms, still more preferably 6 to 15 carbon atoms, and particularly preferably 6 to 12 carbon atoms. Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring. Specific examples of the aromatic hydrocarbon group include a group obtained by removing one hydrogen atom from the above-described aromatic hydrocarbon ring or aromatic heterocyclic ring (an aryl group or a heteroaryl group); a group obtained by removing one hydrogen atom from an aromatic compound having two or more aromatic rings (biphenyl, fluorene or the like); and a group obtained by substituting one hydrogen atom of the above-described aromatic hydrocarbon ring or aromatic heterocyclic ring with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aromatic hydrocarbon ring or aromatic heterocyclic ring preferably has 1 to 4 carbon atoms, more preferably 1 or 2 carbon atoms, and particularly preferably 1 carbon atom.

Examples of the substituent which may be contained in the cyclic group as $Wa^{x2}$ include a carboxy group, a halogen atom (a fluorine atom, a chlorine atom, a bromine atom, and the like), an alkoxy group (a methoxy group, an ethoxy group, a propoxy group, a butoxy group, and the like), and an alkyloxycarbonyl group.

$W^2$ and $Wa^{x2}$ may form a condensed ring, which is the same condensed ring as that described in the condensed ring formed by $Ya^{x2}$ and $W^2$ in General Formula (a8-1).

Specific examples of the constitutional unit (a8) are as follows.

In the formulae shown below, $R^\alpha$ represents a hydrogen atom, a methyl group, or a trifluoromethyl group.

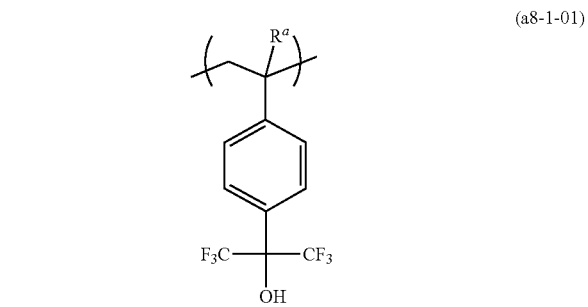

(a8-1-01)

(a8-1-02) 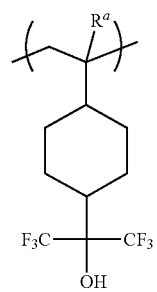

(a8-1-03) 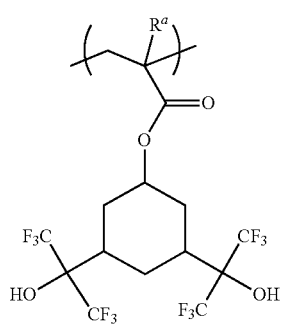

(a8-1-04) 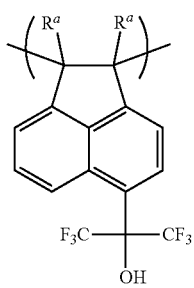

(a8-1-05) 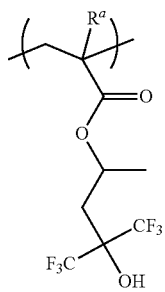

(a02-1-06) 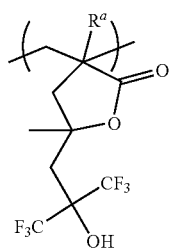

(a8-1-07) 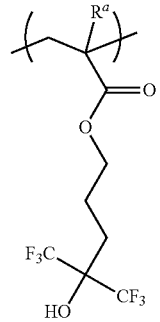

(a8-1-08) 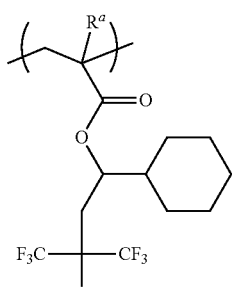

(a8-1-09) 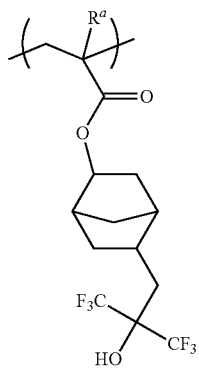

(a8-1-10) 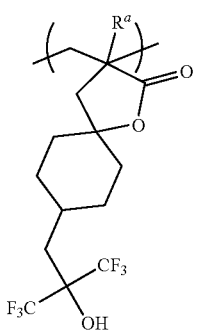

Among the above examples, the constitutional unit (a8) is preferably a constitutional unit represented by Chemical Formula (a8-1-09).

The constitutional unit (a8) contained in the component (A1) may be one kind or may be two or more kinds.

In a case where the component (A1) has the constitutional unit (a8), the proportion of the constitutional unit (a8) is preferably in a range of 1% to 30% by mole, more preferably in a range of 3% to 20% by mole, and still more preferably in a range of 5% to 15% by mole, with respect to the total (100% by mole) of all constitutional units constituting the component (A1).

In a case where the proportion of the constitutional unit (a8) is equal to or larger than the lower limit value of the preferred range, the compatibility with the developing solution and the rinse liquid can be enhanced. On the other hand, in a case where the proportion is equal to or smaller than the upper limit value of the preferred range, balance with other constitutional units can be obtained, and various lithography characteristics are improved.

In Regard to Constitutional Unit (a2):

The component (A1) may further have a constitutional unit (a2) (provided that a constitutional unit corresponding to the constitutional unit (a01) or the constitutional unit (a1) is excluded) containing a lactone-containing cyclic group, a —SO$_2$—-containing cyclic group, or a carbonate-containing cyclic group.

In a case where the component (A1) is used for forming a resist film, the lactone-containing cyclic group, the —SO$_2$—-containing cyclic group, or the carbonate-containing cyclic group in the constitutional unit (a2) is effective for improving the adhesiveness of the resist film to the substrate. Further, due to having the constitutional unit (a2), lithography characteristics can be improved, for example, by the effects obtained by appropriately adjusting the acid diffusion length, increasing the adhesiveness of the resist film to the substrate, and appropriately adjusting the solubility during development.

The "lactone-containing cyclic group" indicates a cyclic group that contains a ring (lactone ring) containing a —O—C(=O)— in the ring skeleton. In a case where the lactone ring is counted as the first ring and the group contains only the lactone ring, the group is referred to as a monocyclic group. Further, in a case where the group has other ring structures, the group is referred to as a polycyclic group regardless of the structures. The lactone-containing cyclic group may be a monocyclic group or a polycyclic group.

The lactone-containing cyclic group for the constitutional unit (a2) is not particularly limited, and any lactone-containing cyclic group may be used. Specific examples thereof include groups each represented by General Formulae (a2-r-1) to (a2-r-7) shown below.

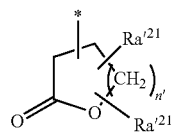

(a2-r-1)

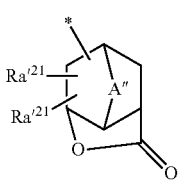

(a2-r-2)

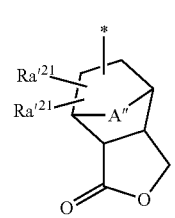

(a2-r-3)

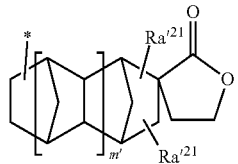

(a2-r-4)

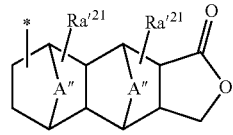

(a2-r-5)

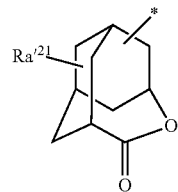

(a2-r-6)

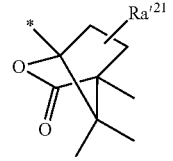

(a2-r-7)

[In the formulae, each $R'^{21}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —SO$_2$—-containing cyclic group; A" represents an oxygen atom, a sulfur atom, or an alkylene group having 1 to 5 carbon atoms, which may contain an oxygen atom (—O—) or a sulfur atom (—S—); and n' represents an integer in a range of 0 to 2, and m' is 0 or 1.]

In General Formulae (a2-r-1) to (a2-r-7), the alkyl group as $R'^{21}$ is preferably an alkyl group having 1 to 6 carbon atoms. The alkyl group is preferably a linear alkyl group or a branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, and a hexyl group. Among these, a methyl group or ethyl group is preferable, and a methyl group is particularly preferable.

The alkoxy group as $R'^{21}$ is preferably an alkoxy group having 1 to 6 carbon atoms. Further, the alkoxy group is preferably a linear or branched alkoxy group. Specific examples of the alkoxy groups include a group that is formed by linking the above-described alkyl group mentioned as the alkyl group represented by $R'^{21}$ to an oxygen atom (—O—).

The halogen atom as $R'^{21}$ is preferably a fluorine atom.

Examples of the halogenated alkyl group as $R'^{21}$ include a group obtained by substituting part or all of hydrogen atoms in the above-described alkyl group as $R'^{21}$ with the above-described halogen atom. The halogenated alkyl group is preferably a fluorinated alkyl group and particularly preferably a perfluoroalkyl group.

In —COOR" and —OC(═O)R" as $R'^{21}$, R" represents a hydrogen atom, an alkyl group, a lactone-containing cyclic group, a carbonate-containing cyclic group, or a —SO$_2$—-containing cyclic group.

The alkyl group as R" may be linear, branched, or cyclic, and preferably has 1 to 15 carbon atoms.

In a case where R" represents a linear or branched alkyl group, it is preferably an alkyl group having 1 to 10 carbon atoms, more preferably an alkyl group having 1 to 5 carbon atoms, and particularly preferably a methyl group or an ethyl group.

In a case where R" represents a cyclic alkyl group, the cyclic alkyl group preferably has 3 to 15 carbon atoms, more preferably 4 to 12 carbon atoms, and particularly preferably 5 to 10 carbon atoms. Specific examples thereof include a group obtained by removing one or more hydrogen atoms from a monocycloalkane, which may or may not be substituted with a fluorine atom or a fluorinated alkyl group; and a group obtained by removing one or more hydrogen atoms from a polycycloalkane such as bicycloalkane, tricycloalkane, or tetracycloalkane. More specific examples thereof include a group obtained by removing one or more hydrogen atoms from a monocycloalkane such as cyclopentane or cyclohexane; and a group obtained by removing one or more hydrogen atoms from a polycycloalkane such as adamantane, norbornane, isobornane, tricyclodecane, or tetracyclododecane.

Examples of the lactone-containing cyclic group as R" include the same ones as those each represented by General Formulae (a2-r-1) to (a2-r-7).

The carbonate-containing cyclic group as R" has the same definition as that for the carbonate-containing cyclic group described below. Specific examples of the carbonate-containing cyclic group include groups each represented by General Formulae (ax3-r-1) to (ax3-r-3).

The —SO$_2$—-containing cyclic group as R" has the same definition as that for the —SO$_2$—-containing cyclic group described below. Specific examples thereof include groups each represented by General Formulae (a5-r-1) to (a5-r-4).

The hydroxyalkyl group as $R'^{21}$ preferably has 1 to 6 carbon atoms, and specific examples thereof include a group obtained by substituting at least one hydrogen atom in the alkyl group as $R'^{21}$ with a hydroxyl group.

In General Formulae (a2-r-2), (a2-r-3) and (a2-r-5), as the alkylene group having 1 to 5 carbon atoms as A", a linear or branched alkylene group is preferable, and examples thereof include a methylene group, an ethylene group, an n-propylene group, and an isopropylene group. Specific examples of the alkylene groups that contain an oxygen atom or a sulfur atom include a group obtained by interposing —O— or —S— in the terminal of the alkylene group or between the carbon atoms of the alkylene group, and examples thereof include —O—CH$_2$—, —CH$_2$—O—CH$_2$—, —S—CH$_2$—, and —CH$_2$—S—CH$_2$—. A" is preferably an alkylene group having 1 to 5 carbon atoms or —O—, more preferably an alkylene group having 1 to 5 carbon atoms, and most preferably a methylene group.

Specific examples of the groups each represented by General Formulae (a2-r-1) to (a2-r-7) are shown below.

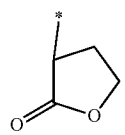

(r-lc-1-1)

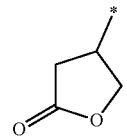

(r-lc-1-2)

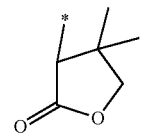

(r-lc-1-3)

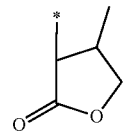

(r-lc-1-4)

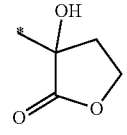

(r-lc-1-5)

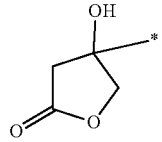

(r-lc-1-6)

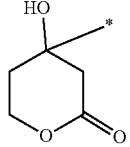

(r-lc-1-7)

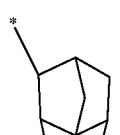

(r-lc-2-1)

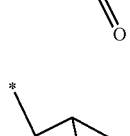

(r-lc-2-2)

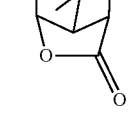

(r-lc-2-3)

-continued
(r-lc-2-4)
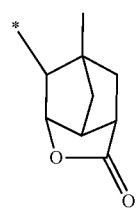
(r-lc-2-5)
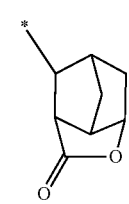
(r-lc-2-6)
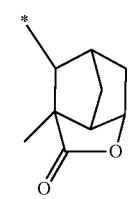
(r-lc-2-7)
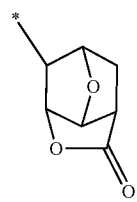
(r-lc-2-8)
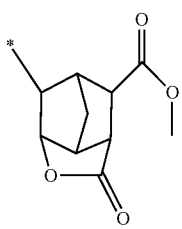
(r-lc-2-9)
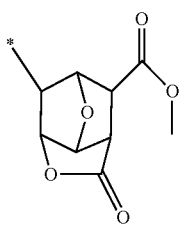
(r-lc-2-10)
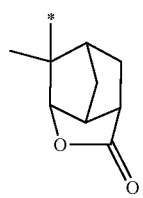
-continued
(r-lc-2-11)
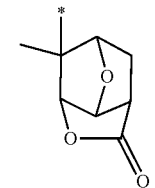
(r-lc-2-12)
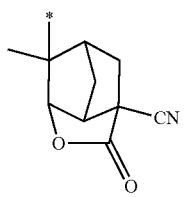
(r-lc-2-13)
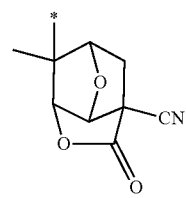
(r-lc-2-14)
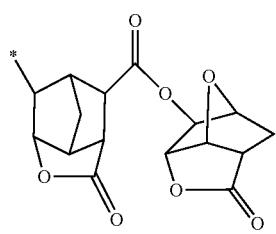
(r-lc-2-15)
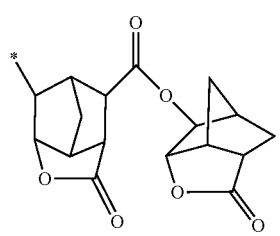
(r-lc-2-16)
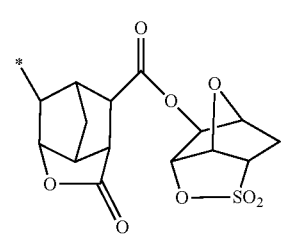
(r-lc-2-17)
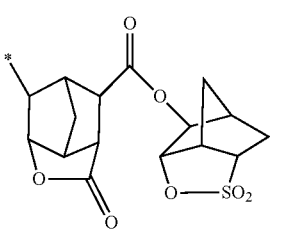

-continued
(r-lc-2-18)
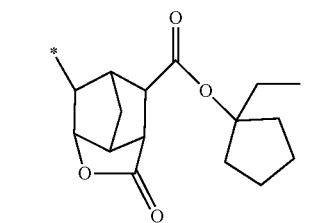
r-lc-3-1
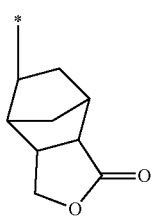
r-lc-3-2
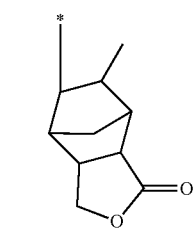
r-lc-3-3
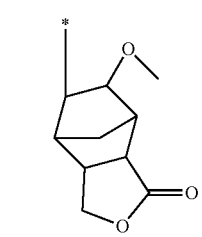
r-lc-3-4
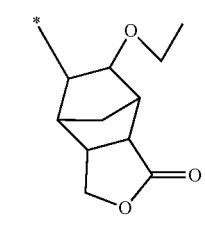
r-lc-3-5
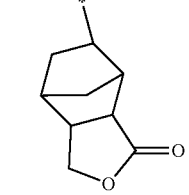
(r-lc-4-1)
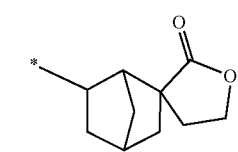
-continued
(r-lc-4-2)
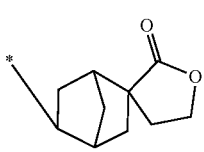
(r-lc-4-3)
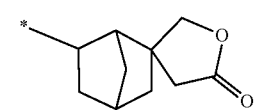
(r-lc-4-4)
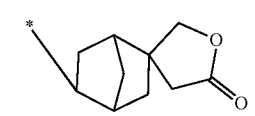
(r-lc-4-5)
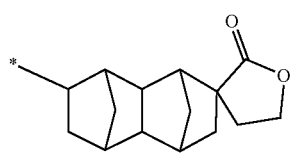
(r-lc-4-6)
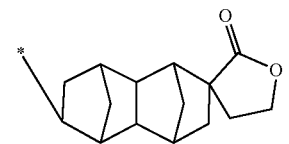
(r-lc-4-7)
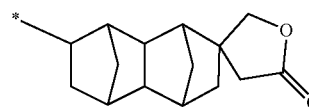
(r-lc-4-8)
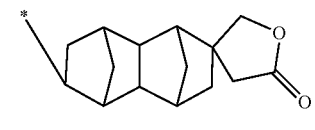
(r-lc-4-9)
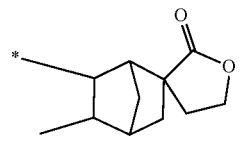
r-lc-5-1
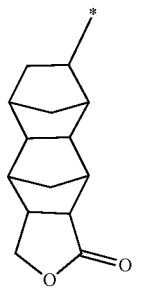

-continued (r-lc-5-2)
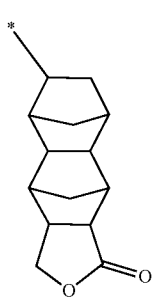

(r-lc-5-3)
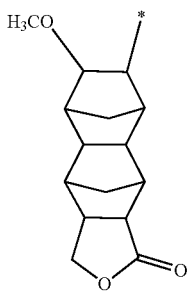

(r-lc-5-4)
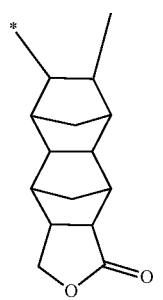

(r-lc-6-1)
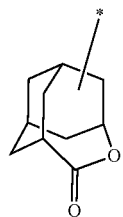

(r-lc-7-1)
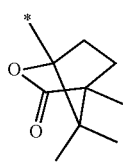

The "—$SO_2$—-containing cyclic group" indicates a cyclic group having a ring containing —$SO_2$— in the ring skeleton thereof. Specifically, the —$SO_2$—-containing cyclic group is a cyclic group in which the sulfur atom (S) in —$SO_2$— forms a part of the ring skeleton of the cyclic group. In a case where a ring containing —$SO_2$— in the ring skeleton thereof is counted as the first ring and the group contains only the ring, the group is referred to as a monocyclic group. In a case where the group further has other ring structures, such a group is referred to as a polycyclic group regardless of the structures. The —$SO_2$—-containing cyclic group may be a monocyclic group or a polycyclic group.

Particularly, the —$SO_2$—-containing cyclic group is preferably a cyclic group containing —O—$SO_2$— in the ring skeleton thereof, in other words, a cyclic group containing a sultone ring in which —O—S— in the —O—$SO_2$— group forms a part of the ring skeleton thereof.

More specific examples of the —$SO_2$—-containing cyclic group include groups each represented by General Formulae (a5-r-1) to (a5-r-4) shown below.

(a5-r-1)
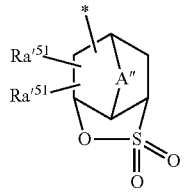

(a5-r-2)
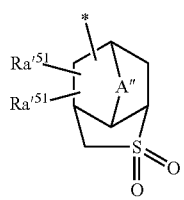

(a5-r-3)
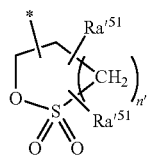

(a5-r-4)
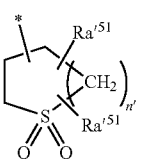

[In the formulae, each $R'^{51}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —$SO_2$—-containing cyclic group; A" represents an oxygen atom, a sulfur atom, or an alkylene group having 1 to 5 carbon atoms, which may contain an oxygen atom or a sulfur atom; and n' represents an integer in a range of 0 to 2.]

In General Formulae (a5-r-1) and (a5-r-2), A" has the same definition as that for A" in General Formulae (a2-r-2), (a2-r-3) and (a2-r-5).

Examples of the alkyl group, the alkoxy group, the halogen atom, the halogenated alkyl group, —COOR", —OC(=O)R", and the hydroxyalkyl group, as $R'^{51}$, include the same ones as those described in the explanation of $R'^{21}$ in General Formulae (a2-r-1) to (a2-r-7).

Specific examples of the groups each represented by General Formulae (a5-r-1) to (a5-r-4) are shown below. In the formulae shown below, "Ac" represents an acetyl group.

(r-s1-1-1) 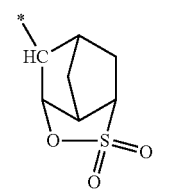
(r-s1-1-2) 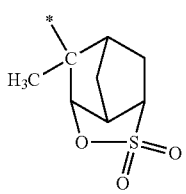
(r-s1-1-3) 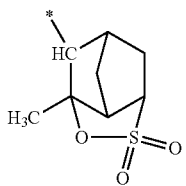
(r-s1-1-4) 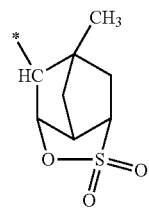
(r-s1-1-5) 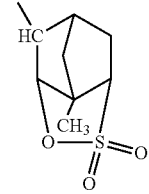
(r-s1-1-6) 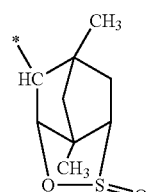
(r-s1-1-7) 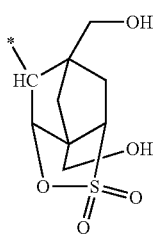
(r-s1-1-8) 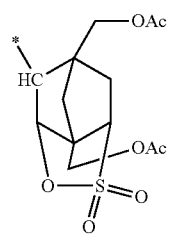
(r-s1-1-9) 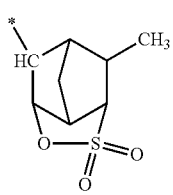
(r-s1-1-10) 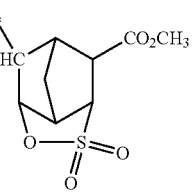
(r-s1-1-11) 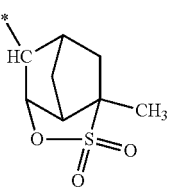
(r-s1-1-12) 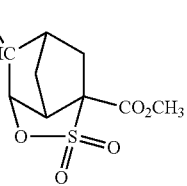
(r-s1-1-13) 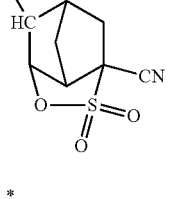
(r-s1-1-14) 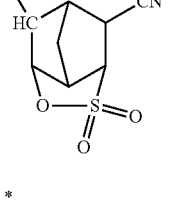
(r-s1-1-15) 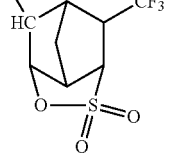

(r-s1-1-16)
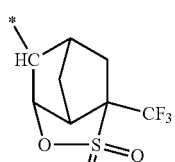
(r-s1-1-17)
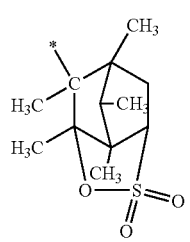
(r-s1-1-18)
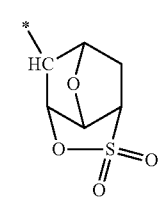
(r-s1-1-19)
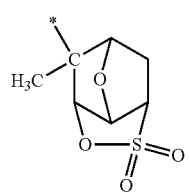
(r-s1-1-20)
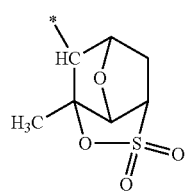
(r-s1-1-21)
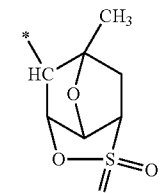
(r-s1-1-22)
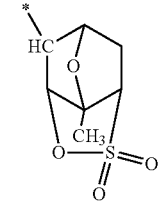
(r-s1-1-23)
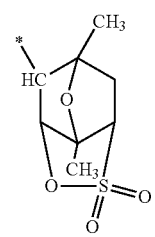
(r-s1-1-24)
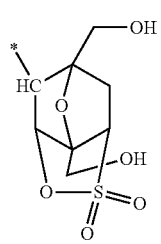
(r-s1-1-25)
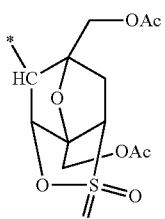
(r-s1-1-26)
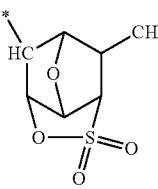
(r-s1-1-27)
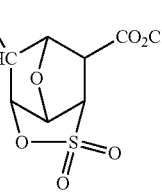
(r-s1-1-28)
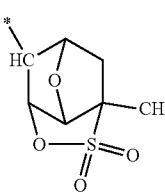
(r-s1-1-29)
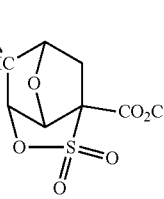

-continued

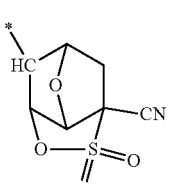
(r-s1-1-30)

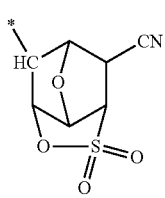
(r-s1-1-31)

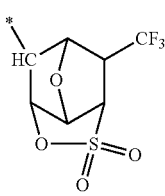
(r-s1-1-32)

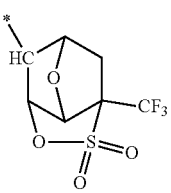
(r-s1-1-33)

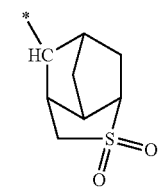
(r-s1-2-1)

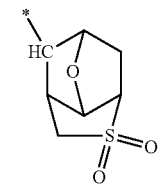
(r-s1-2-2)

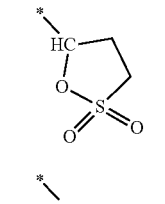
(r-s1-3-1)

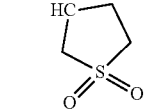
(r-s1-4-1)

The "carbonate-containing cyclic group" indicates a cyclic group having a ring (a carbonate ring) containing —O—C(=O)—O— in the ring skeleton thereof. In a case where the carbonate ring is counted as the first ring and the group contains only the carbonate ring, the group is referred to as a monocyclic group. Further, in a case where the group has other ring structures, the group is referred to as a polycyclic group regardless of the structures. The carbonate-containing cyclic group may be a monocyclic group or a polycyclic group.

The carbonate ring-containing cyclic group is not particularly limited, and any carbonate ring-containing cyclic group may be used. Specific examples thereof include groups each represented by General Formulae (ax3-r-1) to (ax3-r-3) shown below.

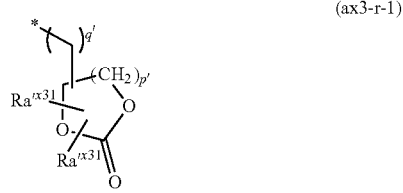
(ax3-r-1)

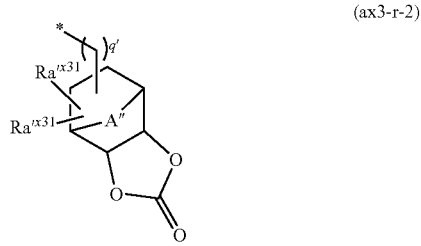
(ax3-r-2)

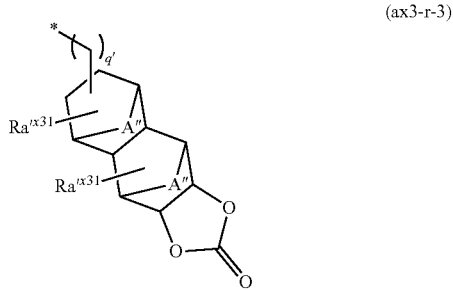
(ax3-r-3)

[In the formulae, each $Ra'^{x31}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —SO$_2$—-containing cyclic group; A" represents an oxygen atom, a sulfur atom, or an alkylene group having 1 to 5 carbon atoms, which may contain an oxygen atom or a sulfur atom; and p' represents an integer in a range of 0 to 3, and q' is 0 or 1.]

In General Formulae (ax3-r-2) and (ax3-r-3), A" has the same definition as that for A" in General Formulae (a2-r-2), (a2-r-3) and (a2-r-5).

Examples of the alkyl group, the alkoxy group, the halogen atom, the halogenated alkyl group, —COOR", —OC(=O)R", and the hydroxyalkyl group, as $R'^{31}$, include the same ones as those described in the explanation of $R'^{21}$ in General Formulae (a2-r-1) to (a2-r-7).

Specific examples of the groups each represented by General Formulae (ax3-r-1) to (ax3-r-3) are shown below.

(r-cr-1-1) 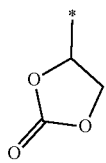
(r-cr-1-2) 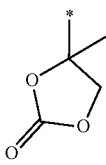
(r-cr-1-3) 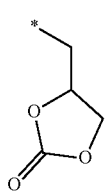
(r-cr-1-4) 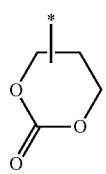
(r-cr-1-5) 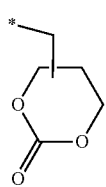
(r-cr-1-6) 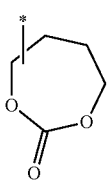
(r-cr-1-7) 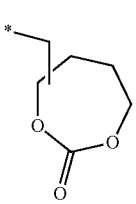
(r-cr-2-1) 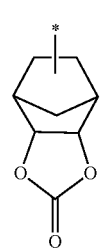
(r-cr-2-2) 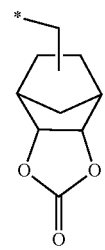
(r-cr-2-3) 
(r-cr-2-4) 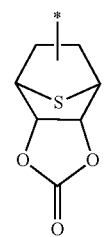
(r-cr-3-1) 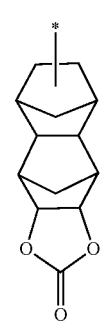
(r-cr-3-2) 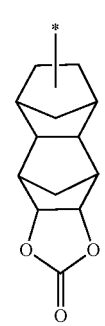

-continued (r-cr-3-2)
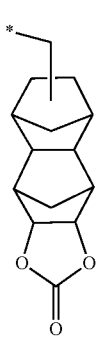

(r-cr-3-3)
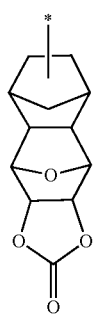

(r-cr-3-4)
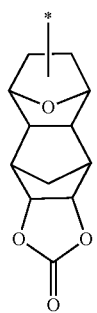

(r-cr-3-5)
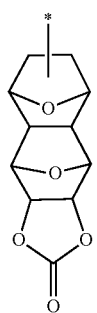

Among them, the constitutional unit (a2) is preferably a constitutional unit derived from acrylic acid ester in which the hydrogen atom bonded to the carbon atom at the α-position may be substituted with a substituent.

The constitutional unit (a2) is preferably a constitutional unit represented by General Formula (a2-1).

(a2-1)
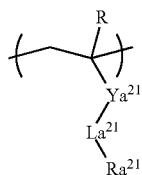

[In the formula, R represents a hydrogen atom, an alkyl group having 1 to 5 carbon atoms, or a halogenated alkyl group having 1 to 5 carbon atoms. $Ya^{21}$ represents a single bond or a divalent linking group. $La^{21}$ represents —O—, —COO—, —CON(R')—, —OCO—, —CONHCO— or —CONHCS—, and R' represents a hydrogen atom or a methyl group. However, in a case where $La^{21}$ represents —O—, $Ya^{21}$ does not represent —CO—. $Ra^{21}$ represents a lactone-containing cyclic group, a carbonate-containing cyclic group, or a —$SO_2$—-containing cyclic group.]

In General Formula (a2-1), R has the same definition as described above. R is preferably a hydrogen atom, an alkyl group having 1 to 5 carbon atoms, or a fluorinated alkyl group having 1 to 5 carbon atoms, and it is particularly preferably a hydrogen atom or a methyl group in terms of industrial availability.

In General Formula (a2-1), examples of the divalent linking group as $Ya^{21}$ include the same one as the divalent linking group as $Ya^{x0}$ of $W^{01}$ in General Formula (a0-1).

Among the above, $Ya^{21}$ is preferably a single bond, an ester bond [—C(=O)—O—], an ether bond (—O—), a linear or branched alkylene group, or a combination thereof.

In General Formula (a2-1), $Ra^{21}$ represents a lactone-containing cyclic group, a —$SO_2$—-containing cyclic group, or a carbonate-containing cyclic group.

Suitable examples of the lactone-containing cyclic group, the —$SO_2$—-containing cyclic group, and the carbonate-containing cyclic group as $Ra^{21}$ include groups each represented by General Formulae (a2-r-1) to (a2-r-7), groups each represented by General Formulae (a5-r-1) to (a5-r-4), and groups each represented by General Formulae (ax3-r-1) to (ax3-r-3) described above.

Among them, a lactone-containing cyclic group or a —$SO_2$—-containing cyclic group is preferable, and groups each represented by General Formula (a2-r-1), (a2-r-2), (a2-r-6), or (a5-r-1) are more preferable. Specifically, any one of groups each represented by Chemical Formulae (r-1c-1-1) to (r-1c-1-7), (r-1c-2-1) to (r-1c-2-18), (r-1c-6-1), (r-s1-1-1), and (r-s1-1-18) is more preferable, and a group represented by Chemical Formula (r-1c-2-1) is preferable.

The constitutional unit (a2) contained in the component (A1) may be one kind or may be two or more kinds.

In a case where the component (A1) has the constitutional unit (a2), the proportion of the constitutional unit (a2) is preferably in a range of 1% to 40% by mole and more preferably in a range of 10% to 30% by mole, with respect to the total (100% by mole) of all constitutional units constituting the component (A1).

In a case where the proportion of the constitutional unit (a2) is equal to or larger than the lower limit value of the preferred range, the effect that is obtained by allowing the constitutional unit (a2) to be contained can be sufficiently achieved by the effect described above. In a case where it is equal to or smaller than the upper limit value of the preferred range, the balance with other constitutional units can be obtained, and various lithography characteristics are improved.

In Regard to Constitutional Unit (a3):

The component (A1) may further have, a constitutional unit (a3) (provided that a constitutional unit corresponding to the constitutional unit (a01), the constitutional unit (a1), the constitutional unit (a2), or the constitutional unit (a8) is excluded) containing a polar group-containing aliphatic hydrocarbon group. In a case where the component (A1) has the constitutional unit (a3), the hydrophilicity of the component (A1) is increased, which contributes to an improvement in resolution. Further, acid diffusion length can be appropriately adjusted.

Examples of the polar group include a hydroxyl group, a cyano group, and a carboxy group, and a hydroxyl group is particularly preferable.

Examples of the aliphatic hydrocarbon group include a linear or branched hydrocarbon group (preferably an alkylene group) having 1 to 10 carbon atoms, and a cyclic aliphatic hydrocarbon group (a cyclic group). The cyclic group may be a monocyclic group or a polycyclic group. For example, these cyclic groups can be appropriately selected from a large number of groups that have been proposed in resins for a resist composition for an ArF excimer laser.

In a case where the cyclic group is a monocyclic group, the monocyclic group preferably has 3 to 10 carbon atoms. Among the above, a constitutional unit derived from an acrylic acid ester containing an aliphatic monocyclic group, which contains a hydroxyl group, a cyano group, or a carboxy group, is more preferable. Examples of the monocyclic group include a group obtained by removing two or more hydrogen atoms from a monocycloalkane. Specific examples of the monocyclic group include a group obtained by removing two or more hydrogen atoms from a monocycloalkane such as cyclopentane, cyclohexane, or cyclooctane. Among these monocyclic groups, a group obtained by removing two or more hydrogen atoms from cyclopentane or a group obtained by removing two or more hydrogen atoms from cyclohexane are industrially preferable.

In a case where the cyclic group is a polycyclic group, the polycyclic group preferably has 7 to 30 carbon atoms. Among the above, a constitutional unit derived from an acrylic acid ester containing an aliphatic polycyclic group, which contains a hydroxyl group, a cyano group, or a carboxy group, is more preferable. Examples of the polycyclic group include groups obtained by removing two or more hydrogen atoms from a bicycloalkane, tricycloalkane, tetracycloalkane, or the like. Specific examples thereof include a group obtained by removing two or more hydrogen atoms from a polycycloalkane such as adamantane, norbornane, isobornane, tricyclodecane, or tetracyclododecane. Among these polycyclic groups, a group obtained by removing two or more hydrogen atoms from adamantane, a group obtained by removing two or more hydrogen atoms from norbornane, or a group obtained by removing two or more hydrogen atoms from tetracyclododecane are industrially preferable.

The constitutional unit (a3) is not particularly limited, and any constitutional unit may be used as long as the constitutional unit contains a polar group-containing aliphatic hydrocarbon group.

The constitutional unit (a3) is a constitutional unit derived from acrylic acid ester in which the hydrogen atom bonded to the carbon atom at the α-position may be substituted with a substituent, and a constitutional unit containing a polar group-containing aliphatic hydrocarbon group is preferable.

In a case where the hydrocarbon group in the polar group-containing aliphatic hydrocarbon group is a linear or branched hydrocarbon group having 1 to 10 carbon atoms, the constitutional unit (a3) is preferably a constitutional unit derived from a hydroxyethyl ester of acrylic acid.

Examples of the preferred constitutional unit (a3) include a constitutional unit represented by General Formula (a3-1) and a constitutional unit represented by General Formula (a3-2), shown below.

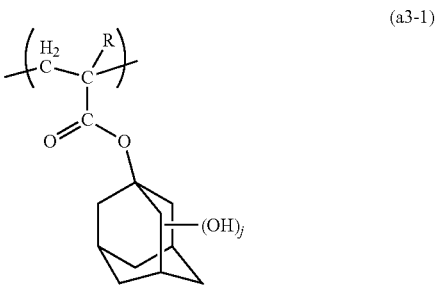

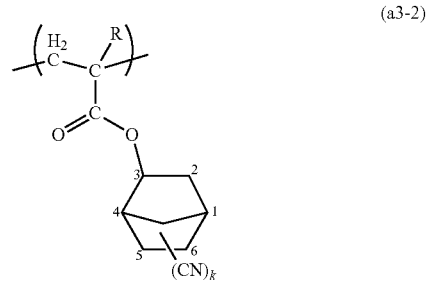

[In the formula, R is the same as above, j represents an integer in a range of 1 to 3, and k represents an integer in a range of 1 to 3.]

In General Formula (a3-1), j preferably represents 1 or 2 and more preferably 1. In a case where j represents 2, it is preferable that the hydroxyl groups are bonded to the 3-position and 5-position of the adamantyl group. In a case where j represents 1, it is preferable that the hydroxyl group is bonded to the 3-position of the adamantyl group.

It is preferable that j represents 1, and it is particularly preferable that the hydroxyl group is bonded to the 3-position of the adamantyl group.

In General Formula (a3-2), k preferably represents 1. The cyano group is preferably bonded to the 5-position or 6-position of the norbornyl group.

The constitutional unit (a3) contained in the component (A1) may be one kind or may be two or more kinds.

In a case where the component (A1) has the constitutional unit (a3), the proportion of the constitutional unit (a3) is preferably in a range of 1% to 30% by mole, more preferably in a range of 3% to 20% by mole, and still more preferably in a range of 5% to 15% by mole, with respect to the total (100% by mole) of all constitutional units constituting the component (A1).

In a case where the proportion of the constitutional unit (a3) is equal to or larger than the lower limit value of the preferred range, the effect that is obtained by allowing the constitutional unit (a3) to be contained can be sufficiently achieved by the effect described above. In a case where the proportion of the constitutional unit (a3) is equal to or smaller than the upper limit value of the preferred range, balance with other constitutional units can be obtained, and various lithography characteristics are improved.

In Regard to Constitutional Unit (a4):

The component (A1) may further have a constitutional unit (a4) containing an acid non-dissociable aliphatic cyclic group.

In a case where the component (A1) has the constitutional unit (a4), the dry etching resistance of the formed resist pattern is improved. Further, the hydrophobicity of the component (A1) increases. The improvement in hydrophobicity contributes to the improvement in resolution, a resist pattern shape, and the like, particularly in the case of a solvent developing process.

The "acid non-dissociable cyclic group" in the constitutional unit (a4) is a cyclic group that remains in the constitutional unit without being dissociated even when an acid acts in a case where the acid is generated in the resist composition upon exposure (for example, in a case where an acid is generated from the constitutional unit or the component (B) that generates acid upon exposure).

Examples of the constitutional unit (a4) preferably include a constitutional unit derived from an acrylic acid ester including an acid non-dissociable aliphatic cyclic group. As the cyclic group, many cyclic groups known in the related art as the cyclic group used as a resin component of a resist composition for an ArF excimer laser, a KrF excimer laser (preferably an ArF excimer laser), or the like can be used.

The cyclic group is particularly preferably at least one selected from a tricyclodecyl group, an adamantyl group, a tetracyclododecyl group, an isobornyl group, and a norbornyl group, from the viewpoint of industrial availability. These polycyclic groups may have, as a substituent, a linear or branched alkyl group having 1 to 5 carbon atoms.

Specific examples of the constitutional unit (a4) include constitutional units each represented by General Formulae (a4-1) to (a4-7).

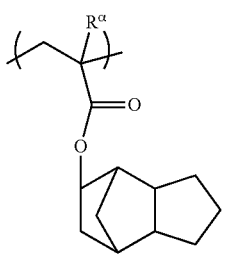

(a4-1)

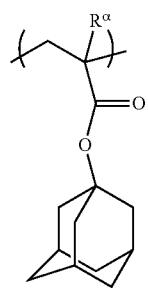

(a4-2)

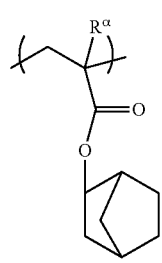

(a4-3)

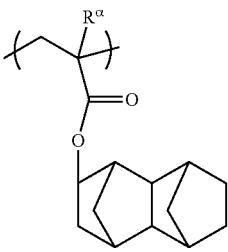

(a4-4)

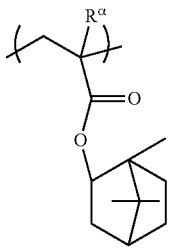

(a4-5)

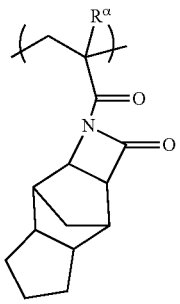

(a4-6)

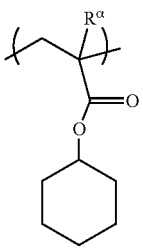

(a4-7)

[In the formula, $R^\alpha$ is the same as above.]

The constitutional unit (a4) contained in the component (A1) may be one kind or may be two or more kinds.

In a case where the component (A1) has the constitutional unit (a4), the proportion of the constitutional unit (a4) is preferably in a range of 1% to 40% by mole and more preferably in a range of 1% to 20% by mole, with respect to the total (100% by mole) of all constitutional units constituting the component (A1).

In a case where the proportion of the constitutional unit (a4) is equal to or larger than the lower limit value of the preferred range, the effect that is obtained by allowing the constitutional unit (a4) to be contained can be sufficiently achieved. In a case where the proportion of the constitutional unit (a4) is equal to or smaller than the upper limit value of the preferred range, the balance with other constitutional units is obtained easily.

In Regard to Constitutional Unit (St):

The constitutional unit (st) is a constitutional unit derived from styrene or a styrene derivative. A "constitutional unit derived from styrene" means a constitutional unit that is formed by the cleavage of an ethylenic double bond of styrene. A "constitutional unit derived from a styrene derivative" means a constitutional unit (provided that a constitutional unit corresponding to the constitutional unit (a10) is excluded) formed by the cleavage of an ethylenic double bond of a styrene derivative.

The "styrene derivative" means a compound in which at least part of hydrogen atoms of styrene are substituted with a substituent. Examples of the styrene derivative include a derivative in which the hydrogen atom at the α-position of styrene is substituted with a substituent, a derivative in which one or more hydrogen atoms of the benzene ring of styrene are substituted with a substituent, and a derivative in which the hydrogen atom at the α-position of styrene and one or more hydrogen atoms of the benzene ring are substituted with a substituent.

Examples of the substituent that is substituted for the hydrogen atom at the α-position of styrene include an alkyl group having 1 to 5 carbon atoms or a halogenated alkyl group having 1 to 5 carbon atoms.

The alkyl group having 1 to 5 carbon atoms is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group.

The halogenated alkyl group having 1 to 5 carbon atoms is a group obtained by substituting part or all of hydrogen atoms in the alkyl group having 1 to 5 carbon atoms with a halogen atom. The halogen atom is particularly preferably a fluorine atom.

The substituent that is substituted for the hydrogen atom at the α-position of styrene is preferably an alkyl group having 1 to 5 carbon atoms or a fluorinated alkyl group having 1 to 5 carbon atoms, more preferably an alkyl group having 1 to 3 carbon atoms or a fluorinated alkyl group having 1 to 3 carbon atoms, and still more preferably a methyl group from the viewpoint of industrial availability.

Examples of the substituent that is substituted for the hydrogen atom of the benzene ring of styrene include an alkyl group, an alkoxy group, a halogen atom, and a halogenated alkyl group.

The alkyl group as the substituent is preferably an alkyl group having 1 to 5 carbon atoms, and a methyl group, an ethyl group, a propyl group, an n-butyl group, or a tert-butyl group is more preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and still more preferably a methoxy group or an ethoxy group.

The halogen atom as the substituent is preferably a fluorine atom.

Examples of the halogenated alkyl group as the substituent include groups obtained by substituting part or all of hydrogen atoms in the above-described alkyl group with the above-described halogen atom.

The substituent that is substituted for the hydrogen atom of the benzene ring of styrene is preferably an alkyl group having 1 to 5 carbon atoms, more preferably a methyl group or an ethyl group, and still more preferably a methyl group.

The constitutional unit (st) is preferably a constitutional unit derived from styrene or a constitutional unit derived from a styrene derivative in which the hydrogen atom at the α-position of styrene is substituted with an alkyl group having 1 to 5 carbon atoms or a halogenated alkyl group having 1 to 5 carbon atoms, more preferably a constitutional unit derived from styrene, or a constitutional unit derived from a styrene derivative in which the hydrogen atom at the α-position of styrene is substituted with a methyl group, and still more preferably a constitutional unit derived from styrene.

The constitutional unit (st) contained in the component (A1) may be one kind or may be two or more kinds.

In a case where the component (A1) has the constitutional unit (st), the proportion of the constitutional unit (st) is preferably in a range of 1% to 30% by mole and more preferably in a range of 1% to 20% by mole with respect to the total (100% by mole) of all constitutional units constituting the component (A1).

The component (A1) contained in the resist composition may be used alone or in a combination of two or more kinds thereof.

In the resist composition according to the present embodiment, the component (A1) is a resin component that contains the constitutional unit (a01).

Suitable examples of such a component (A1) include a polymeric compound consisting of only a repeating structure of the constitutional unit (a01); a polymeric compound having a repeating structure of the constitutional unit (a01) and the constitutional unit (a10); a polymeric compound having a repeating structure of the constitutional unit (a01), the constitutional unit (a10), and the constitutional unit (a3); a polymeric compound having a repeating structure of the constitutional unit (a01), the constitutional unit (a10), and the constitutional unit (a8); a polymeric compound having a repeating structure of the constitutional unit (a01), the constitutional unit (a10), the constitutional unit (a2), and the constitutional unit (a3); and a polymeric compound having a repeating structure of the constitutional unit (a01) and the constitutional unit (a2). Among them, a polymeric compound having a repeating structure of the constitutional unit (a01) and the constitutional unit (a10) is preferable.

In the polymeric compound consisting of a repeating structure of the constitutional unit (a01) and the constitutional unit (a10), the proportion of the constitutional unit (a01) in the polymeric compound is preferably in a range of 20% to 90% by mole, more preferably in a range of 40% to 80% by mole, and still more preferably in a range of 40% to 70% by mole, with respect to the total (100% by mole) of all constitutional units constituting the polymeric compound.

In addition, the proportion of the constitutional unit (a10) in the polymeric compound is preferably in a range of 10% to 80% by mole, more preferably in a range of 20% to 60% by mole, still more preferably in a range of 30% to 60% by mole, with respect to the total (100% by mole) of all constitutional units constituting the polymeric compound.

In the polymeric compound having a repeating structure of the constitutional unit (a01), the constitutional unit (a10), and the constitutional unit (a8), the proportion of the constitutional unit (a01) in the polymeric compounds is preferably in a range of 20% to 80% by mole, more preferably in a range of 30% to 50% by mole, and still more preferably in a range of 35% to 45% by mole, with respect to the total (100% by mole) of all constitutional units constituting the polymeric compound.

In addition, the proportion of the constitutional unit (a10) in the polymeric compound is preferably in a range of 30% to 70% by mole, more preferably in a range of 40% to 60% by mole, still more preferably in a range of 45% to 55% by mole, with respect to the total (100% by mole) of all constitutional units constituting the polymeric compound.

In addition, the proportion of the constitutional unit (a8) in the polymeric compound is preferably in a range of 1% to 30% by mole, more preferably in a range of 3% to 20% by mole, still more preferably in a range of 5% to 15% by mole, with respect to the total (100% by mole) of all constitutional units constituting the polymeric compound.

In the polymeric compound having a repeating structure of the constitutional unit (a01), the constitutional unit (a10), and the constitutional unit (a3), the proportion of the constitutional unit (a01) in the polymeric compounds is preferably in a range of 20% to 80% by mole, more preferably in a range of 30% to 50% by mole, and still more preferably in a range of 35% to 45% by mole, with respect to the total (100% by mole) of all constitutional units constituting the polymeric compound.

In addition, the proportion of the constitutional unit (a10) in the polymeric compound is preferably in a range of 30% to 70% by mole, more preferably in a range of 40% to 60% by mole, still more preferably in a range of 45% to 55% by mole, with respect to the total (100% by mole) of all constitutional units constituting the polymeric compound.

In addition, the proportion of the constitutional unit (a3) in the polymeric compound is preferably in a range of 1% to 30% by mole, more preferably in a range of 3% to 20% by mole, still more preferably in a range of 5% to 15% by mole, with respect to the total (100% by mole) of all constitutional units constituting the polymeric compound.

In the polymeric compound having a repeating structure of the constitutional unit (a01), the constitutional unit (a10), the constitutional unit (a2), and the constitutional unit (a3), the proportion of the constitutional unit (a01) in the polymeric compound is preferably in a range of 20% to 80% by mole, more preferably in a range of 30% to 50% by mole, and still more preferably in a range of 35% to 45% by mole, with respect to the total (100% by mole) of all constitutional units constituting the polymeric compound.

In addition, the proportion of the constitutional unit (a10) in the polymeric compound is preferably in a range of 10% to 50% by mole, more preferably in a range of 20% to 40% by mole, still more preferably in a range of 25% to 35% by mole, with respect to the total (100% by mole) of all constitutional units constituting the polymeric compound.

In addition, the proportion of the constitutional unit (a2) in the polymeric compound is preferably in a range of 1% to 30% by mole, more preferably in a range of 10% to 30% by mole, still more preferably in a range of 15% to 25% by mole, with respect to the total (100% by mole) of all constitutional units constituting the polymeric compound.

In addition, the proportion of the constitutional unit (a3) in the polymeric compound is preferably in a range of 1% to 30% by mole, more preferably in a range of 3% to 20% by mole, still more preferably in a range of 5% to 15% by mole, with respect to the total (100% by mole) of all constitutional units constituting the polymeric compound.

The component (A1) can be produced by dissolving, in a polymerization solvent, each monomer from which the constitutional unit is derived, adding thereto a radical polymerization initiator such as azobisisobutyronitrile (AIBN) or dimethyl azobisisobutyrate (for example, V-601) to carry out polymerization.

Alternatively, the component (A1) can be produced by dissolving, in a polymerization solvent, a monomer from which the constitutional unit (a01) is derived and, as necessary, a monomer (for example, a compound in which a hydroxyl group of a monomer from which the constitutional unit (a10) is derived is protected) from which a constitutional unit other than the constitutional unit (a01) is derived, and adding thereto a radical polymerization initiator as described above to carry out polymerization and then carrying out a deprotection reaction.

Further, a —$C(CF_3)_2$—OH group may be introduced into the terminal of the component (A1) during the polymerization using a chain transfer agent such as HS—$CH_2$—$CH_2$—$CH_2$—$C(CF_3)_2$—OH in combination. As described above, a copolymer into which a hydroxyalkyl group, formed by substitution of part of hydrogen atoms in the alkyl group with fluorine atoms, has been introduced is effective for reducing development defects and reducing line edge roughness (LER: uneven irregularities of a line side wall).

The weight average molecular weight (Mw) (based on the polystyrene-equivalent value determined by gel permeation chromatography (GPC)) of the component (A1), which is not particularly limited, is preferably in a range of 1,000 to 50,000, more preferably in a range of 2,000 to 30,000, and still more preferably in a range of 3,000 to 20,000.

In a case where Mw of the component (A1) is equal to or smaller than the upper limit value of this preferred range, the solubility in the resist solvent is sufficient for use in the resist. On the other hand, in a case where Mw of the component (A1) is equal to or larger than the lower limit value of this preferred range, the dry etching resistance and the cross-sectional shape of the resist pattern become excellent.

Further, the polydispersity (Mw/Mn) of the component (A1) is not particularly limited; however, it is preferably in a range of 1.0 to 4.0, more preferably in a range of 1.0 to 3.0, and particularly preferably in a range of 1.0 to 2.0. Mn represents the number average molecular weight.

In Regard to Component (A2)

In the resist composition according to the present embodiment, a base material component (hereinafter, referred to as a "component (A2)") that exhibits changed solubility in a developing solution under action of acid, which does not correspond to the component (A1), may be used in combination as the component (A).

The component (A2) is not particularly limited and may be freely selected and used from a large number of base material components for the chemically amplified resist composition, which are known in the related art.

As the component (A2), a polymeric compound or a low molecular weight compound may be used alone or in a combination of two or more kinds thereof.

The proportion of the component (A1) in the component (A) is preferably 25% by mass or more, more preferably 50% by mass or more, still more preferably 75% by mass or more, and may be 100% by mass with respect to the total mass of the component (A). In a case where the proportion is 25% by mass or more, a resist pattern having various excellent lithography characteristics such as high sensitivity, resolution, and roughness amelioration can be easily formed.

The content of the component (A) in the resist composition according to the present embodiment may be adjusted depending on the resist film thickness to be formed.

<Other Components>

The resist composition according to the present embodiment may further contain other components in addition to the component (A) described above. Examples of the other components include a component (B), a component (D), a component (E), a component (F), and a component (S), which are described below.

<<Acid Generator Component (B)>>

The resist composition according to the present embodiment may further contain an acid generator component (B) (hereinafter, referred to as a "component (B)") that generates acid upon exposure, in addition to the component (A).

The component (B) is not particularly limited, and those which have been proposed so far as an acid generator for a chemically amplified resist composition can be used.

Examples of these acid generators are numerous and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl) diazomethanes; nitrobenzyl sulfonate-based acid generators; iminosulfonate-based acid generators; and disulfonate-based acid generators.

Examples of the onium salt-based acid generator include a compound represented by General Formula (b-1) (hereinafter, also referred to as a "component (b-1)"), a compound represented by General Formula (b-2) (hereinafter, also referred to as a "component (b-2)"), and a compound represented by General Formula (b-3) (hereinafter, also referred to as a "component (b-3)").

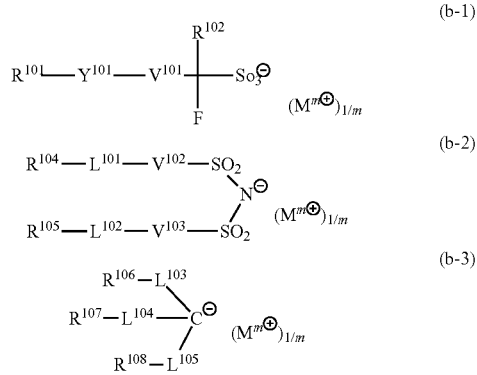

[In the formulae, $R^{101}$ and $R^{104}$ to $R^{108}$ each independently represent a cyclic group which may have a substituent, a chain alkyl group which may have a substituent, or a chain alkenyl group which may have a substituent. $R^{104}$ and $R^{105}$ may be bonded to each other to form a ring structure. $R^{102}$ represents a fluorinated alkyl group having 1 to 5 carbon atoms or a fluorine atom. $Y^{101}$ represents a divalent linking group containing an oxygen atom or a single bond. $V^{101}$ to $V^{103}$ each independently represent a single bond, an alkylene group, or a fluorinated alkylene group. $L^{101}$ and $L^{102}$ each independently represent a single bond or an oxygen atom. $L^{103}$ to $L^{105}$ each independently represent a single bond, —CO—, or —SO$_2$—. m represents an integer of 1 or more, and $M^{m+}$ represents an m-valent onium cation.]

{Anion Moiety}
Anion in Component (b-1)

In General Formula (b-1), $R^{101}$ represents a cyclic group which may have a substituent, a chain alkyl group which may have a substituent, or a chain alkenyl group which may have a substituent.

Cyclic Group which May have Substituent:

The cyclic group is preferably a cyclic hydrocarbon group, and the cyclic hydrocarbon group may be an aromatic hydrocarbon group or an aliphatic hydrocarbon group. The aliphatic hydrocarbon group indicates a hydrocarbon group that has no aromaticity. The aliphatic hydrocarbon group may be saturated or unsaturated. In general, it is preferable that the aliphatic hydrocarbon group is saturated.

The aromatic hydrocarbon group as $R^{101}$ is a hydrocarbon group having an aromatic ring. The aromatic hydrocarbon group preferably has 3 to 30 carbon atoms, more preferably 5 to 30, still more preferably 5 to 20, particularly preferably 6 to 15, and most preferably 6 to 10. However, the number of carbon atoms in a substituent is not included in the number of carbon atoms.

Specific examples of the aromatic ring contained in the aromatic hydrocarbon group as $R^{101}$ include benzene, fluorene, naphthalene, anthracene, phenanthrene, biphenyl, or an aromatic heterocyclic ring obtained by substituting part of carbon atoms constituting these aromatic rings with a hetero atom. Examples of the hetero atom in the aromatic heterocyclic rings include an oxygen atom, a sulfur atom, and a nitrogen atom.

Specific examples of the aromatic hydrocarbon group as $R^{101}$ include a group obtained by removing one hydrogen atom from the above-described aromatic ring (an aryl group; for example, a phenyl group or a naphthyl group) and a group obtained by substituting one hydrogen atom in the aromatic ring with an alkylene group (an arylalkyl group such as a benzyl group, a phenethyl group, a 1-naphthylmethyl group, a 2-naphthylmethyl group, 1-naphthylethyl group, or a 2-naphthylethyl group). The alkylene group (an alkyl chain in the arylalkyl group) preferably has 1 to 4 carbon atoms, more preferably 1 or 2 carbon atoms, and particularly preferably 1 carbon atom.

Examples of the cyclic aliphatic hydrocarbon group as $R^{101}$ include aliphatic hydrocarbon groups containing a ring in the structure thereof.

Examples of the aliphatic hydrocarbon group containing a ring in the structure thereof include an alicyclic hydrocarbon group (a group obtained by removing one hydrogen atom from an aliphatic hydrocarbon ring), a group obtained by bonding an alicyclic hydrocarbon group to the terminal of a linear or branched aliphatic hydrocarbon group, and a group obtained by interposing an alicyclic hydrocarbon group is interposed in a linear or branched aliphatic hydrocarbon group.

The alicyclic hydrocarbon group preferably has 3 to 20 carbon atoms and more preferably 3 to 12 carbon atoms.

The alicyclic hydrocarbon group may be a polycyclic group or a monocyclic group. The monocyclic alicyclic hydrocarbon group is preferably a group obtained by removing one or more hydrogen atoms from a monocycloalkane. The monocycloalkane preferably has 3 to 6 carbon atoms, and specific examples thereof include cyclopentane and cyclohexane. The polycyclic alicyclic hydrocarbon group is preferably a group obtained by removing one or more hydrogen atoms from a polycycloalkane, and the polycycloalkane preferably has 7 to 30 carbon atoms. Among the above, the polycycloalkane is more preferably a polycycloalkane having a bridged ring-based polycyclic skeleton, such as adamantane, norbornane, isobornane, tricyclodecane, or tetracyclododecane; or a polycycloalkane having a condensed ring-based polycyclic skeleton, such as a cyclic group having a steroid skeleton.

Among them, the cyclic aliphatic hydrocarbon group as $R^{101}$ is preferably a group obtained by removing one or more hydrogen atoms from a monocycloalkane or a polycycloalkane, more preferably a group obtained by removing one hydrogen atom from a polycycloalkane, particularly preferably an adamantyl group or a norbornyl group, and most preferably an adamantyl group.

The linear aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and most preferably 1 to 3 carbon atoms. The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group which may be bonded to the alicyclic hydrocarbon group preferably has 2 to 10 carbon atoms, more preferably 3 to 6 carbon atoms, still more preferably 3 or 4 carbon atoms, and most preferably 3 carbon atoms. The branched aliphatic hydrocarbon group is preferably a branched alkylene group, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

The cyclic hydrocarbon group as $R^{101}$ may contain a hetero atom such as a heterocyclic ring. Specific examples thereof include lactone-containing cyclic groups each represented by General Formulae (a2-r-1) to (a2-r-7), —$SO_2$—-containing cyclic groups each represented by General Formulae (a5-r-1) to (a5-r-4), and other heterocyclic groups each represented by Chemical Formulae (r-hr-1) to (r-hr-16). In the formulae, * represents a bonding site that is bonded to $Y^{101}$ in General Formula (b-1).

(r-hr-1)

(r-hr-2)

(r-hr-3)

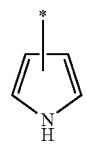

(r-hr-4)

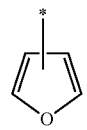

(r-hr-5)

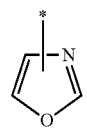

(r-hr-6)

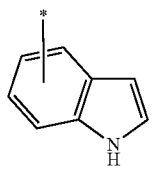

(r-hr-7)

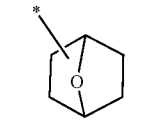

(r-hr-8)

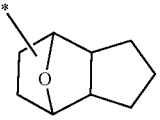

(r-hr-9)

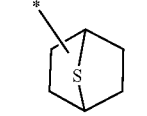

(r-hr-10)

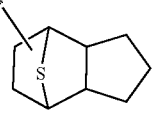

(r-hr-11)

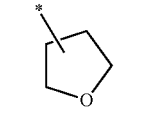

(r-hr-12)

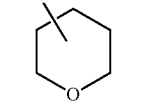

(r-hr-13)

(r-hr-14)

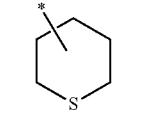

(r-hr-15)

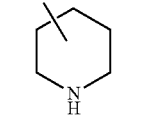

(r-hr-16)

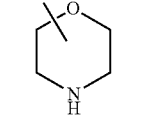

Examples of the substituent of the cyclic group as $R^{101}$ include an alkyl group, an alkoxy group, a halogen atom, a halogenated alkyl group, a hydroxyl group, a carbonyl group, and a nitro group.

The alkyl group as the substituent is preferably an alkyl group having 1 to 5 carbon atoms, and a methyl group, an ethyl group, a propyl group, an n-butyl group, or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom for the substituent include a fluorine atom, a chlorine atom, a bromine atom, and an iodine atom, and a fluorine atom is preferable.

Examples of the halogenated alkyl group as the substituent include a group obtained by substituting part or all of hydrogen atoms in an alkyl group having 1 to 5 carbon atoms such as a methyl group, an ethyl group, a propyl group, an n-butyl group, or a tert-butyl group, with the above-described halogen atom.

The carbonyl group as the substituent is a group that substitutes a methylene group (—$CH_2$—) constituting the cyclic hydrocarbon group.

The cyclic hydrocarbon group as $R^{101}$ may be a condensed cyclic group containing a condensed ring in which an aliphatic hydrocarbon ring and an aromatic ring are condensed. Examples of the condensed ring include a condensed ring in which one or more aromatic rings are condensed with a polycycloalkane having a bridged ring-based polycyclic skeleton. Specific examples of the bridged ring-based polycycloalkane include bicycloalkanes such as bicyclo[2.2.1]heptane (norbornane) and bicyclo[2.2.2]octane. The condensed cyclic group is preferably a group containing a condensed ring, in which two or three aromatic rings are condensed with a bicycloalkane, and more preferably a group containing a condensed ring, in which two or three aromatic rings are condensed with bicyclo[2.2.2]octane. Specific examples of the condensed cyclic group as $R^{101}$ include those represented by General Formulae (r-br-1) to (r-br-2). In the formulae, * represents a bonding site that is bonded to $Y^{101}$ in General Formula (b-1).

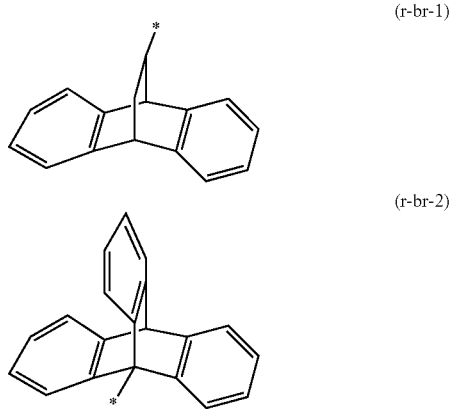

(r-br-1)

(r-br-2)

Examples of the substituent which may be contained in the condensed cyclic group as $R^{101}$ include an alkyl group, an alkoxy group, a halogen atom, a halogenated alkyl group, a hydroxyl group, a carbonyl group, a nitro group, an aromatic hydrocarbon group, and an alicyclic hydrocarbon group.

Examples of the alkyl group, the alkoxy group, the halogen atom, and the halogenated alkyl group, as the substituent of the condensed cyclic group, include the same ones as those described as the substituent of the cyclic group as $R^{101}$.

Examples of the aromatic hydrocarbon group as the substituent of the condensed cyclic group include a group obtained by removing one hydrogen atom from the above-described aromatic ring (an aryl group; for example, a phenyl group or a naphthyl group), a group obtained by substituting one hydrogen atom in the aromatic ring with an alkylene group (for example, an arylalkyl group such as a benzyl group, a phenethyl group, a 1-naphthylmethyl group, a 2-naphthylmethyl group, 1-naphthylethyl group, or a 2-naphthylethyl group), and heterocyclic groups each represented by General Formulae (r-hr-1) to (r-hr-6).

Examples of the alicyclic hydrocarbon group as the substituent of the condensed cyclic group include a group obtained by removing one hydrogen atom from a monocycloalkane such as cyclopentane or cyclohexane; a group obtained by removing one hydrogen atom from a polycycloalkane such as adamantane, norbornane, isobornane, tricyclodecane, or tetracyclododecane; lactone-containing cyclic groups each represented by General Formulae (a2-r-1) to (a2-r-7); —$SO_2$—-containing cyclic groups each represented by General Formulae (a5-r-1) to (a5-r-4); and heterocyclic groups each represented by General Formulae (r-hr-7) to (r-hr-16).

Chain Alkyl Group which May have Substituent:

The chain alkyl group as $R^{101}$ may be linear or branched.

The linear alkyl group preferably has 1 to 20 carbon atoms, more preferably 1 to 15 carbon atoms, and most preferably 1 to 10 carbon atoms.

The branched alkyl group preferably has 3 to 20 carbon atoms, more preferably 3 to 15 carbon atoms, and most preferably 3 to 10 carbon atoms. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Chain Alkenyl Group which May have Substituent:

A chain alkenyl group as $R^{101}$ may be linear or branched, and the chain alkenyl group preferably has 2 to 10 carbon atoms, more preferably 2 to 5 carbon atoms, still more preferably 2 to 4 carbon atoms, and particularly preferably 3 carbon atoms. Examples of the linear alkenyl group include a vinyl group, a propenyl group (an allyl group), and a butynyl group. Examples of the branched alkenyl group include a 1-methylvinyl group, a 2-methylvinyl group, a 1-methylpropenyl group, and a 2-methylpropenyl group.

Among the above, the chain alkenyl group is preferably a linear alkenyl group, more preferably a vinyl group or a propenyl group, and particularly preferably a vinyl group.

Examples of the substituent in the chain alkyl group or alkenyl group as $R^{101}$, include an alkoxy group, a halogen atom, a halogenated alkyl group, a hydroxyl group, a carbonyl group, a nitro group, an amino group, and a cyclic group as $R^{101}$.

Among the above, $R^{101}$ is preferably a cyclic group which may have a substituent and more preferably a cyclic hydrocarbon group which may have a substituent. More specific examples of the cyclic hydrocarbon group preferably include a phenyl group, a naphthyl group, a group obtained by removing one or more hydrogen atoms from a polycycloalkane, lactone-containing cyclic groups each represented by any one of General Formulae (a2-r-1) to (a2-r-7), and —$SO_2$—-containing cyclic groups each represented by any one of General Formulae (a5-r-1) to (a5-r-4).

In General Formula (b-1), $Y^{101}$ represents a single bond or a divalent linking group containing an oxygen atom.

In a case where $Y^{101}$ represents a divalent linking group containing an oxygen atom, $Y^{101}$ may contain an atom other than the oxygen atom. Examples of the atom other than the oxygen atom include a carbon atom, a hydrogen atom, a sulfur atom, and a nitrogen atom.

Examples of divalent linking groups containing an oxygen atom include non-hydrocarbon-based oxygen atom-containing linking groups such as an oxygen atom (an ether bond; —O—), an ester bond (—C(=O)—O—), an oxycarbonyl group (—O—C(=O)—), an amide bond (—C(=O)—NH—), a carbonyl group (—C(=O)—), or a carbonate bond (—O—C(=O)—O—); and combinations of the above-described non-hydrocarbon-based oxygen atom-containing linking groups with an alkylene group. Furthermore, a sulfonyl group (—$SO_2$—) may be linked to the combination. Examples of such a divalent linking group containing an oxygen atom include linking groups each represented by General Formulae (y-a1-1) to (y-a1-7) shown below. In General Formulae (y-a1-1) to (y-a1-7), the one that is bonded to $R^{101}$ in General Formula (b-1) is $V'^{101}$ in General Formulae (y-a1-1) to (y-a1-7).

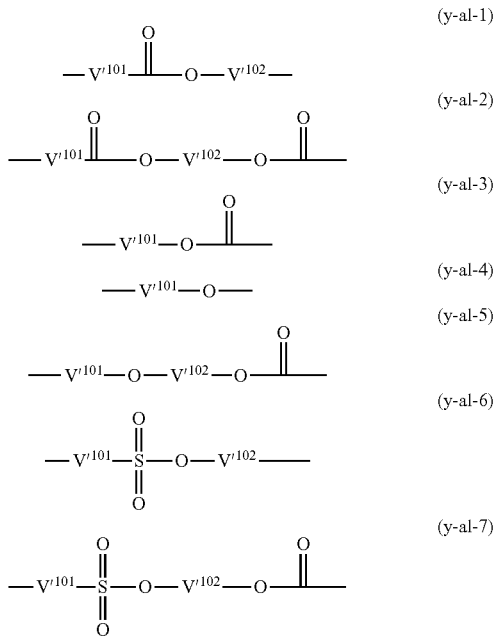

[In the formulae, $V'^{101}$ represents a single bond or an alkylene group having 1 to 5 carbon atoms, and $V'^{102}$ represents a divalent saturated hydrocarbon group having 1 to 30 carbon atoms.]

The divalent saturated hydrocarbon group as $V'^{102}$ is preferably an alkylene group having 1 to 30 carbon atoms, more preferably an alkylene group having 1 to 10 carbon atoms, and still more preferably an alkylene group having 1 to 5 carbon atoms.

The alkylene group as $V'^{101}$ and $V'^{102}$ may be a linear alkylene group or a branched alkylene group, and a linear alkylene group is preferable.

Specific examples of the alkylene group as $V'^{101}$ and $V'^{102}$ include a methylene group [—$CH_2$—]; an alkylmethylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, or —$C(CH_2CH_3)_2$—; an ethylene group [—$CH_2CH_2$—]; an alkylethylene group such as —$CH(CH_3)CH_2$—, —$CH(CH_3)CH(CH_3)$—, —$C(CH_3)_2CH_2$—, or —$CH(CH_2CH_3)CH_2$—; a trimethylene group (n-propylene group) [—$CH_2CH_2CH_2$—]; an alkyltrimethylene group such as —$CH(CH_3)CH_2CH_2$— or —$CH_2CH(CH_3)CH_2$—; a tetramethylene group [—$CH_2CH_2CH_2CH_2$—]; an alkyltetramethylene group such as —$CH(CH_3)CH_2CH_2CH_2$—, or —$CH_2CH(CH_3)CH_2CH_2$—; and a pentamethylene group [—$CH_2CH_2CH_2CH_2CH_2$—].

Further, part of methylene groups in the alkylene group as $V'^{101}$ and $V'^{102}$ may be substituted with a divalent aliphatic cyclic group having 5 to 10 carbon atoms. The aliphatic cyclic group is preferably a divalent group obtained by removing one hydrogen atom from the cyclic aliphatic hydrocarbon group (a monocyclic aliphatic hydrocarbon group or a polycyclic aliphatic hydrocarbon group) as $R^{r3}$ in General Formula (a1-r-1), and a cyclohexylene group, a 1,5-adamantylene group, or a 2,6-adamantylene group is more preferable.

$Y^{101}$ preferably represents a divalent linking group containing an ester bond or a divalent linking group containing an ether bond and more preferably linking groups each represented by General Formulae (y-a1-1) to (y-a1-5).

In General Formula (b-1), $V^{101}$ represents a single bond, an alkylene group, or a fluorinated alkylene group. The alkylene group and the fluorinated alkylene group as $V^{101}$ preferably have 1 to 4 carbon atoms. Examples of the fluorinated alkylene group as $V^{101}$ include a group obtained by substituting part or all of hydrogen atoms in an alkylene group as $V^{101}$ with a fluorine atom. Among these examples, as $V^{101}$, a single bond or a fluorinated alkylene group having 1 to 4 carbon atoms is preferable.

In General Formula (b-1), $R^{102}$ represents a fluorine atom or a fluorinated alkyl group having 1 to 5 carbon atoms. $R^{102}$ preferably represents a fluorine atom or a perfluoroalkyl group having 1 to 5 carbon atoms and more preferably a fluorine atom.

In a case where $Y^{101}$ represents a single bond, specific examples of the anion moiety represented by General Formula (b-1) include a fluorinated alkylsulfonate anion such as a trifluoromethanesulfonate anion or a perfluorobutanesulfonate anion; and in a case where $Y^{101}$ represents a divalent linking group containing an oxygen atom, specific examples thereof include an anion represented by any one of General Formulae (an-1) to (an-3) shown below.

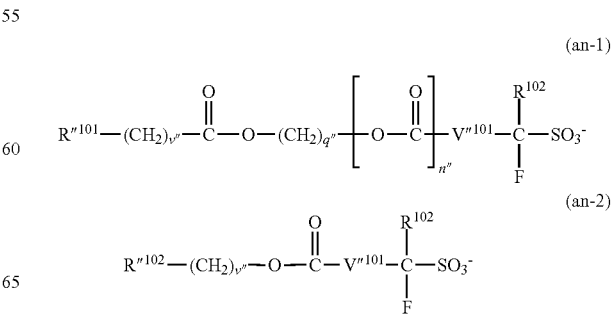

-continued (an-3)

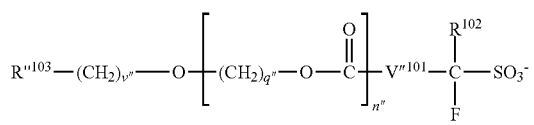

[In the formula, $R'''^{101}$ represents an aliphatic cyclic group which may have a substituent, monovalent heterocyclic groups each represented by Chemical Formulae (r-hr-1) to (r-hr-6), a condensed cyclic group represented by General Formula (r-br-1) or (r-br-2), and a chain alkyl group which may have a substituent. $R'''^{102}$ is an aliphatic cyclic group which may have a substituent, a condensed cyclic group represented by General Formula (r-br-1) or (r-br-2), lactone-containing cyclic groups each represented by General Formulae (a2-r-1), (a2-r-3) to (a2-r-7), or —$SO_2$—-containing cyclic groups each represented by General Formulae (a5-r-1) to (a5-r-4). $R'''^{103}$ represents an aromatic cyclic group which may have a substituent, an aliphatic cyclic group which may have a substituent, or a chain alkenyl group which may have a substituent. $V'''^{101}$ represents a single bond, an alkylene group having 1 to 4 carbon atoms, or a fluorinated alkylene group having 1 to 4 carbon atoms. $R^{102}$ represents a fluorine atom or a fluorinated alkyl group having 1 to 5 carbon atoms. Each v″ independently represents an integer in a range of 0 to 3, each q″ independently represents an integer in a range of 0 to 20, and n″ represents 0 or 1.]

The aliphatic cyclic group as $R'''^{101}$, $R'''^{102}$, and $R'''^{103}$ which may have a substituent is preferably the group exemplified as the cyclic aliphatic hydrocarbon group as $R^{101}$ in General Formula (b-1). Examples of the substituent include the same one as the substituent that may be substituted for the cyclic aliphatic hydrocarbon group as $R^{101}$ in General Formula (b-1).

The aromatic cyclic group which may have a substituent, as $R'''^{103}$, is preferably the group exemplified as the aromatic hydrocarbon group for the cyclic hydrocarbon group as $R'^{101}$ in General Formula (b-1). Examples of the substituent include the same one as the substituent that may be substituted for the aromatic hydrocarbon group as $R^{101}$ in General Formula (b-1).

The chain alkyl group as $R'''^{101}$, which may have a substituent, is preferably the group exemplified as the chain alkyl group as $R^{101}$ in General Formula (b-1).

The chain alkenyl group as $R'''^{103}$, which may have a substituent, is preferably the group exemplified as the chain alkenyl group as $R^{101}$ in General Formula (b-1).

Anion in Component (b-2)

In General Formula (b-2), $R^{104}$ and $R^{105}$ each independently represent a cyclic group which may have a substituent, a chain alkyl group which may have a substituent, or a chain alkenyl group which may have a substituent, and examples thereof each include the same one as $R^{101}$ in General Formula (b-1). However, $R^{104}$ and $R^{105}$ may be bonded to each other to form a ring.

$R^{104}$ and $R^{105}$ are preferably a chain alkyl group which may have a substituent and more preferably a linear or branched alkyl group or a linear or branched fluorinated alkyl group.

The chain alkyl group preferably has 1 to 10 carbon atoms, more preferably 1 to 7 carbon atoms, and still more preferably 1 to 3 carbon atoms. It is preferable that the number of carbon atoms in the chain alkyl group as $R^{104}$ and $R^{105}$ is small since the solubility in a resist solvent is also excellent in this range of the number of carbon atoms. Further, in the chain alkyl group as $R^{104}$ and $R^{105}$, it is preferable that the number of hydrogen atoms substituted with a fluorine atom is large since the acid strength increases and the transparency to high energy radiation of 250 nm or less or an electron beam is improved. The proportion of fluorine atoms in the chain alkyl group, that is, the fluorination rate is preferably in a range of 70% to 100% and more preferably in a range of 90% to 100%, and it is most preferable that the chain alkyl group is a perfluoroalkyl group obtained substituting all hydrogen atoms with a fluorine atom.

In General Formula (b-2), $V^{102}$ and $V^{103}$ each independently represent a single bond, an alkylene group, or a fluorinated alkylene group, and examples thereof include the same one as $V^{101}$ in General Formula (b-1).

In General Formula (b-2), $L^{101}$ and $L^{102}$ each independently represent a single bond or an oxygen atom.

Anion in Component (b-3)

In General Formula (b-3), $R^{106}$ to $R^{108}$ each independently represent a cyclic group which may have a substituent, chain alkyl group which may have a substituent, or a chain alkenyl group which may have a substituent, and examples thereof include the same one as $R^{101}$ in General Formula (b-1).

In General Formula (b-3), $L^{103}$ to $L^{105}$ each independently represent a single bond, —CO—, or —$SO_2$—.

Among the above, the anion moiety of the component (B) is preferably an anion of the component (b-1). Among these, an anion represented by any one of General Formulae (an-1) to (an-3) is more preferable, an anion represented by any one of General Formula (an-1) or (an-2) is still more preferable, and an anion represented by General Formula (an-2) is particularly preferable.

{Cation Moiety}

In Formulae (b-1), (b-2), and (b-3) shown above, $M^{m+}$ represents an m-valent onium cation. Among them, a sulfonium cation and an iodonium cation are preferable.

m represents an integer of 1 or more.

Preferred examples of the cation moiety $((M^{m+})_{1/m})$ include organic cations each represented by General Formulae (ca-1) to (ca-5).

(ca-1)

(ca-2)

$R^{204}—I^+—R^{205}$ (ca-3)

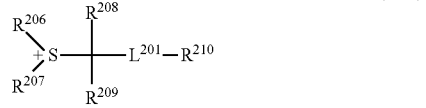

(ca-4)

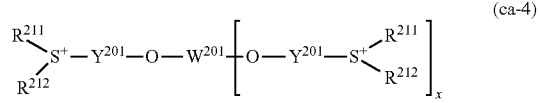

(ca-5)

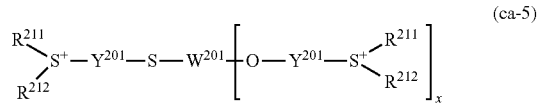

[In the formula, $R^{201}$ to $R^{207}$, $R^{211}$ and $R^{212}$ each independently represent an aryl group, an alkyl group, or an alkenyl group, each of which may have a substituent. $R^{201}$ to $R^{203}$, $R^{206}$, and $R^{207}$, or $R^{211}$ and $R^{212}$ may be bonded to each other to form a ring together with a sulfur atom in the formula. $R^{208}$ and $R^{209}$ each independently represent a hydrogen atom or an alkyl group having 1 to 5 carbon atoms. $R^{210}$ represents an aryl group which may have a substituent, an alkyl group which may have a substituent, an alkenyl group which may have a substituent, or a —$SO_2$—-containing cyclic group which may have a substituent. $L^{201}$ represents —C(=O)— or —C(=O)—O—. Each $Y^{201}$ independently represents an arylene group, an alkylene group, or an alkenylene group. x represents 1 or 2. $W^{201}$ represents an (x+1)-valent linking group.]

In General Formulae (ca-1) to (ca-5), examples of the aryl group as $R^{201}$ to $R^{207}$, $R^{211}$, and $R^{212}$ include an unsubstituted aryl group having 6 to 20 carbon atoms, and a phenyl group or a naphthyl group is preferable.

The alkyl group as $R^{201}$ to $R^{207}$, $R^{211}$ and $R^{212}$ is a chain or cyclic alkyl group and preferably has 1 to 30 carbon atoms.

The alkenyl group as $R^{201}$ to $R^{207}$, $R^{211}$, and $R^{212}$ preferably has 2 to 10 carbon atoms.

Examples of the substituent which may be contained in $R^{201}$ to $R^{207}$ and $R^{210}$ to $R^{212}$ include an alkyl group, a halogen atom, a halogenated alkyl group, a carbonyl group, a cyano group, an amino group, an aryl group, and groups each represented by General Formulae (ca-r-1) to (ca-r-7) shown below.

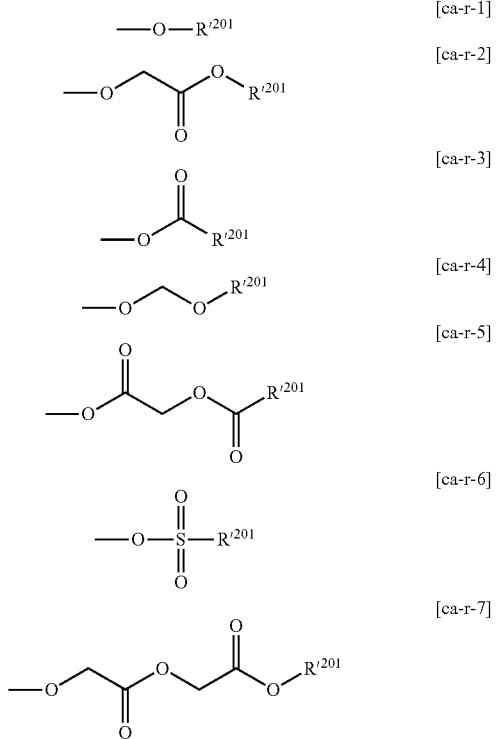

[In the formulae, each $R'^{201}$ independently represents a hydrogen atom, a cyclic group which may have a substituent, a chain alkyl group which may have a substituent, or a chain alkenyl group which may have a substituent.]

Cyclic Group which May have Substituent:

The cyclic group is preferably a cyclic hydrocarbon group, and the cyclic hydrocarbon group may be an aromatic hydrocarbon group or an aliphatic hydrocarbon group. The aliphatic hydrocarbon group indicates a hydrocarbon group that has no aromaticity. The aliphatic hydrocarbon group may be saturated or unsaturated. In general, it is preferable that the aliphatic hydrocarbon group is saturated.

The aromatic hydrocarbon group as $R'^{201}$ is a hydrocarbon group having an aromatic ring. The aromatic hydrocarbon group preferably has 3 to 30 carbon atoms, more preferably 5 to 30 carbon atoms, still more preferably 5 to 20 carbon atoms, particularly preferably 6 to 15 carbon atoms, and most preferably 6 to 10 carbon atoms. Here, the number of carbon atoms in a substituent is not included in the number of carbon atoms.

Specific examples of the aromatic ring contained in the aromatic hydrocarbon group as $R'^{201}$ include benzene, fluorene, naphthalene, anthracene, phenanthrene, biphenyl, or an aromatic heterocyclic ring obtained by substituting part of carbon atoms constituting these aromatic rings with a hetero atom. Examples of the hetero atom in the aromatic heterocyclic rings include an oxygen atom, a sulfur atom, and a nitrogen atom.

Specific examples of the aromatic hydrocarbon group as $R'^{201}$ include a group obtained by removing one hydrogen atom from the above-described aromatic ring (an aryl group; for example, a phenyl group or a naphthyl group) and a group obtained by substituting one hydrogen atom in the aromatic ring with an alkylene group (for example, an arylalkyl group such as a benzyl group, a phenethyl group, a 1-naphthylmethyl group, a 2-naphthylmethyl group, 1-naphthylethyl group, or a 2-naphthylethyl group). The alkylene group (an alkyl chain in the arylalkyl group) preferably has 1 to 4 carbon atoms, more preferably 1 or 2 carbon atoms, and particularly preferably 1 carbon atom.

Examples of the cyclic aliphatic hydrocarbon group as $R'^{201}$ include aliphatic hydrocarbon groups containing a ring in the structure thereof.

Examples of the aliphatic hydrocarbon group containing a ring in the structure thereof include an alicyclic hydrocarbon group (a group obtained by removing one hydrogen atom from an aliphatic hydrocarbon ring), a group obtained by bonding an alicyclic hydrocarbon group to the terminal of a linear or branched aliphatic hydrocarbon group, and a group obtained by interposing an alicyclic hydrocarbon group is interposed in a linear or branched aliphatic hydrocarbon group.

The alicyclic hydrocarbon group preferably has 3 to 20 carbon atoms and more preferably 3 to 12 carbon atoms.

The alicyclic hydrocarbon group may be a polycyclic group or a monocyclic group. The monocyclic alicyclic hydrocarbon group is preferably a group obtained by removing one or more hydrogen atoms from a monocycloalkane. The monocycloalkane preferably has 3 to 6 carbon atoms, and specific examples thereof include cyclopentane and cyclohexane. The polycyclic alicyclic hydrocarbon group is preferably a group obtained by removing one or more hydrogen atoms from a polycycloalkane, and the polycycloalkane preferably has 7 to 30 carbon atoms. Among the above, the polycycloalkane is more preferably a polycycloalkane having a bridged ring-based polycyclic skeleton, such as adamantane, norbornane, isobornane, tricyclodecane, or tetracyclododecane; or a polycycloalkane having a condensed ring-based polycyclic skeleton, such as a cyclic group having a steroid skeleton.

Among them, the cyclic aliphatic hydrocarbon group as $R'^{201}$ is preferably a group obtained by removing one or more hydrogen atoms from a monocycloalkane or a polycycloalkane, more preferably a group obtained by removing one hydrogen atom from a polycycloalkane, particularly preferably an adamantyl group or a norbornyl group, and most preferably an adamantyl group.

The linear or branched aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and particularly preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group is preferably a branched alkylene group, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

The cyclic hydrocarbon group as $R'^{201}$ may contain a hetero atom such as a heterocyclic ring. Specific examples thereof include lactone-containing cyclic groups each represented by General Formulae (a2-r-1) to (a2-r-7), —$SO_2$—-containing cyclic groups each represented by General Formulae (a5-r-1) to (a5-r-4), and other heterocyclic groups each represented by Chemical Formulae (r-hr-1) to (r-hr-16).

Examples of the substituent of the cyclic group as $R'^{201}$ include an alkyl group, an alkoxy group, a halogen atom, a halogenated alkyl group, a hydroxyl group, a carbonyl group, and a nitro group.

The alkyl group as the substituent is preferably an alkyl group having 1 to 5 carbon atoms, and a methyl group, an ethyl group, a propyl group, an n-butyl group, or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

The halogen atom as the substituent is preferably a fluorine atom.

Examples of the above-described halogenated alkyl group as the substituent include a group obtained by substituting part or all of hydrogen atoms in an alkyl group having 1 to 5 carbon atoms such as a methyl group, an ethyl group, a propyl group, an n-butyl group, or a tert-butyl group with the above-described halogen atom.

The carbonyl group as the substituent is a group that substitutes a methylene group (—$CH_2$—) constituting the cyclic hydrocarbon group.

Chain Alkyl Group which May have Substituent:
The chain alkyl group as $R'^{201}$ may be linear or branched.

The linear alkyl group preferably has 1 to 20 carbon atoms, more preferably 1 to 15 carbon atoms, and most preferably 1 to 10 carbon atoms.

The branched alkyl group preferably has 3 to 20 carbon atoms, more preferably 3 to 15 carbon atoms, and most preferably 3 to 10 carbon atoms. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Chain Alkenyl Group which May have Substituent:
Such a chain alkenyl group as $R'^{201}$ may be linear or branched, preferably has 2 to 10 carbon atoms, more preferably 2 to 5 carbon atoms, still more preferably 2 to 4 carbon atoms, and particularly preferably 3 carbon atoms. Examples of the linear alkenyl group include a vinyl group, a propenyl group (an allyl group), and a butynyl group. Examples of the branched alkenyl group include a 1-methylvinyl group, a 2-methylvinyl group, a 1-methylpropenyl group, and a 2-methylpropenyl group.

Among the above, the chain alkenyl group is preferably a linear alkenyl group, more preferably a vinyl group or a propenyl group, and particularly preferably a vinyl group.

Examples of the substituent in the chain alkyl group or alkenyl group as $R'^{201}$, an alkoxy group, a halogen atom, a halogenated alkyl group, a hydroxyl group, a carbonyl group, a nitro group, an amino group, a cyclic group as $R'^{201}$ or the like may be used.

As the cyclic group which may have a substituent, the chain alkyl group which may have a substituent, or the chain alkenyl group which may have a substituent, as $R'^{201}$, a group that is the same as the acid dissociable group represented by above-described General Formula (a1-r-2) can be mentioned as the cyclic group which may have a substituent or the chain alkyl group which may have a substituent, in addition to the groups described above.

Among them, $R'^{201}$ is preferably a cyclic group which may have a substituent and more preferably a cyclic hydrocarbon group which may have a substituent. More specific examples thereof preferably include a phenyl group, a naphthyl group, a group obtained by removing one or more hydrogen atoms from a polycycloalkane, lactone-containing cyclic groups each represented by any one of General Formulae (a2-r-1) to (a2-r-7), and —$SO_2$—-containing cyclic groups each represented by any one of General Formulae (a5-r-1) to (a5-r-4).

In General Formulae (ca-1) to (ca-5), in a case where $R^{201}$ to $R^{203}$, $R^{206}$ and $R^{207}$, or $R^{211}$ and $R^{212}$ are bonded to each other to form a ring together with a sulfur atom in the formula, these groups may be bonded to each other via a hetero atom such as a sulfur atom, an oxygen atom or a nitrogen atom, or a functional group such as a carbonyl group, —SO—, —$SO_2$—, —$SO_3$—, —COO—, —CONH—, or —N(RN)— (here, RN represents an alkyl group having 1 to 5 carbon atoms). Regarding the ring to be formed, it is preferable that a ring containing the sulfur atom in the formula in the ring skeleton thereof is a 3-membered to 10-membered ring and it is particularly preferable that it is a 5-membered to 7-membered ring, in a case where the sulfur atom is included. Specific examples of the ring to be formed include a thiophene ring, a thiazole ring, a benzothiophene ring, a dibenzothiophene ring, a 9H-thioxanthene ring, a thioxanthone ring, a thianthrene ring, a phenoxathiin ring, a tetrahydrothiophenium ring, and a tetrahydrothiopyranium ring.

$R^{208}$ and $R^{209}$ each independently represent a hydrogen atom or an alkyl group having 1 to 5 carbon atoms and are preferably a hydrogen atom or an alkyl group having 1 to 3 carbon atoms. In a case where $R^{208}$ and $R^{209}$ each independently represent an alkyl group, $R^{208}$ and $R^{209}$ may be bonded to each other to form a ring.

$R^{210}$ represents an aryl group which may have a substituent, an alkyl group which may have a substituent, an alkenyl group which may have a substituent, or a $—SO_2—$-containing cyclic group which may have a substituent.

Examples of the aryl group as $R^{210}$ include an unsubstituted aryl group having 6 to 20 carbon atoms, and a phenyl group or a naphthyl group is preferable.

The alkyl group as $R^{210}$, a chain or cyclic alkyl group having 1 to 30 carbon atoms is preferable.

The alkenyl group as $R^{210}$ preferably has 2 to 10 carbon atoms. The $—SO_2—$-containing cyclic group which may have a substituent, as $R^{210}$, is preferably a "$—SO_2—$-containing polycyclic group", and more preferably a group represented by General Formula (a5-r-1).

Each $Y^{201}$ independently represents an arylene group, an alkylene group, or an alkenylene group.

Examples of the arylene group as $Y^{201}$ include groups obtained by removing one hydrogen atom from an aryl group mentioned as the aromatic hydrocarbon group represented by $R^{101}$ in General Formula (b-1) described above.

Examples of the alkylene group and alkenylene group as $Y^{201}$ include groups obtained by removing one hydrogen atom from the chain alkyl group or the chain alkenyl group as $R^{101}$ in General Formula (b-1) described above.

In General Formula (ca-4), x represents 1 or 2.

$W^{201}$ represents an (x+1) valent linking group, that is, a divalent or trivalent linking group.

The divalent linking group as $W^{201}$ is preferably a divalent hydrocarbon group which may have a substituent, and as examples thereof include the same divalent hydrocarbon group, which may have a substituent, as $Ya^{21}$ in General Formula (a2-1) described above. The divalent linking group as $W^{201}$ may be linear, branched, or cyclic, and it is more preferably cyclic. Among these, an arylene group having both terminals at which two carbonyl groups are combined is preferable. Examples of the arylene group include a phenylene group and a naphthylene group, and a phenylene group is particularly preferable.

Examples of the trivalent linking group as $W^{201}$ include a group obtained by removing one hydrogen atom from the above-described divalent linking group as $W^{201}$ and a group obtained by bonding the divalent linking group to another divalent linking group. The trivalent linking group as $W^{201}$ is preferably a group obtained by bonding two carbonyl groups to an arylene group.

Specific examples of the suitable cation represented by General Formula (ca-1) include cations each represented by Chemical Formulae (ca-1-1) to (ca-1-78) shown below.

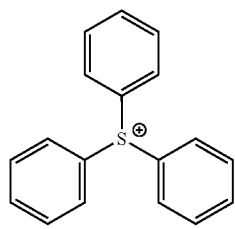
(ca-1-1)

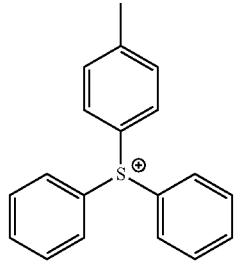
(ca-1-2)

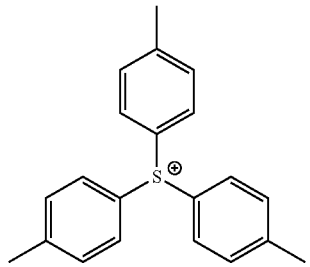
(ca-1-3)

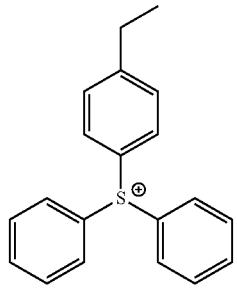
(ca-1-4)

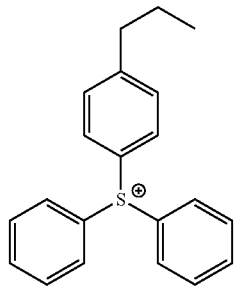
(ca-1-5)

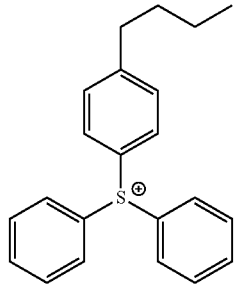
(ca-1-6)

(ca-1-7)
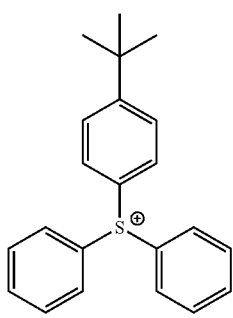
(ca-1-8)
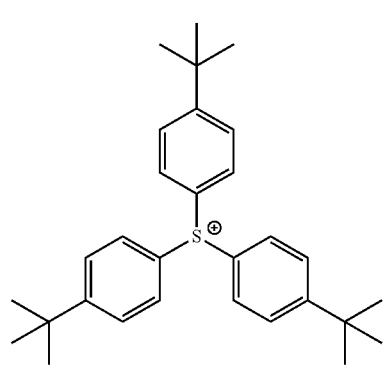
(ca-1-9)
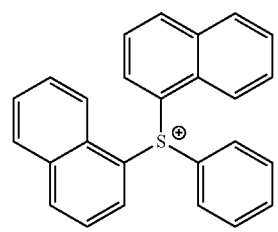
(ca-1-10)
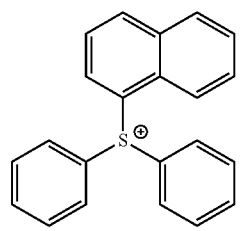
(ca-1-11)
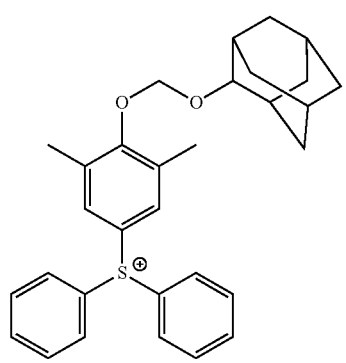
(ca-1-12)
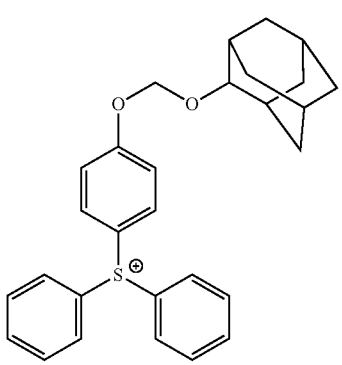
(ca-1-13)
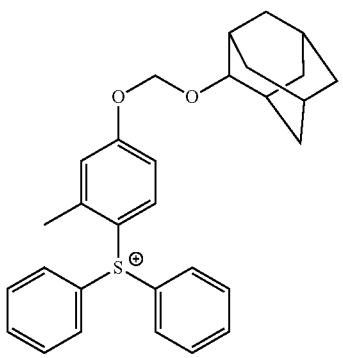
(ca-1-14)
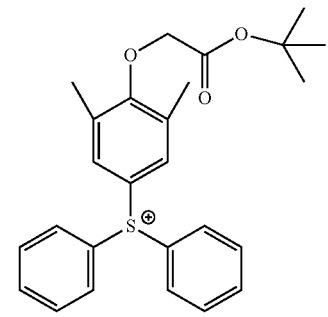
(ca-1-15)
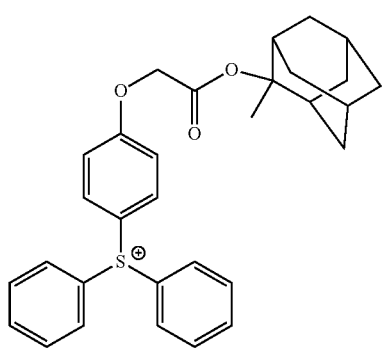

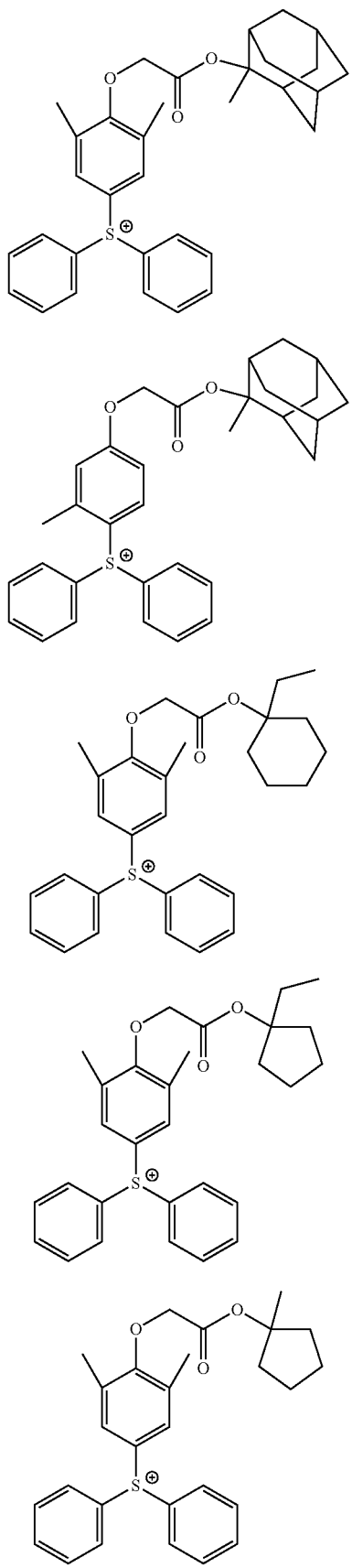
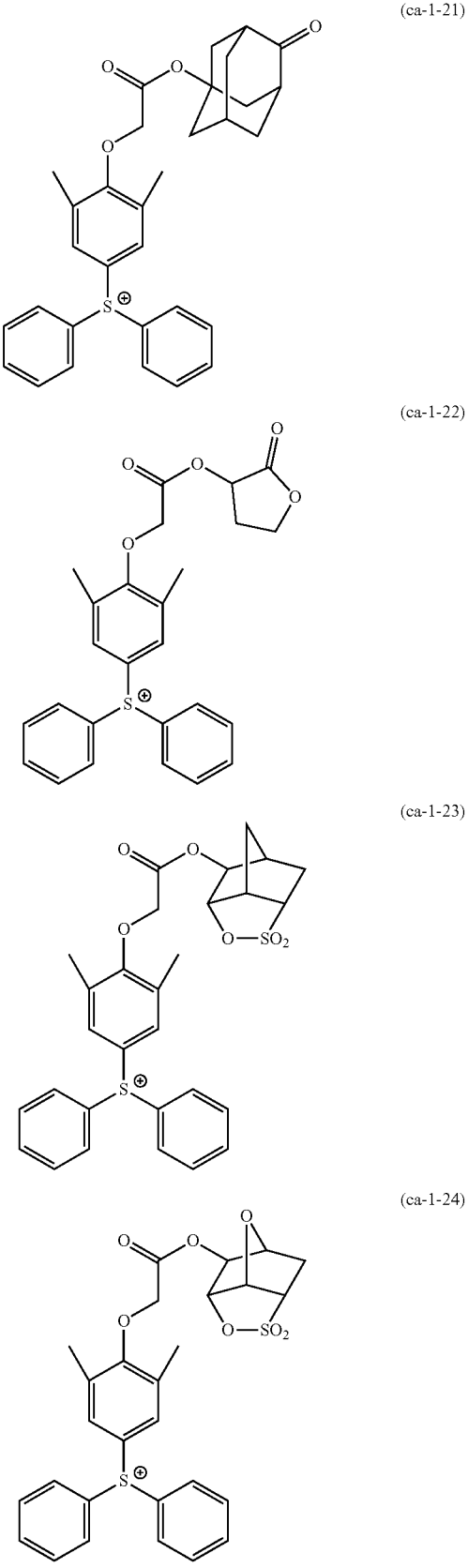

(ca-1-25)
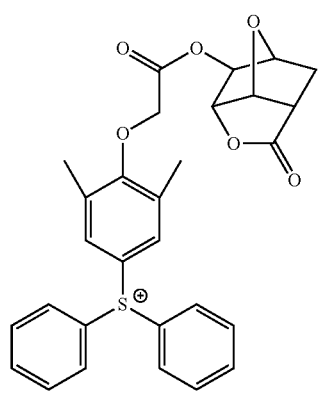
(ca-1-26)
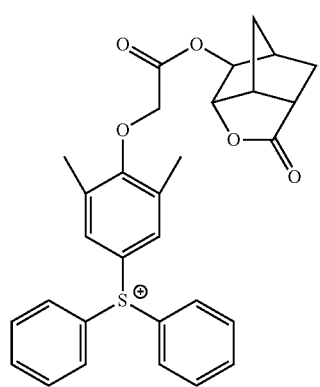
(ca-1-27)
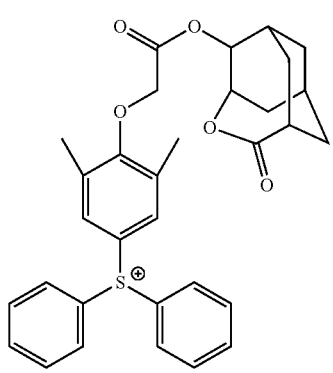
(ca-1-28)
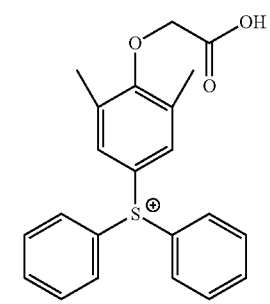
(ca-1-29)
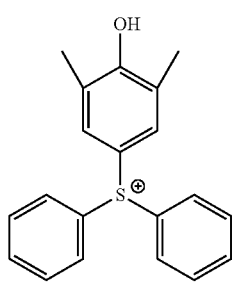
(ca-1-30)
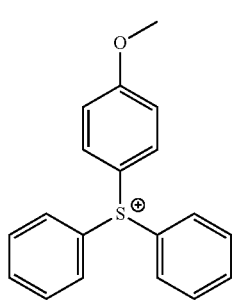
(ca-1-31)
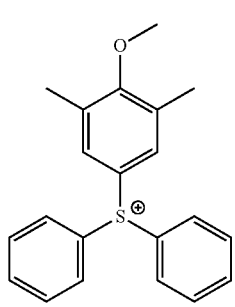
(ca-1-32)
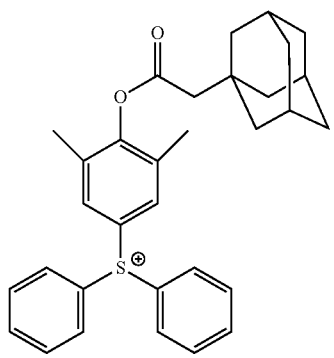
(ca-1-33)
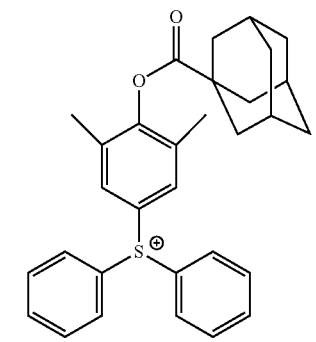

(ca-1-34)
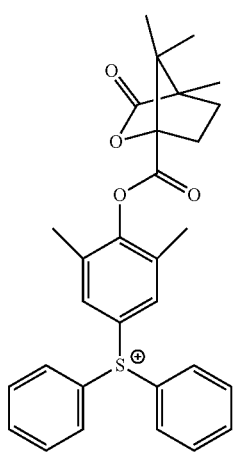
(ca-1-35)
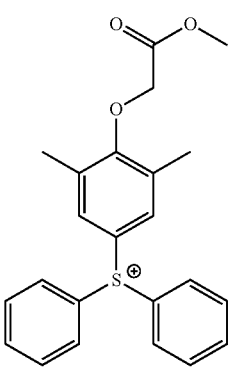
(ca-1-36)
(ca-1-37)
(ca-1-38)
(ca-1-39)
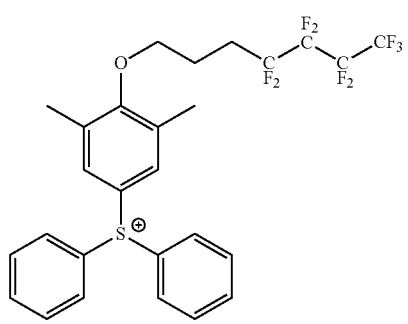
(ca-1-40)
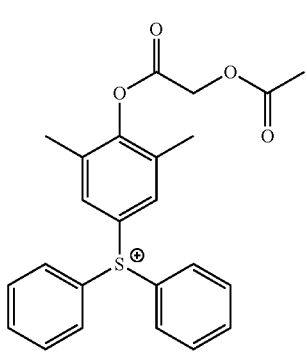
(ca-1-41)
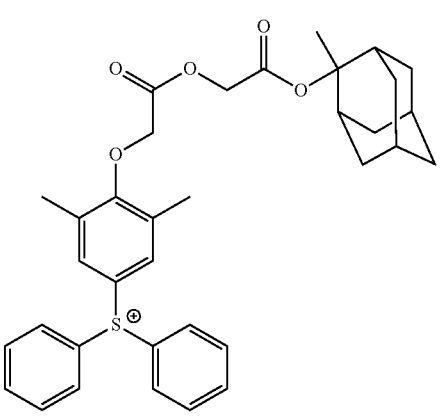

(ca-1-42)
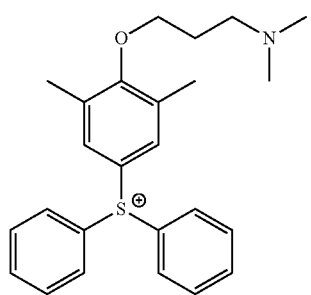
(ca-1-43)
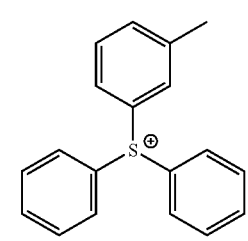
(ca-1-44)
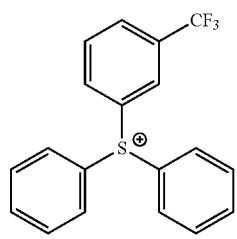
(ca-1-45)
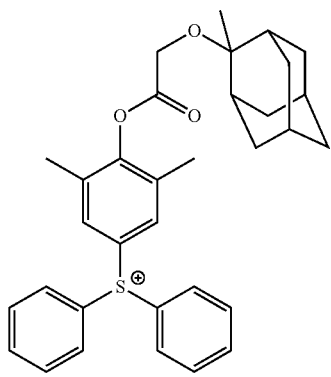
(ca-1-46)
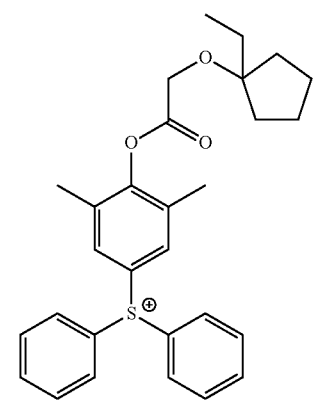
(ca-1-47)
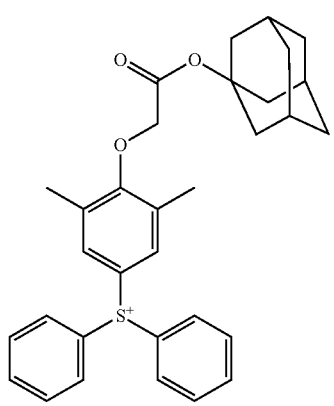
[In the formula, g1, g2, and g3 represent the numbers of repetitions, g1 is an integer in a range of 1 to 5, g2 is an integer in a range of 0 to 20, and g3 is an integer in a range of 0 to 20.]
(ca-1-48)
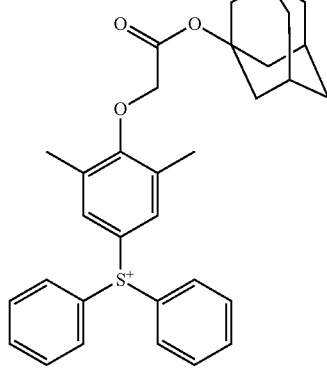
(ca-1-49)
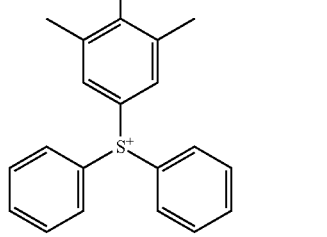
(ca-1-50)
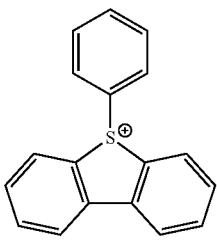

-continued
(ca-1-51)
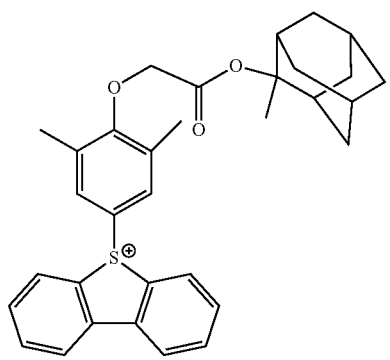
(ca-1-52)
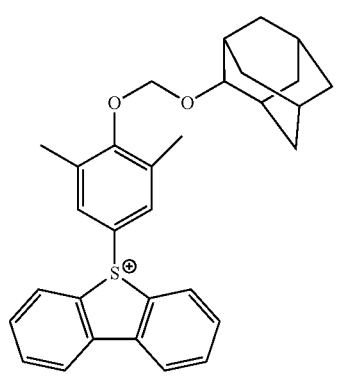
(ca-1-53)
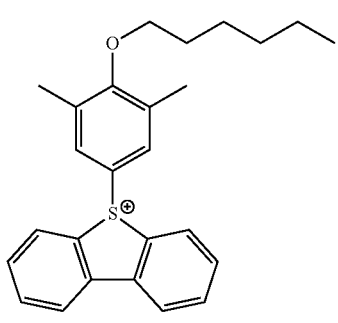
(ca-1-54)
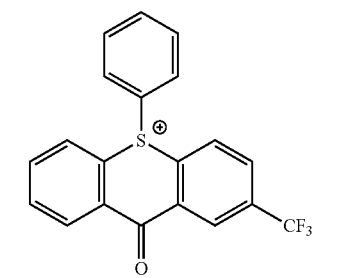
(ca-1-55)
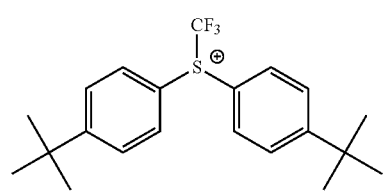
-continued
(ca-1-56)
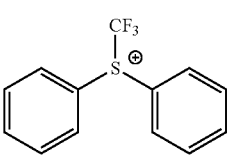
(ca-1-57)
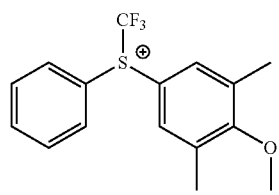
(ca-1-58)
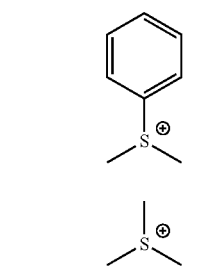
(ca-1-59)
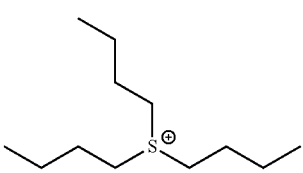
(ca-1-60)
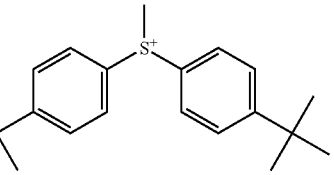
(ca-1-61)
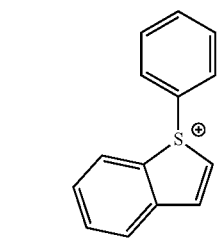
(ca-1-62)
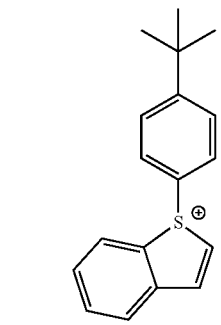
(ca-1-63)

(ca-1-64)
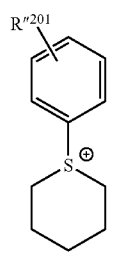
(ca-1-65)
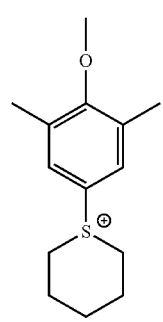
(ca-1-66)
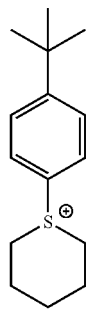
(ca-1-67)
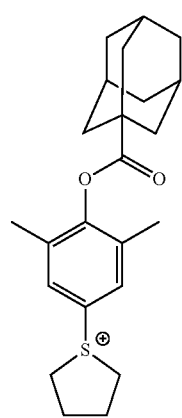
(ca-1-68)
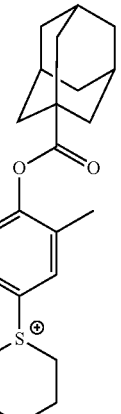
(ca-1-69)
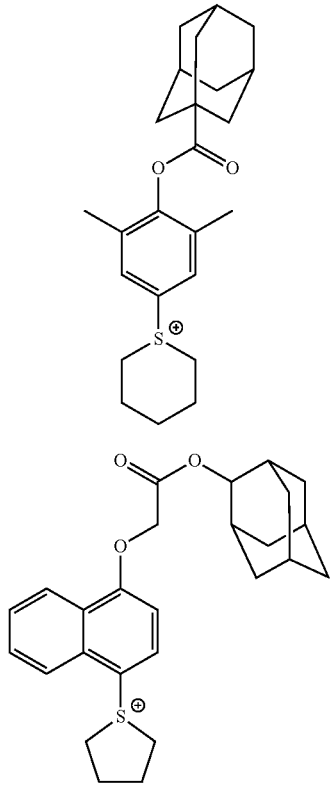
(ca-1-70)
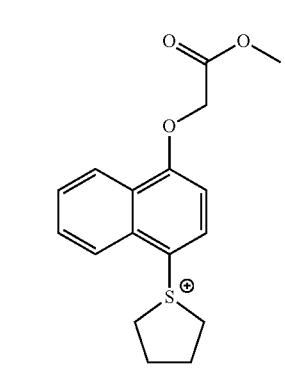
(ca-1-71)
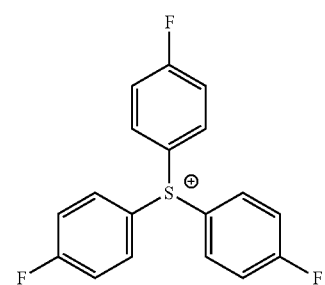
(ca-1-72)
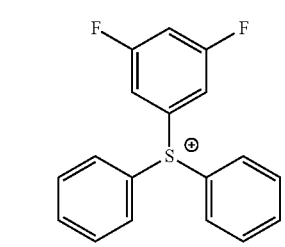

(ca-1-73)
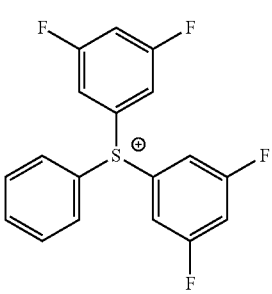

(ca-1-74)
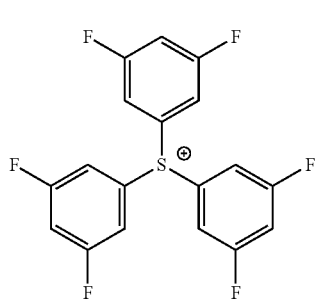

(ca-1-75)
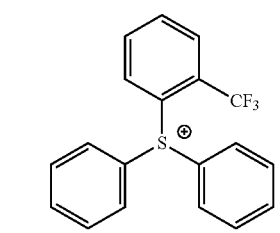

(ca-1-76)
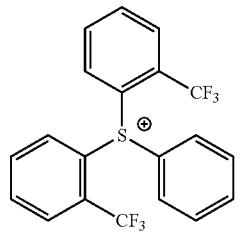

(ca-1-77)
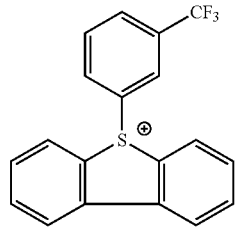

(ca-1-78)
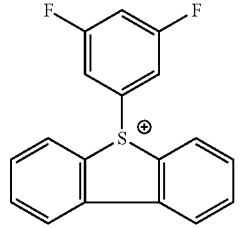

[In the formula, $R''^{201}$ represents a hydrogen atom or a substituent, and examples of the substituent include the same substituent as that exemplified as the substituent which may be contained in $R^{201}$ to $R^{207}$ and $R^{210}$ to $R^{212}$.]

Specific examples of suitable cations represented by General Formula (ca-2) include a diphenyliodonium cation and a bis(4-tert-butylphenyl)iodonium cation.

Specific examples of the suitable cations each represented by General Formula (ca-3) include cations each represented by General Formulae (ca-3-1) to (ca-3-6) shown below.

(ca-3-1)
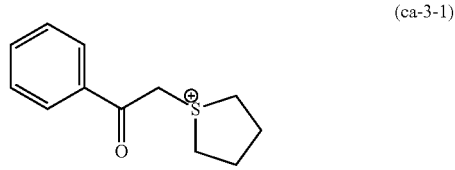

(ca-3-2)
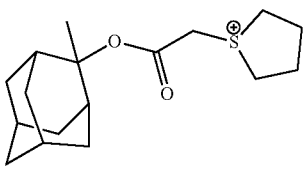

(ca-3-3)
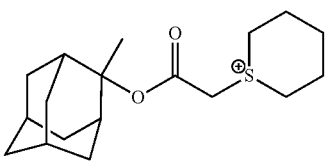

(ca-3-4)
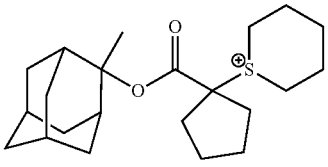

(ca-3-5)
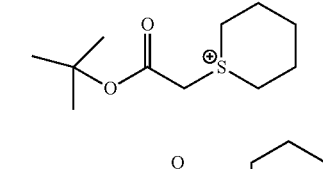

(ca-3-6)
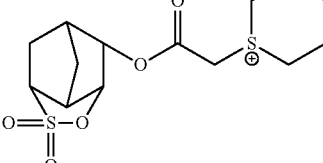

Specific examples of the suitable cations each represented by General Formula (ca-4) include cations each represented by General Formulae (ca-4-1) and (ca-4-2) shown below.

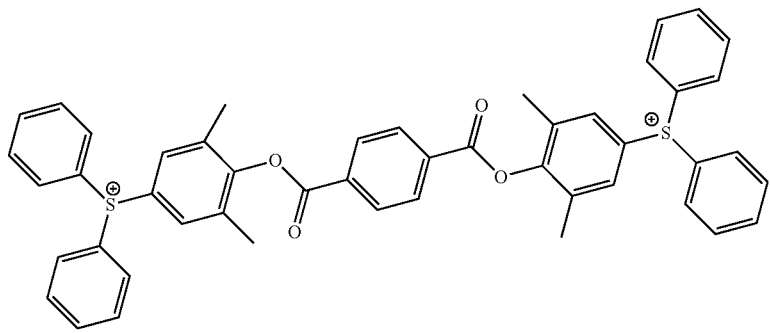
(ca-4-1)
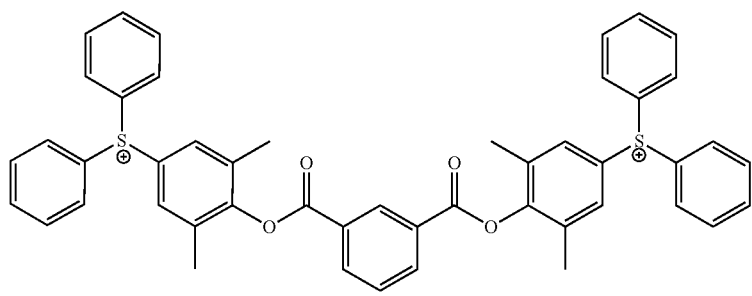
(ca-4-2)
Specific examples of the suitable cations each represented by General Formula (ca-5) include cations each represented by General Formulae (ca-5-1) to (ca-5-3) shown below.
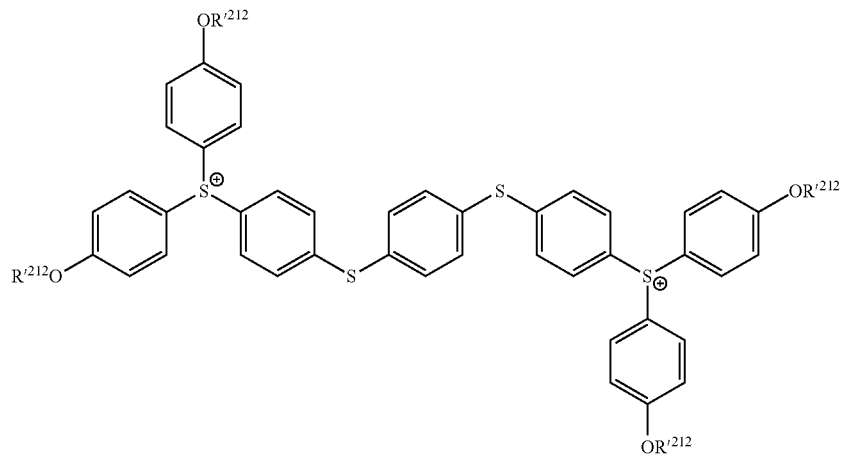
(ca-5-1)

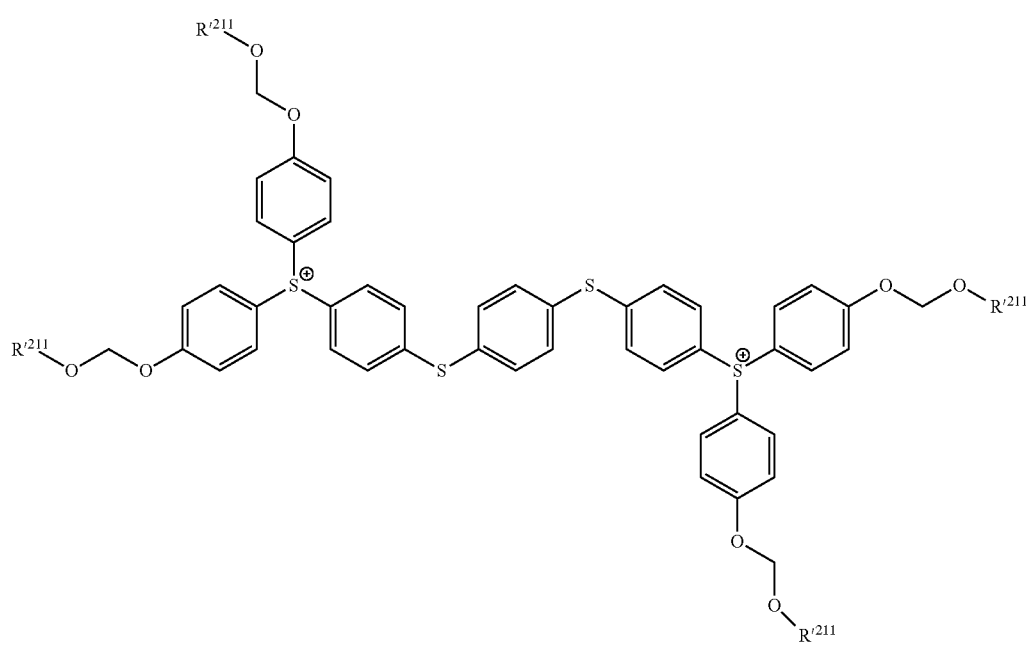

(ca-5-2)

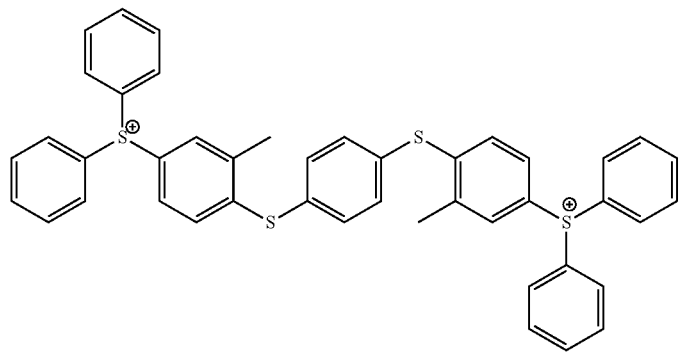

(ca-5-3)

Among the above cations, the cation moiety $((M^{m+})_{1/m})$ is preferably a cation represented by General Formula (ca-1).

The component (B) in the resist composition according to the present embodiment is preferably, among the above, a compound represented by General Formula (b0).

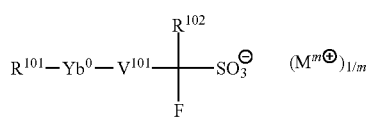

(b0)

[In the formula, $R^{101}$ represents a cyclic group which may have a substituent, a chain alkyl group which may have a substituent, or a chain alkenyl group which may have a substituent. $Yb^0$ represents a divalent linking group containing an oxygen atom. $V^{101}$ represents a single bond, an alkylene group, or a fluorinated alkylene group. $R^{102}$ represents a fluorinated alkyl group having 1 to 5 carbon atoms or a fluorine atom. $M^{m+}$ represents an m-valent organic cation. m represents an integer of 1 or more.]

$R^{101}$, $V^{101}$, and $R^{102}$ in General Formula (b0) are the same as $R^{101}$, $V^{101}$, and $R^{102}$ in General Formula (b-1).

Examples of $Yb^0$ in General Formula (b0) include the same one as the divalent linking group containing an oxygen atom, as in $Y^{101}$, in General Formula (b-1).

The compound represented by General Formula (b0) contains a divalent linking group containing an oxygen atom, as an essential constituent, as compared with the compound represented by General Formula (b-1). This makes it possible for the compound represented by General Formula (b0) to suitably control the diffusibility of the acid generated upon exposure as compared with the compound having the same structure and having no divalent linking group containing an oxygen atom, and thus it is possible to further improve the CDU and the resolution in resist pattern formation.

The component (B) in the resist composition according to the present embodiment is more preferably, among the above, a compound represented by General Formula (b0-1).

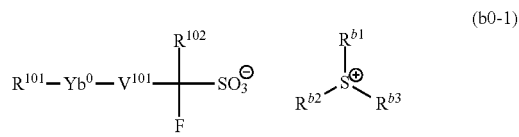

(b0-1)

[In the formula, $R^{101}$ represents a cyclic group which may have a substituent, a chain alkyl group which may have a substituent, or a chain alkenyl group which may have a substituent. $Yb^0$ represents a divalent linking group containing an oxygen atom. $V^{101}$ represents a single bond, an alkylene group, or a fluorinated alkylene group. $R^{102}$ represents a fluorinated alkyl group having 1 to 5 carbon atoms or a fluorine atom. $R^{b1}$ represents an aryl group having a fluorine atom or an aryl group having a fluorinated alkyl group. $R^{b2}$ and $R^{b3}$ each independently represent an aryl group which may have a substituent or are bonded to each other to form a ring together with a sulfur atom in the formula.]

In Regard to Anion Moiety

The anion moiety of the compound represented by General Formula (b0-1) is the same as the anion moiety of the compound represented by General Formula (b0).

In Regard to Cation Moiety

In General Formula (b0-1), $R^{b1}$ represents an aryl group having a fluorine atom or an aryl group having a fluorinated alkyl group. Examples of the aryl group include the same ones as the aryl groups as $R^{201}$ to $R^{203}$ in General Formula (ca-1).

Specific examples of the fluorinated alkyl group contained in the aryl group as $R^{b1}$ include a group obtained by substituting part or all of hydrogen atoms of an alkyl group having 1 to 12 carbon atoms with a fluorine atom. The alkyl group may be linear or branched.

Specific examples of the linear fluorinated alkyl group having 1 to 12 carbon atoms include a methyl group, an ethyl group, a propyl group, a butyl group, a pentyl group, a hexyl group, a heptyl group, an octyl group, a nonyl group, a decyl group, and an undecyl group, a group obtained by substituting part or all of hydrogen atoms of a dodecyl group with a fluorine atom. Specific examples of the branched fluorinated alkyl group having 1 to 12 carbon atoms include a 1-methylethyl group, a 1,1-dimethylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a group obtained by substituting part or all of hydrogen atoms of a 4-methylpentyl group with a fluorine atom.

The fluorinated alkyl group contained in the aryl group as $R^{b1}$ is, among the above, preferably a group obtained by substituting part or all of hydrogen atoms of an alkyl group having 1 to 5 carbon atoms with a fluorine atom, more preferably a group obtained by substituting part or all of hydrogen atoms of an alkyl group having 1 to 3 carbon atoms with a fluorine atom, and still more preferably a trifluoromethyl group.

In General Formula (b0-1), $R^{b1}$ is preferably, among the above, an aryl group having a fluorine atom or an aryl group having a fluorinated alkyl group having 1 to 5 carbon atoms, and more preferably an aryl group having a fluorine atom.

Examples of the aryl group which may have a substituent as $R^{b2}$ and $R^{b3}$ and the ring formed by bonding $R^{b2}$ and $R^{b3}$ to each other together with a sulfur atom in the formula each include the same one as the aryl group which may have a substituent, as $R^{201}$ to $R^{203}$, in General Formula (ca-1) and the ring formed by bonding $R^{201}$ to $R^{203}$ to each other together with a sulfur atom in the formula.

In General Formula (b0-1), $R^{b2}$ and $R^{b3}$ are, among the above, are each independently preferably an aryl group which may have a substituent. More specifically, it is preferable that at least one of $R^{b2}$ and $R^{b3}$ is an aryl group having a fluorine atom or an aryl group having a fluorinated alkyl group.

In General Formula (b0-1), the number of fluorine atoms contained in the aryl group as $R^{b1}$ to $R^{b3}$ is preferably in a range of 2 to 8 and more preferably in a range of 2 to 6.

In a case where the number of fluorine atoms contained in the aryl group as $R^{b1}$ to $R^{b3}$ is 2 or more, the decomposition of the compound represented by General Formula (b0-1) upon exposure is promoted, and thus the sensitivity is further improved. On the other hand, in a case where the number of fluorine atoms contained in the aryl group as $R^{b1}$ to $R^{b3}$ is 6 or less, the solubility in a developing solution can be further improved.

The compound represented by General Formula (b0-1) contains an aryl group having a fluorine atom or an aryl group having a fluorinated alkyl group in the cation moiety, as an essential constituent, as compared with the compound represented by General Formula (b0). As a result, the decomposition of the compound represented by General Formula (b0-1) upon exposure is promoted as compared with a compound having an aryl group having a fluorine atom in the cation moiety or a compound having no aryl group having a fluorinated alkyl group, and thus it is possible to further improve the sensitivity in resist pattern formation.

Suitable specific examples of the component (B) in the resist composition according to the present embodiment are shown below.

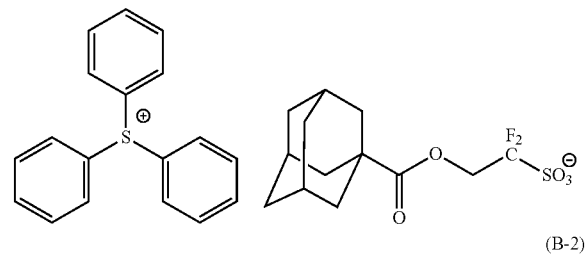

(B-1)

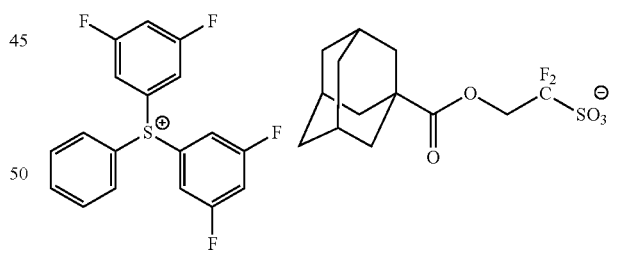

(B-2)

In the resist composition according to the present embodiment, the component (B) may be used alone or in a combination of two or more kinds thereof.

In a case where the resist composition contains the component (B), the content of the component (B) in the resist composition is preferably less than 50 parts by mass, more preferably in a range of 10 to 40 parts by mass, and still more preferably in a range of 15 to 30 parts by mass, with respect to 100 parts by mass of the component (A1).

In a case where the content of the component (B) is set to be in the preferred range described above, pattern formation can be satisfactorily carried out. Further, in a case where each component of the resist composition is dissolved in an organic solvent, the above range is preferable since a homogeneous solution is easily obtained and the storage stability of the resist composition is improved.

<<Base Component (D)>>

The resist composition according to the present embodiment may further contain, in addition to the component (A), a base component (a component (D)) that traps (that is, controls the acid diffusion) acid that is generated upon exposure. The component (D) acts as a quencher (an acid diffusion controlling agent) that traps acid that is generated in the resist composition upon exposure.

Examples of the component (D) include a photodecomposable base (D1) having an acid diffusion controllability (hereinafter, referred to as a "component (D1)") which is lost by the decomposition upon exposure and a nitrogen-containing organic compound (D2) (hereinafter, referred to as a "component (D2)") which does not correspond to the component (D1). Among these, the photodecomposable base (the component (D1)) is preferable since it is easy to enhance the characteristics of high sensitivity, roughness reduction, and suppression of the occurrence of coating defects.

In Regard to Component (D1)

In a case where a resist composition containing the component (D1) is obtained, the contrast between exposed portions and unexposed portions of the resist film can be further improved at the time of the formation of a resist pattern.

The component (D1) is not particularly limited as long as it decomposes upon exposure and loses the acid diffusion controllability. The component (D1) is preferably one or more compounds selected from the group consisting of a compound represented by General Formula (d1-1) (hereinafter, referred to as a "component (d1-1)"), a compound represented by General Formula (d1-2) (hereinafter, referred to as a "component (d1-2)"), and a compound represented by General Formula (d1-3) (hereinafter, referred to as a "component (d1-3)").

At exposed portions of the resist film, the components (d1-1) to (d1-3) are decomposed and then lose the acid diffusion controllability (basicity), and thus the components (d1-1) to (d1-3) cannot act as a quencher, whereas the components (d1-1) to (d1-3) act as a quencher at unexposed portions of the resist film.

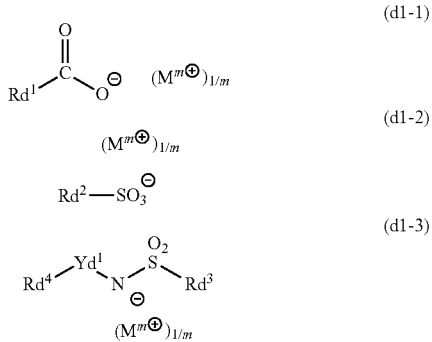

[In the formulae, $Rd^1$ to $Rd^4$ represents cyclic groups which may have a substituent, chain alkyl groups which may have a substituent, or chain alkenyl groups which may have a substituent. Here, the carbon atom adjacent to the S atom in $Rd^2$ in General Formula (d1-2) has no fluorine atom bonded thereto. $Yd^1$ represents a single bond or a divalent linking group. m represents an integer of 1 or more, and each $M^{m+}$ independently represents an m-valent organic cation.]

{Component (d1-1)}

Anion Moiety

In General Formula (d1-1), $Rd^1$ represents a cyclic group which may have a substituent, a chain alkyl group which may have a substituent, or a chain alkenyl group which may have a substituent, and examples thereof include the same one as $R'^{201}$.

Among these, $Rd^1$ is preferably an aromatic hydrocarbon group which may have a substituent, an aliphatic cyclic group which may have a substituent, or a chain alkyl group which may have a substituent. Examples of the substituent which may be contained in these groups include a hydroxyl group, an oxo group, an alkyl group, an aryl group, a fluorine atom, a fluorinated alkyl group, lactone-containing cyclic groups each represented by General Formulae (a2-r-1) to (a2-r-7), an ether bond, an ester bond, and a combination thereof. In a case where an ether bond or an ester bond is included as the substituent, the substituent may be bonded via an alkylene group, and linking groups each represented by Formulae (y-a1-1) to (y-a1-5) are preferable as the substituent. It is noted that in a case where the aromatic hydrocarbon group, the aliphatic cyclic group, or the chain alkyl group, as $Rd^1$, has a linking group each represented by General Formulae (y-a1-1) to (y-a1-7) as a substituent, in General Formulae (y-a1-1) to (y-a1-7), the group that is bonded to a carbon atom constituting the aromatic hydrocarbon group, the aliphatic cyclic group, or the chain alkyl group, as $Rd^1$, in General Formula (d3-1) is $V^{101}$ in General Formulae (y-a1-1) to (y-a1-7).

Suitable examples of the aromatic hydrocarbon group include a phenyl group, a naphthyl group, and a polycyclic structure (a polycyclic structure including a bicyclooctane skeleton and a ring structure other than the bicyclooctane skeleton) including a bicyclooctane skeleton.

The aliphatic cyclic group is preferably a group obtained by removing one or more hydrogen atoms from a polycycloalkane such as adamantane, norbornane, isobornane, tricyclodecane, or tetracyclododecane.

The chain alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl group, or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, or a 4-methylpentyl group.

In a case where the chain alkyl group is a fluorinated alkyl group having a fluorine atom or a fluorinated alkyl group as a substituent, the fluorinated alkyl group preferably has 1 to 11 carbon atom, more preferably 1 to 8 carbon atoms, and still more preferably 1 to 4 carbon atoms. The fluorinated alkyl group may contain an atom other than a fluorine atom. Examples of the atom other than a fluorine atom include an oxygen atom, a sulfur atom, and a nitrogen atom.

Specific examples of the preferred anion moiety for the component (d1-1) are shown below.

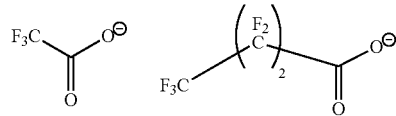

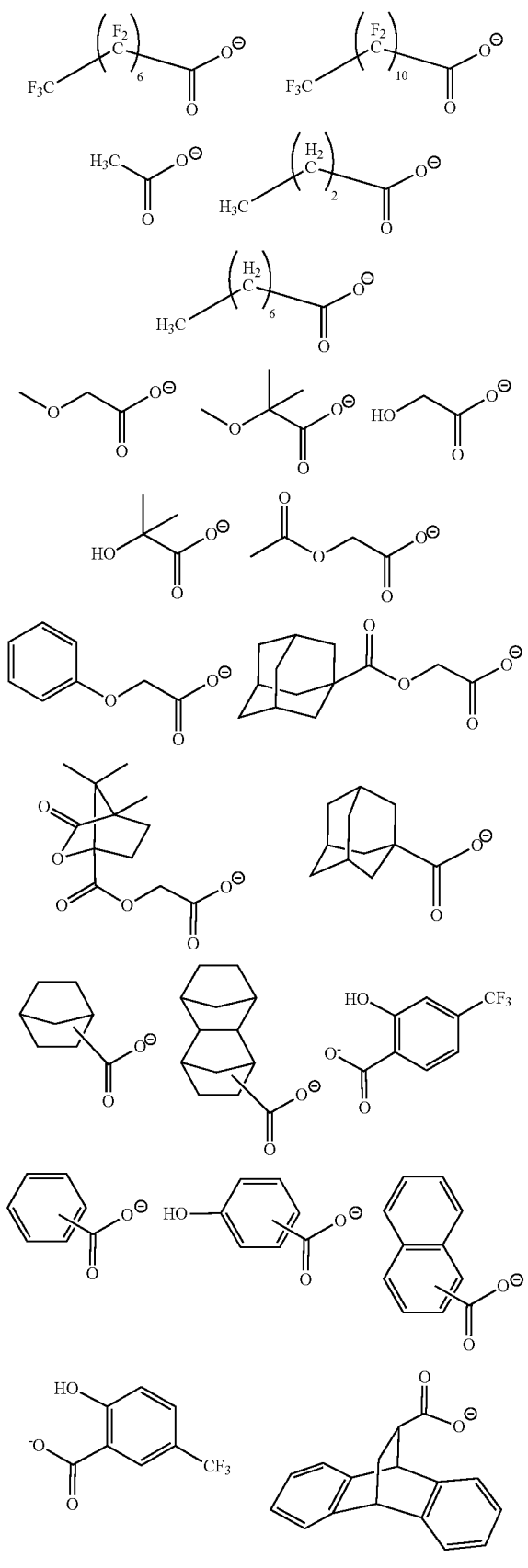

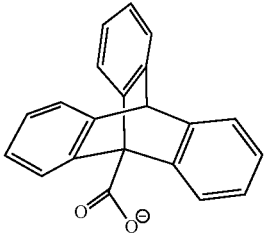

Cation Moiety

In General Formula (d1-1), $M^{m+}$ represents an m-valent organic cation. Suitable examples of the organic cation as $M^{m+}$ include the same ones as the cations each represented by General Formulae (ca-1) to (ca-5), a cation represented by General Formula (ca-1) is preferable, and cations each represented by Formulae (ca-1-1) to (ca-1-78) are more preferable.

The component (d1-1) may be used alone or in a combination of two or more kinds thereof.

{Component (d1-2)}

Anion Moiety

In General Formula (d1-2), $Rd^2$ represents a cyclic group which may have a substituent, a chain alkyl group which may have a substituent, or a chain alkenyl group which may have a substituent, and examples thereof include the same one as $R'^{201}$.

Here, the carbon atom adjacent to the S atom in $Rd^2$ has no fluorine atom bonded thereto (the carbon atom adjacent to the S atom in $Rd^2$ is not substituted with a fluorine atom). As a result, the anion of the component (d1-2) becomes a suitably weak acid anion, thereby improving the quenching ability of the component (D).

$Rd^2$ is preferably a chain alkyl group which may have a substituent or an aliphatic cyclic group which may have a substituent. The chain alkyl group preferably has 1 to 10 carbon atoms and more preferably 3 to 10 carbon atoms. The aliphatic cyclic group is more preferably a group (which may have a substituent) obtained by removing one or more hydrogen atoms from adamantane, norbornane, isobornane, tricyclodecane, tetracyclododecane, or the like; and a group obtained by removing one or more hydrogen atoms from camphor or the like.

The hydrocarbon group as $Rd^2$ may have a substituent. Examples of the substituent include the same one as the substituent which may be contained in the hydrocarbon group (the aromatic hydrocarbon group, the aliphatic cyclic group, or the chain alkyl group) as $Rd^1$ in General Formula (d1-1).

Specific examples of the preferred anion moiety for the component (d1-2) are shown below.

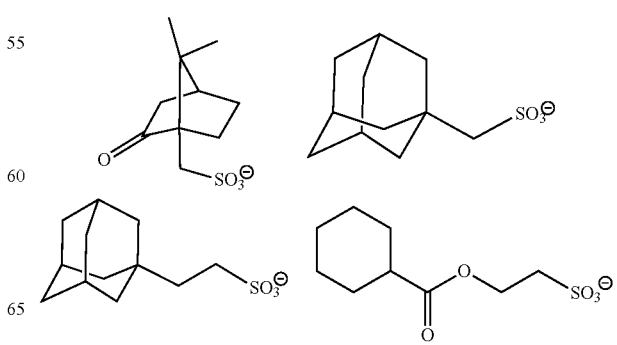

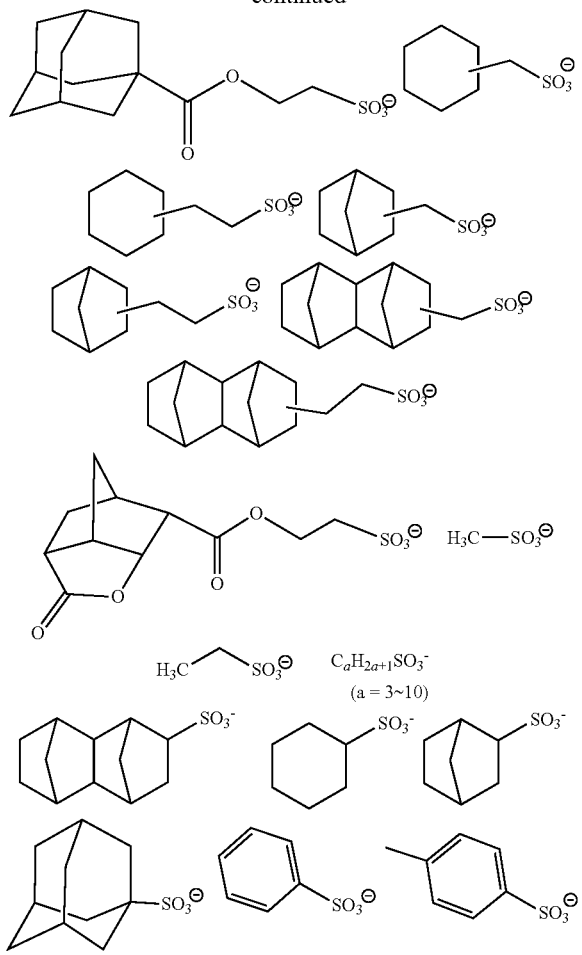

Cation Moiety

In General Formula (d1-2), $M^{m+}$ represents an m-valent organic cation and is the same as $M^{m+}$ in General Formula (d1-1).

The component (d1-2) may be used alone or in a combination of two or more kinds thereof.

{Component (d1-3)}

Anion Moiety

In General Formula (d1-3), $Rd^3$ represents a cyclic group which may have a substituent, a chain alkyl group which may have a substituent, or a chain alkenyl group which may have a substituent, examples thereof include the same one as $R'^{201}$, and a cyclic group containing a fluorine atom, a chain alkyl group, or a chain alkenyl group is preferable. Among them, a fluorinated alkyl group is preferable, and the same one as the above fluorinated alkyl group as $Rd^1$ is more preferable.

In General Formula (d1-3), $Rd^4$ represents a cyclic group which may have a substituent, a chain alkyl group which may have a substituent, or a chain alkenyl group which may have a substituent, and examples thereof include the same one as $R'^{201}$.

Among them, an alkyl group which may have a substituent, an alkoxy group which may have a substituent, an alkenyl group which may have a substituent, or a cyclic group which may have a substituent is preferable.

The alkyl group as $Rd^4$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. Part of hydrogen atoms in the alkyl group as $Rd^4$ may be substituted with a hydroxyl group, a cyano group, or the like.

The alkoxy group as $Rd^4$ is preferably an alkoxy group having 1 to 5 carbon atoms, and specific examples of the alkoxy group having 1 to 5 carbon atoms include a methoxy group, an ethoxy group, an n-propoxy group, an iso-propoxy group, an n-butoxy group, and a tert-butoxy group. Among these, a methoxy group and an ethoxy group are preferable.

Examples of the alkenyl group as $Rd^4$ include the same one as $R'^{201}$, and a vinyl group, a propenyl group (an allyl group), a 1-methylpropenyl group, or a 2-methylpropenyl group is preferable. These groups may have an alkyl group having 1 to 5 carbon atoms or a halogenated alkyl group having 1 to 5 carbon atoms as a substituent.

Examples of the cyclic group as $Rd^4$ include the same one as the cyclic group as $R'^{201}$, and an alicyclic group obtained by removing one or more hydrogen atoms from a cycloalkane such as cyclopentane, cyclohexane, adamantane, norbornane, isobornane, tricyclodecane, or tetracyclododecane, or an aromatic group such as a phenyl group or a naphthyl group is preferable. In a case where $Rd^4$ represents an alicyclic group, the resist composition can be satisfactorily dissolved in an organic solvent, thereby improving the lithography characteristics. In a case where $Rd^4$ is an aromatic group, the resist composition is excellent in light absorption efficiency and thus has good sensitivity and lithography characteristics in the lithography using EUV or the like as a light source for exposure.

In General Formula (d1-3), $Yd^1$ represents a single bond or a divalent linking group.

The divalent linking group as $Yd^1$ is not particularly limited, and examples thereof include a divalent hydrocarbon group (an aliphatic hydrocarbon group or an aromatic hydrocarbon group) which may have a substituent and a divalent linking group containing a hetero atom. Examples thereof each include the same ones as the divalent hydrocarbon group which may have a substituent and the divalent linking group containing a hetero atom, which are described above as the divalent linking group as $Ya^{21}$ in General Formula (a2-1).

$Yd^1$ is preferably a carbonyl group, an ester bond, an amide bond, an alkylene group, or a combination of these. The alkylene group is more preferably a linear or branched alkylene group and still more preferably a methylene group or an ethylene group.

Specific examples of the preferred anion moiety for the component (d1-3) are shown below.

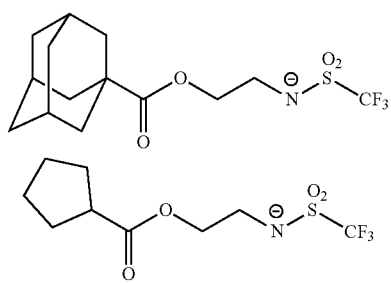

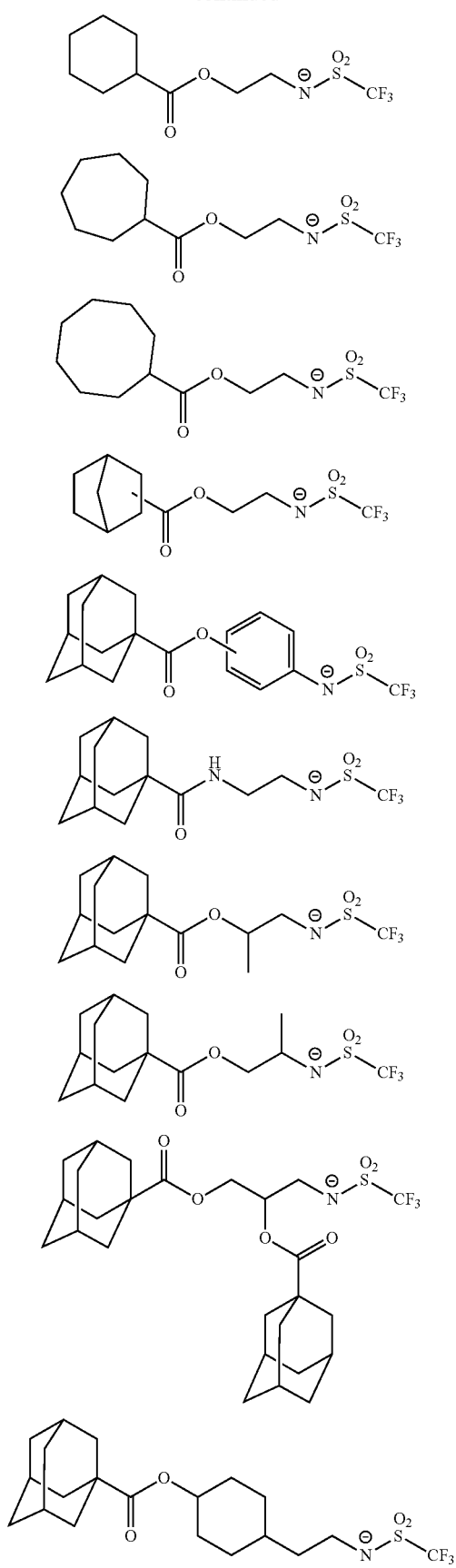
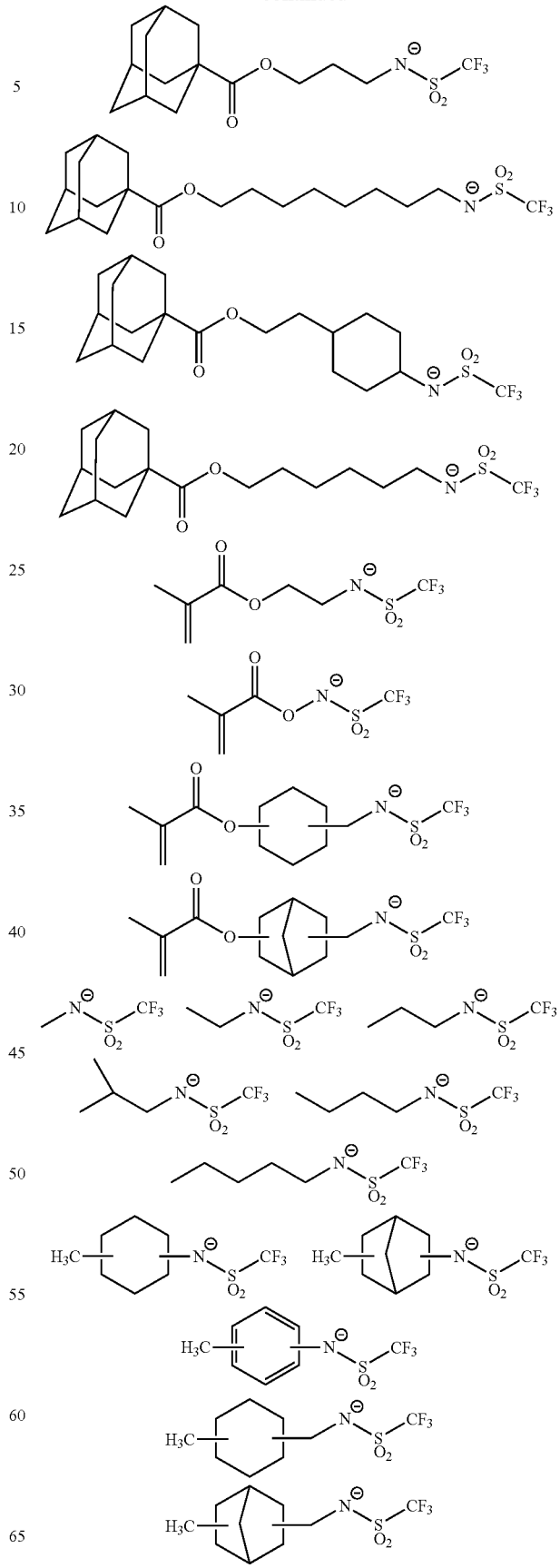

-continued

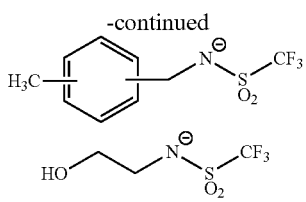

Cation Moiety

In General Formula (d1-3), $M^{m+}$ represents an m-valent organic cation and is the same as $M^{m+}$ in General Formula (d1-1).

The component (d1-3) may be used alone or in a combination of two or more kinds thereof.

As the component (D1), only one of the above-described components (d1-1) to (d1-3) or a combination of two or more kinds thereof may be used.

In a case where the resist composition contains the component (D1), the content of the component (D1) in the resist composition is preferably in a range of 0.5 to 20 parts by mass, more preferably in a range of 1 to 15 parts by mass, and still more preferably in a range of 2 to 8 parts by mass with respect to 100 parts by mass of the component (A1).

In a case where the content of the component (D1) is equal to or larger than the preferred lower limit value, excellent lithography characteristics and an excellent resist pattern shape are easily obtained. On the other hand, in a case where the content of the component (D1) is equal to or smaller than the upper limit value, the sensitivity can be maintained satisfactorily and the throughput is also excellent.

Method of Producing Component (D1):

The methods of producing the above components (d1-1) and (d1-2) are not particularly limited, and the components (d1-1) and (d1-2) can be produced by conventionally known methods.

Further, the method of producing the component (d1-3) is not particularly limited, and the component (d1-3) can be produced in the same manner as disclosed in United States Patent Application, Publication No. 2012-0149916.

In Regard to Component (D2)

The component (D) may contain a nitrogen-containing organic compound component (hereinafter, referred to as a "component (D2)") which does not correspond to the above-described component (D1).

The component (D2) is not particularly limited as long as it acts as an acid diffusion controlling agent and does not correspond to the component (D1), and any known compound may be used. Among the above, aliphatic amines are preferable, and among the aliphatic amines, a secondary aliphatic amine or a tertiary aliphatic amine is more preferable.

An aliphatic amine is an amine having one or more aliphatic groups, and the aliphatic groups preferably have 1 to 12 carbon atoms.

Examples of these aliphatic amines include an amine obtained by substituting at least one hydrogen atom of ammonia ($NH_3$) with an alkyl group or hydroxyalkyl group having 12 or fewer carbon atoms (alkyl amines or alkyl alcohol amines) and a cyclic amine.

Specific examples of the alkyl amine and the alkyl alcohol amine include monoalkyl amines such as n-hexyl amine, n-heptyl amine, n-octyl amine, n-nonyl amine, and n-decyl amine; dialkyl amines such as diethyl amine, di-n-propyl amine, di-n-heptyl amine, di-n-octyl amine, and dicyclohexyl amine; trialkyl amines such as trimethyl amine, tri-ethyl amine, tri-n-propyl amine, tri-n-butyl amine, tri-n-hexyl amine, tri-n-pentyl amine, tri-n-heptyl amine, tri-n-octyl amine, tri-n-nonyl amine, tri-n-decyl amine, and tri-n-dodecyl amine; and alkyl alcohol amines such as diethanol amine, triethanol amine, diisopropanol amine, triisopropanol amine, di-n-octanol amine, and tri-n-octanol amine. Among these, trialkyl amines of 5 to 10 carbon atoms are preferable, and tri-n-pentyl amine and tri-n-octyl amine are particularly preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris {2-(2-methoxyethoxy)ethyl}amine, tris{2-(2-methoxyethoxymethoxy)ethyl}amine, tris {2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanol amine triacetate, and triethanol amine triacetate is preferable.

In addition, as the component (D2), an aromatic amine may be used.

Examples of aromatic amines include 4-dimethylaminopyridine, pyrrole, indole, pyrazole, imidazole, and derivatives thereof, tribenzylamine, 2,6-diisopropylaniline, and N-tert-butoxycarbonylpyrrolidine.

The component (D2) may be used alone or in a combination of two or more kinds thereof.

In a case where the resist composition contains the component (D2), the content of the component (D2) in the resist composition is typically in a range of 0.01 to 5 parts by mass with respect to 100 parts by mass of the component (A1). By setting the content within the above range, the resist pattern shape, the post-exposure temporal stability, and the like are improved.

<<At Least One Compound (E) Selected from Group Consisting of Organic Carboxylic Acid, Phosphorus Oxo Acid, and Derivatives Thereof>>

For the purpose of preventing any deterioration in sensitivity, and improving the resist pattern shape and the post-exposure temporal stability, the resist composition according to the present embodiment may contain, as an optional component, at least one compound (E) (hereinafter referred to as a component (E)) selected from the group consisting of an organic carboxylic acid, and a phosphorus oxo acid and a derivative thereof.

Examples of the suitable organic carboxylic acid include acetic acid, malonic acid, citric acid, malic acid, succinic acid, benzoic acid, and salicylic acid. Examples of the phosphorus oxo acid include phosphoric acid, phosphonic acid, and phosphinic acid. Among these, phosphonic acid is particularly preferable.

Examples of the phosphorus oxo acid derivative include an ester obtained by substituting a hydrogen atom in the above-described oxo acid with a hydrocarbon group. Examples of the hydrocarbon group include an alkyl group having 1 to 5 carbon atoms and an aryl group having 6 to 15 carbon atoms.

Examples of the phosphoric acid derivative include phosphoric acid esters such as di-n-butyl phosphate and diphenyl phosphate.

Examples of the phosphonic acid derivative include phosphonic acid esters such as dimethyl phosphonate, di-n-butyl phosphonate, phenylphosphonic acid, diphenyl phosphonate, and dibenzyl phosphonate.

Examples of the phosphinic acid derivative include phosphinic acid esters and phenylphosphinic acid.

In the resist composition according to the present embodiment, the component (E) may be used alone or in a combination of two or more kinds thereof.

In a case where the resist composition contains the component (E), the content of the component (E) is typically in a range of 0.01 to 5 parts by mass with respect to 100 parts by mass of the component (A1).

<<Fluorine Additive Component (F)>>

The resist composition according to the present embodiment may further include a fluorine additive component (hereinafter, referred to as a "component (F)") in order to impart water repellency to the resist film or to improve lithography characteristics.

As the component (F), a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be mentioned.

Specific examples of the component (F) include polymers having a constitutional unit (f1) represented by General Formula (f1-1) shown below. This polymer is preferably a polymer (homopolymer) consisting of a constitutional unit (f1) represented by General Formula (f1-1) shown below; a copolymer of the constitutional unit (f1) and the constitutional unit (a1); and a copolymer of the constitutional unit (f1), a constitutional unit derived from acrylic acid or methacrylic acid, and the above-described constitutional unit (a1). The constitutional unit (a1) to be copolymerized with the constitutional unit (f1) is preferably a constitutional unit derived from 1-ethyl-1-cyclooctyl (meth)acrylate or a constitutional unit derived from 1-methyl-1-adamantyl (meth)acrylate.

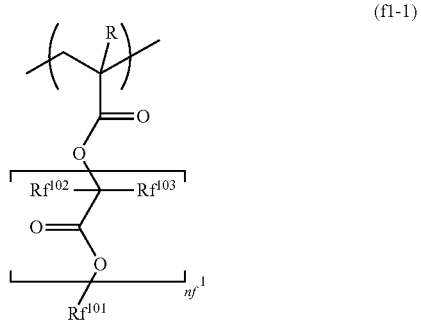

(f1-1)

[In the formula, R has the same definition as described above. $Rf^{102}$ and $Rf^{103}$ each independently represent a hydrogen atom, a halogen atom, an alkyl group having 1 to 5 carbon atoms, or a halogenated alkyl group having 1 to 5 carbon atoms, and $Rf^{102}$ and $Rf^{103}$ may be the same as or different from each other. $nf^1$ represents an integer in a range of 0 to 5 and $Rf^{101}$ represents an organic group containing a fluorine atom.]

In General Formula (f1-1), R bonded to the carbon atom at the α-position has the same definition as described above. R is preferably a hydrogen atom or a methyl group.

In General Formula (f1-1), the halogen atom of $Rf^{102}$ and $Rf^{103}$ is preferably a fluorine atom. Examples of the alkyl group having 1 to 5 carbon atoms as $Rf^{102}$ and $Rf^{103}$ include the same one as the alkyl group having 1 to 5 carbon atoms as R, and a methyl group or an ethyl group is preferable. Specific examples of the halogenated alkyl group having 1 to 5 carbon atoms as $Rf^{102}$ and $Rf^{103}$ include a group obtained by substituting part or all of hydrogen atoms of the above-described alkyl group having 1 to 5 carbon atoms with a halogen atom. The halogen atom is preferably a fluorine atom. Among these examples, as $Rf^{102}$ and $Rf^{103}$, a hydrogen atom, a fluorine atom, or an alkyl group having 1 to 5 carbon atoms is preferable, and a hydrogen atom, a fluorine atom, a methyl group, or an ethyl group is more preferable.

In General Formula (f1-1), $nf^1$ represents an integer in a range of 0 to 5, preferably an integer in a range of 0 to 3, and more preferably an integer of 1 or 2.

In General Formula (f1-1), $Rf^{101}$ represents an organic group containing a fluorine atom and is preferably a hydrocarbon group containing a fluorine atom.

The hydrocarbon group containing a fluorine atom may be linear, branched, or cyclic, and preferably has 1 to 20 carbon atoms, more preferably 1 to 15 carbon atoms, and particularly preferably 1 to 10 carbon atoms.

In addition, in the hydrocarbon group containing a fluorine atom, 25% or more of the hydrogen atoms in the hydrocarbon group are preferably fluorinated, more preferably 50% or more are fluorinated, and particularly preferably 60% or more are fluorinated since the hydrophobicity of the resist film during immersion exposure increases.

Among them, $Rf^{101}$ is more preferably a fluorinated hydrocarbon group having 1 to 6 carbon atoms and particularly preferably a trifluoromethyl group, —CH$_2$—CF$_3$, —CH$_2$—CF$_2$—CF$_3$, or —CH(CF$_3$)$_2$, —CH$_2$—CH$_2$—CF$_3$, or —CH$_2$—CH$_2$—CF$_2$—CF$_2$—CF$_2$—CF$_3$.

The weight average molecular weight (Mw) (based on the polystyrene-equivalent value determined by gel permeation chromatography) of the component (F) is preferably in a range of 1,000 to 50,000, more preferably in a range of 5,000 to 40,000, and most preferably in a range of 10,000 to 30,000. In a case where the weight average molecular weight is equal to or smaller than the upper limit value of this range, the resist composition exhibits sufficiently satisfactory solubility in a resist solvent to be used as a resist. On the other hand, in a case where the weight average molecular weight is equal to or larger than the lower limit value of this range, the water repellency of the resist film is excellent.

Further, the polydispersity (Mw/Mn) of the component (F) is preferably in a range of 1.0 to 5.0, more preferably in a range of 1.0 to 3.0, and most preferably in a range of 1.0 to 2.5.

In the resist composition according to the present embodiment, the component (F) may be used alone or in a combination of two or more kinds thereof.

In a case where the resist composition contains the component (F), the content of the component (F) to be used is typically at a proportion of 0.5 to 10 parts by mass, with respect to 100 parts by mass of the component (A1).

<<Organic Solvent Component (S)>>

The resist composition according to the present embodiment may be produced by dissolving the resist materials in an organic solvent component (hereinafter, referred to as a "component (S)").

The component (S) may be any organic solvent which can dissolve each of the components to be used to obtain a homogeneous solution, and any organic solvent can be appropriately selected from solvents for a chemically amplified resist composition, which are known in the related art, and then used.

Examples of the component (S) include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol, and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkyl ether (such as monomethyl ether, monoethyl ether, monopropyl ether or monobutyl ether) or monophenyl ether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzyl ether, cresylmethyl ether, diphenyl ether, dibenzyl ether, phenetole, butylphenyl ether, ethyl benzene, diethyl benzene, pentyl benzene, isopropyl benzene, toluene, xylene, cymene and mesitylene; and dimethylsulfoxide (DMSO).

In the resist composition according to the present embodiment, the component (S) may be used alone or as a mixed solvent of two or more kinds thereof. Among these, PGMEA, PGME, γ-butyrolactone, EL, and cyclohexanone are preferable.

Further, a mixed solvent obtained by mixing PGMEA with a polar solvent is also preferable as the component (S). The blending ratio (mass ratio) of the mixed solvent can be suitably determined, taking into consideration the compatibility of the PGMEA with the polar solvent, but is preferably in a range of 1:9 to 9:1 and more preferably in a range of 2:8 to 8:2.

More specifically, in a case where EL or cyclohexanone is blended as the polar solvent, the PGMEA:EL or cyclohexanone mass ratio is preferably in a range of 1:9 to 9:1 and more preferably in a range of 2:8 to 8:2. Alternatively, in a case where PGME is blended as the polar solvent, the PGMEA:PGME mass ratio is preferably in a range of 1:9 to 9:1, more preferably in a range of 2:8 to 8:2, and still more preferably in a range of 3:7 to 7:3. Furthermore, a mixed solvent of PGMEA, PGME, and cyclohexanone is also preferable.

Further, the component (S) is also preferably a mixed solvent of at least one selected from PGMEA and EL and γ-butyrolactone. In this case, as the mixing ratio, the mass ratio of the former to the latter is preferably in a range of 70:30 to 95:5.

The amount of the component (S) to be used is not particularly limited and is suitably set, depending on a thickness of a film to be coated, to a concentration at which the component (S) can be applied onto a substrate or the like. Generally, the component (S) is used such that the solid content concentration of the resist composition is in a range of 0.1% to 20% by mass and preferably in a range of 0.2% to 15% by mass.

As desired, other miscible additives can also be added to the resist composition according to the present embodiment. For example, for improving the performance of the resist film, an additive resin, a dissolution inhibitor, a plasticizer, a stabilizer, a colorant, a halation prevention agent, and a dye can be suitably contained therein.

After dissolving the resist material in the component (S), the resist composition according to the present embodiment may be subjected to removal of impurities and the like by using a porous polyimide membrane, a porous polyamide-imide membrane, or the like. For example, the resist composition may be filtered using a filter made of a porous polyimide membrane, a filter made of a porous polyamide-imide membrane, or a filter made of a porous polyimide membrane and a porous polyamideimide membrane. Examples of the porous polyimide membrane and the porous polyamideimide membrane include those described in Japanese Unexamined Patent Application, First Publication No. 2016-155121.

The resist composition according to the present embodiment described above contains a resin component (A1) having the above-described constitutional unit (a01).

The constitutional unit (a01) has an acid dissociable group represented by "—C($Ra^{02}$)($Ra^{03}$)—C≡C—$Ra^{01}$" in General Formula (a0-1). The acid dissociable group has a triple bond at the α-position of the tertiary carbon atom and has $Ra^{01}$ (a linear or branched hydrocarbon group) at the terminal of the triple bond. For this reason, the deprotection of the acid dissociable group by acid proceeds easily. On the other hand, in a case where the terminal is a hydrogen atom like in the acid dis sociable group in the related art, the deprotection by acid is difficult to proceed, and thus the lithography characteristics tend to deteriorate.

In addition, $Ra^{01}$ in the acid dissociable group is not a highly hydrophobic cyclic hydrocarbon group but a linear or branched hydrocarbon group, and thus the compatibility with the developing solution is high.

As described above, according to the resist composition according to the present embodiment, it is possible to improve all of the sensitivity, the CDU, and the resolution.

(Method of Forming Resist Pattern)

A method of forming a resist pattern according to the second aspect according to the present invention is a method including a step of forming a resist film on a support using the resist composition according to the first aspect of the present invention described above, a step of exposing the resist film, and a step of developing the exposed resist film to form a resist pattern.

Examples of one embodiment of such a method of forming a resist pattern include a method of forming a resist pattern carried out as described below.

First, the resist composition of the above-described embodiment is applied onto a support with a spinner or the like, and a baking (post-apply baking (PAB)) treatment is carried out, for example, at a temperature condition in a range of 80° C. to 150° C. for 40 to 120 seconds, preferably for 60 to 90 seconds to form a resist film.

Following the selective exposure carried out on the resist film by, for example, exposure through a mask (mask pattern) having a predetermined pattern formed on the mask by using a lithography apparatus such as an electron beam lithography apparatus or an EUV exposure apparatus, or direct irradiation of the resist film for drawing with an electron beam without using a mask pattern, baking treatment (post-exposure baking (PEB)) is carried out, for example, under a temperature condition in a range of 80° C. to 150° C. for 40 to 120 seconds and preferably 60 to 90 seconds.

Next, the resist film is subjected to a developing treatment. The developing treatment is carried out using an alkali developing solution in a case of an alkali developing process, and a developing solution containing an organic solvent (organic developing solution) in a case of a solvent developing process.

After the developing treatment, it is preferable to conduct a rinse treatment. As the rinse treatment, water rinsing using pure water is preferable in a case of an alkali developing process, and rinsing using a rinse liquid containing an organic solvent is preferable in a case of a solvent developing process.

In a case of a solvent developing process, after the developing treatment or the rinse treatment, the developing solution or the rinse liquid remaining on the pattern can be removed by a treatment using a supercritical fluid.

After the developing treatment or the rinse treatment, drying is conducted. As desired, baking treatment (post-baking) can be carried out following the developing treatment.

In this manner, a resist pattern can be formed.

The support is not specifically limited and a conventionally known support in the related art can be used. For example, substrates for electronic components, and such substrates having a predetermined wiring pattern formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the support, any support having the above-described substrate on which an inorganic and/or organic film is provided may be used. Examples of the inorganic film include an inorganic antireflection film (an inorganic BARC). Examples of the organic film include an organic antireflection film (organic BARC) and an organic film such as a lower-layer organic film used in a multilayer resist method.

Here, the multilayer resist method is a method in which at least one layer of an organic film (lower-layer organic film) and at least one layer of a resist film (upper-layer resist film) are provided on a substrate, and a resist pattern formed on the upper-layer resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is classified into a method in which a double-layer structure consisting of an upper-layer resist film and a lower-layer organic film is formed (double-layer resist method), and a method in which a multilayer structure having three or more layers consisting of an upper-layer resist film, a lower-layer organic film and one or more intermediate layers (thin metal film or the like) provided between the upper-layer resist film and the lower-layer organic film (triple-layer resist method).

The wavelength to be used for exposure is not particularly limited and the exposure can be carried out using radiation such as an ArF excimer laser, a KrF excimer laser, an $F_2$ excimer laser, an extreme ultraviolet ray (EUV), a vacuum ultraviolet ray (VUV), an electron beam (EB), an X-ray, or a soft X-ray. The resist composition is highly useful for a KrF excimer laser, an ArF excimer laser, EB, or EUV, and is more useful for an ArF excimer laser, EB, or EUV. That is, the method of forming a resist pattern according to the present embodiment is a method particularly useful in a case where the step of exposing the resist film includes an operation of exposing the resist film to an ArF excimer laser, an extreme ultraviolet ray (EUV), or an electron beam (EB).

The exposure method of the resist film may be a general exposure (dry exposure) carried out in air or an inert gas such as nitrogen, or liquid immersion exposure (liquid immersion lithography).

In liquid immersion lithography is an exposure method in which the region between the resist film and the lens at the lowermost position of the lithography apparatus is pre-filled with a solvent (liquid immersion medium) that has a larger refractive index than the refractive index of air, and the exposure (immersion exposure) is carried out in this state.

The liquid immersion medium is preferably a solvent that exhibits a refractive index larger than the refractive index of air but smaller than the refractive index of the resist film to be exposed. The refractive index of the solvent is not particularly limited as long as it satisfies the above-described requirements.

Examples of the solvent which exhibits a refractive index that is larger than the refractive index of air but smaller than the refractive index of the resist film include water, fluorine-based inert liquids, silicon-based solvents, and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$, or $C_5H_3F_7$ as the main component, and the boiling point is preferably in a range of 70° to 180° C. and more preferably in a range of 80° to 160° C. A fluorine-based inert liquid having a boiling point in the above-described range is advantageous in that removing the medium used in the liquid immersion after the exposure can be preferably carried out by a simple method.

The fluorine-based inert liquid is particularly preferably a perfluoroalkyl compound obtained by substituting all hydrogen atoms of an alkyl group with a fluorine atom. Examples of these perfluoroalkyl compounds include perfluoroalkyl ether compounds and perfluoroalkyl amine compounds.

Specifically, an example of a suitable perfluoroalkyl ether compound is perfluoro(2-butyl-tetrahydrofuran) (boiling point of 102° C.), and an example of a suitable perfluoroalkyl amine compound is perfluorotributyl amine (boiling point of 174° C.).

As the liquid immersion medium, water is preferable in terms of cost, safety, environment, and versatility.

Examples of the alkali developing solution used for a developing treatment in an alkali developing process include a 0.1% to 10% by mass aqueous solution of tetramethylammonium hydroxide (TMAH).

As the organic solvent contained in the organic developing solution, which is used for a developing treatment in a solvent developing process, any organic solvent capable of dissolving the component (A) (the component (A) prior to exposure) can be appropriately selected from the conventionally known organic solvents. Specific examples of the organic solvent include polar solvents such as a ketone-based solvent, an ester-based solvent, an alcohol-based solvent, a nitrile-based solvent, an amide-based solvent, and an ether-based solvent, and hydrocarbon-based solvents.

A ketone-based solvent is an organic solvent containing C—C(=O)—C in the structure thereof. An ester-based solvent is an organic solvent containing C—C(=O)—O—C in the structure thereof. An alcohol-based solvent is an organic solvent containing an alcoholic hydroxyl group in the structure thereof. The "alcoholic hydroxyl group" indicates a hydroxyl group bonded to a carbon atom of an aliphatic hydrocarbon group. A nitrile-based solvent is an organic solvent containing a nitrile group in the structure thereof. An amide-based solvent is an organic solvent containing an amide group in the structure thereof. An ether-based solvent is an organic solvent containing C—O—C in the structure thereof.

Some organic solvents have a plurality of the functional groups which characterize the above-described solvents in the structure thereof. In such a case, the organic solvent can be classified as any type of solvent having a functional group. For example, diethylene glycol monomethyl ether can be classified as an alcohol-based solvent or an ether-based solvent.

A hydrocarbon-based solvent consists of a hydrocarbon which may be halogenated and does not have any substituent other than a halogen atom. The halogen atom is preferably a fluorine atom.

Among the above, the organic solvent contained in the organic developing solution is preferably a polar solvent and more preferably a ketone-based solvent, an ester-based solvent, or a nitrile-based solvent.

Examples of ketone-based solvent include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetylcarbinol, acetophenone, methyl naphthyl ketone, isophorone, propylenecarbonate, γ-butyrolactone and methylamyl ketone (2-heptanone). Among these examples, the ketone-based solvent is preferably methylamyl ketone (2-heptanone).

Examples of the ester-based solvent include methyl acetate, butyl acetate, ethyl acetate, isopropyl acetate, amyl acetate, isoamyl acetate, ethyl methoxyacetate, ethyl ethoxyacetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate, and propyl-3-methoxypropionate. Among these, the ester-based solvent is preferably butyl acetate.

Examples of the nitrile-based solvent include acetonitrile, propionitrile, valeronitrile, and butyronitrile.

As desired, the organic developing solution may have a conventionally known additive blended. Examples of the additive include surfactants. The surfactant is not particularly limited, and for example, an ionic or non-ionic fluorine-based and/or a silicon-based surfactant can be used. The surfactant is preferably a non-ionic surfactant, and a non-ionic fluorine-based surfactant or a non-ionic silicon-based surfactant is more preferable.

In a case where a surfactant is blended, the amount of the surfactant to be blended is typically in a range of 0.001% to 5% by mass, preferably in a range of 0.005% to 2% by mass, and more preferably in a range of 0.01% to 0.5% by mass with respect to the total amount of the organic developing solution.

The developing treatment can be carried out by a conventionally known developing method. Examples thereof include a method in which the support is immersed in the developing solution for a predetermined time (a dip method), a method in which the developing solution is cast upon the surface of the support by surface tension and maintained for a predetermined time (a puddle method), a method in which the developing solution is sprayed onto the surface of the support (spray method), and a method in which a developing solution is continuously ejected from a developing solution ejecting nozzle and applied onto a support which is scanned at a constant rate while being rotated at a constant rate (dynamic dispense method).

As the organic solvent contained in the rinse liquid used in the rinse treatment after the developing treatment in a case of a solvent developing process, an organic solvent hardly dissolving the resist pattern can be appropriately selected and used, among the organic solvents mentioned as organic solvents that are used for the organic developing solution. In general, at least one kind of solvent selected from the group consisting of a hydrocarbon-based solvent, a ketone-based solvent, an ester-based solvent, an alcohol-based solvent, an amide-based solvent, and an ether-based solvent is used. Among these, at least one kind of solvent selected from the group consisting of a hydrocarbon-based solvent, a ketone-based solvent, an ester-based solvent, an alcohol-based solvent, and an amide-based solvent is preferable, at least one kind of solvent selected from the group consisting of an alcohol-based solvent and an ester-based solvent is more preferable, and an alcohol-based solvent is particularly preferable.

The alcohol-based solvent used for the rinse liquid is preferably a monohydric alcohol of 6 to 8 carbon atoms, and the monohydric alcohol may be linear, branched, or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol, and benzyl alcohol. Among these, 1-hexanol, 2-heptanol, and 2-hexanol are preferable, and 1-hexanol and 2-hexanol are more preferable.

As the organic solvent, one kind of solvent may be used alone, or two or more kinds of solvents may be used in combination. Further, an organic solvent other than the above-described examples or water may be mixed thereto. However, in consideration of the development characteristics, the amount of water to be blended in the rinse liquid is preferably 30% by mass or less, more preferably 10% by mass or less, still more preferably 5% by mass or less, and particularly preferably 3% by mass or less with respect to the total amount of the rinse liquid.

A conventionally known additive can be blended with the rinse liquid as necessary. Examples of the additive include surfactants. Examples of the surfactant include the same ones as those described above, the surfactant is preferably a non-ionic surfactant and more preferably a non-ionic fluorine-based surfactant or a non-ionic silicon-based surfactant.

In a case where a surfactant is blended, the amount of the surfactant to be blended is typically in a range of 0.001% to 5% by mass, preferably in a range of 0.005% to 2% by mass, and more preferably in a range of 0.01% to 0.5% by mass with respect to the total amount of the rinse liquid.

The rinse treatment using a rinse liquid (washing treatment) can be carried out by a conventionally known rinse method. Examples of the rinse treatment method include a method in which the rinse liquid is continuously ejected and applied onto the support while rotating it at a constant rate (rotational coating method), a method in which the support is immersed in the rinse liquid for a predetermined time (dip method), and a method in which the rinse liquid is sprayed onto the surface of the support (spray method).

According to the method of forming a resist pattern according to the present embodiment described above, since the resist composition according to the embodiment described above is used, it is possible to achieve high sensitivity and form a resist pattern having good CDU and good resolution.

(Compound)

The third aspect of the present invention is a compound represented by General Formula (a0-1).

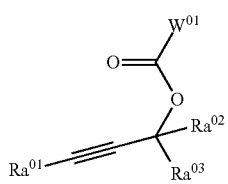

(a0-1)

[In the formula, $W^{01}$ represents a polymerizable group-containing group. $Ra^{01}$ represents a linear or branched hydrocarbon group. $Ra^{02}$ and $Ra^{03}$ each independently represent a hydrocarbon group which may have a substituent.]

The compound represented by General Formula (a0-1) according to the present embodiment is the same as the compound represented by General Formula (a0-1) in the resist composition according to the first aspect of the present invention.

The compound according to the present embodiment is preferably a compound represented by General Formula (a01-1m).

(a01-1m)

[In the formula, $R^{000}$ represents a hydrogen atom, an alkyl group having 1 to 5 carbon atoms, or a halogenated alkyl group having 1 to 5 carbon atoms. $Va^{01}$ represents a divalent linking group. $n_{a01}$ represents an integer in a range of 0 to 2. $Ra^{001}$ to $Ra^{003}$ each independently represent a linear or branched alkyl group.]

$Va^{01}$, $n_{a01}$, and $Ra^{001}$ to $Ra^{003}$ in General Formulae (a01-1m) are each the same as $Va^{01}$, $n_{a01}$, and $Ra^{001}$ to $Ra^{003}$ in General Formulae (a01-1).

Examples of $R^{000}$ in General Formula (a01-1m) include the same ones as R in General Formula (a01-1), and among them, a hydrogen atom or a methyl group is preferable.

Specific examples of the preferred compound according to the present embodiment are shown below.

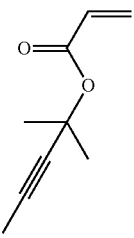

(a01-1m-1)

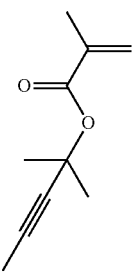

(a01-1m-2)

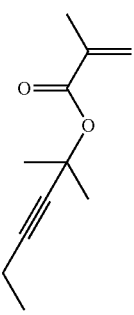

(a01-1m-3)

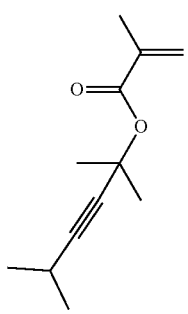

(a01-1m-4)

(a01-1m-5)

(a01-1m-6)

(a01-1m-7)

(a01-1m-8)

(a01-1m-9)

(a01-1m-10)

(a01-1m-11)

(a01-1m-12)

(a01-1m-13)

(a01-1m-14)
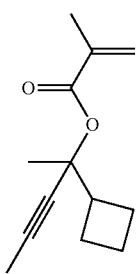
(a01-1m-15)
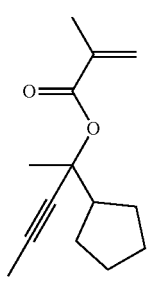
(a01-1m-16)
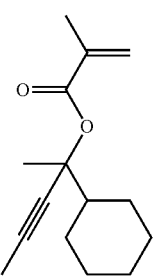
(a01-1m-17)
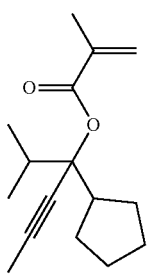
(a01-1m-18)
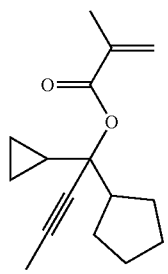
(a01-1m-19)
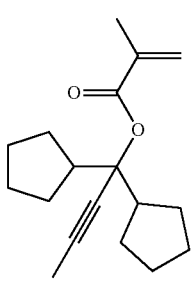
(a01-1m-20)
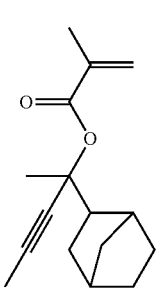
(a01-1m-21)
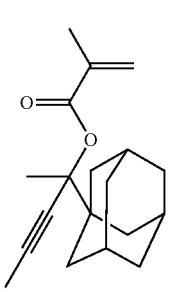
(a01-1m-22)
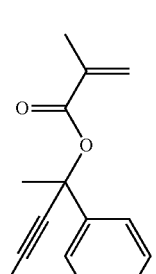
(a01-1m-23)
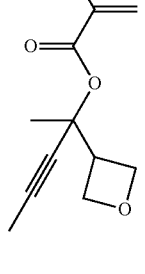

(a01-1m-24)
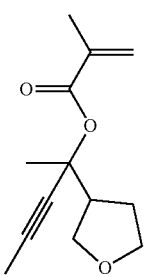

(a01-1m-25)
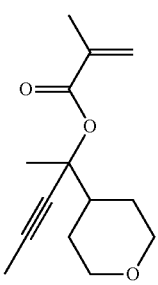

(a01-1m-26)
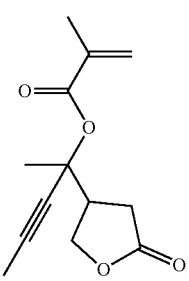

(a01-1m-27)
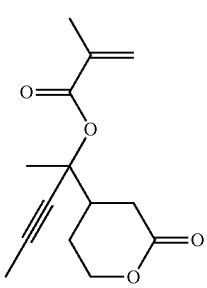

(a01-1m-28)
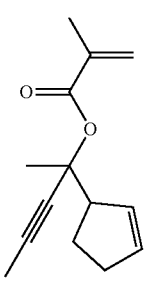

(a01-1m-29)

(a01-1m-30)

Among the above, the compound according to the present embodiment is preferably a compound represented by any one of General Formulae (a01-1m-1) to (a01-1m-12), more preferably a compound represented by any one of General Formulae (a01-1m-1) to (a01-1m-7) and (a01-1m-10) to (a01-1m-12), and still more preferably a compound represented by any one of General Formulae (a01-1m-2) to (a01-1m-4) and (a01-1m-7).

(Method of Producing Compound)

The compound according to the present embodiment can be produced, for example, by a method having the following steps (i) and (ii).

Step (i);

The step (i) is a step of reacting, in a reaction solvent, a compound (K1) represented by General Formula (K-1) with a compound (G1) represented by General Formula (G-1) or a compound (L1) represented by General Formula (L-1) to obtain a compound (Alc1) represented by General Formula (Alc-1).

[In the formula, $Ra^{01}$ represents a linear or branched hydrocarbon group. $Ra^{02}$ and $Ra^{03}$ each independently represent a hydrocarbon group which may have a substituent. $X^{01}$ represents a halogen atom.]

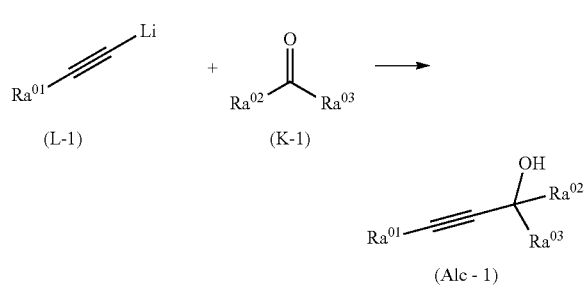

(L-1)   (K-1)   (Alc - 1)

[In the formula, $Ra^{01}$ represents a linear or branched hydrocarbon group. $Ra^{02}$ and $Ra^{03}$ each independently represent a hydrocarbon group which may have a substituent.]

$Ra^{01}$ to $Ra^{03}$ in the above formula are each the same as $Ra^{01}$ to $Ra^{03}$ in General Formula (a0-1).

$X^{01}$ in the formula represents a halogen atom and preferably a bromine atom.

The compound (L1) can be obtained, for example, by reacting a compound (L1) precursor in which the Li atom of the compound represented by General Formula (L-1) is a hydrogen atom with an organic lithium compound.

Specific examples of the organic lithium compound include methyl lithium, ethyl lithium, phenyl lithium, n-butyl lithium, sec-butyl lithium, and tert-butyl lithium.

The reaction solvent may be any solvent as long as it can dissolve the compound (K1) and the compound (G1), or the compound (K1) and the compound (L1) and does not react with these compounds, and examples thereof include dichloromethane, dichloroethane, chloroform, tetrahydrofuran, N,N-dimethylformamide, acetonitrile, propionitrile, N,N'-dimethylacetamide, and dimethylsulfoxide.

In the step (i), acids such as hydrochloric acid, nitric acid, sulfuric acid, formic acid, oxalic acid, and acetic acid may be used.

The reaction temperature in the step (i) is preferably in a range of −80° C. to 40° C. and more preferably in a range of −20° C. to 20° C.

The reaction time of the step (i) varies depending on the reactivity between the compound (K1) and the compound (G1) or the compound (L1) and the reaction temperature; however, the reaction time is preferably in a range of 0.5 to 24 hours and preferably in a range of 0.5 to 3 hours.

Step (ii);

The step (ii) is a step of reacting, in a reaction solvent, a compound (Ala) represented by General Formula (Alc-1) with a compound (Car1) represented by General Formula (Car-1) to obtain a compound represented by General Formula (a0-1).

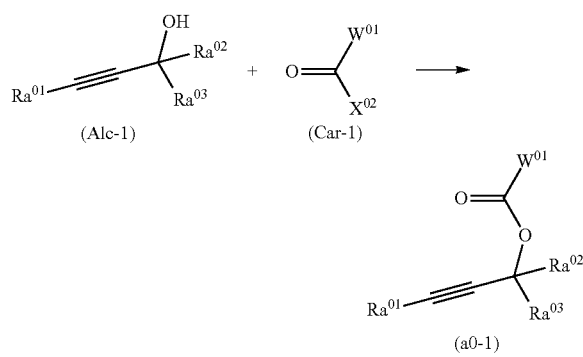

(Alc-1)   (Car-1)   (a0-1)

[In the formula, $Ra^{01}$ represents a linear or branched hydrocarbon group. $Ra^{02}$ and $Ra^{03}$ each independently represent a hydrocarbon group which may have a substituent. $W^{01}$ represents a polymerizable group-containing group. $X^{02}$ represents a halogen atom.]

$Ra^{01}$ to $Ra^{03}$ and $W^{01}$ in the above formula are each the same as $Ra^{01}$ to $Ra^{03}$ and $W^{01}$ in General Formula (a0-1).

$X^{02}$ in the formula represents a halogen atom and preferably a chlorine atom.

The reaction solvent may be any solvent as long as it can dissolve the compound (Alc1) and the compound (Car1) and does not react with these compounds, and examples thereof include dichloromethane, dichloroethane, chloroform, tetrahydrofuran, N,N-dimethylformamide, acetonitrile, propionitrile, N,N'-dimethylacetamide, and dimethylsulfoxide.

In the step (ii), bases such as triethylamine, pyridine, and 4-dimethylaminopyridine may be used.

The reaction temperature in the step (ii) is preferably in a range of −40° C. to 80° C. and more preferably in a range of −20° C. to 60° C.

The reaction time of the step (ii) varies depending on the reactivity between the compound (Alc1) and the compound (Car1) and the reaction temperature; however, the reaction time is preferably in a range of 0.5 to 24 hours and preferably in a range of 0.5 to 3 hours.

The compound represented by General Formula (a0-1), which is obtained in the step (ii), may be isolated and purified. Conventionally known methods in the related art can be used for isolation and purification, and for example, concentration, solvent extraction, distillation, crystallization, recrystallization, chromatography, and the like can be appropriately combined and used.

The structure of the compound represented by General Formula (a0-1), which is obtained as described above, can be identified by general organic analysis methods such as 1H-nuclear magnetic resonance (NMR) spectroscopy, 13C-NMR spectroscopy, infrared absorption (IR) spectroscopy, mass spectrometry (MS), elemental analysis, and X-ray crystal diffraction.

The compound according to the present embodiment, which is described above, is useful for producing a resin according to the fourth aspect described later.

The fourth aspect of the present invention is a resin having a constitutional unit derived from a compound represented by General Formula (a0-1).

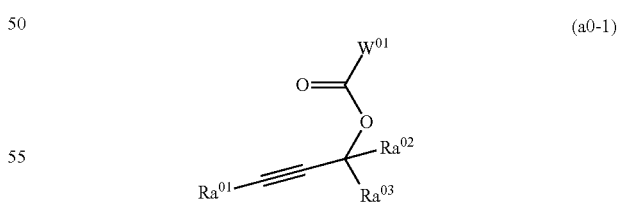

(a0-1)

[In the formula, represents a polymerizable group-containing group. $Ra^{01}$ represents a linear or branched hydrocarbon group. $Ra^{02}$ and $Ra^{03}$ each independently represent a hydrocarbon group which may have a substituent.]

The resin according to the fourth aspect of the present invention is the same as the above-described component (A1).

The resin according to the fourth aspect of the present invention is a resin useful for a resist composition.

EXAMPLES

Hereinafter, the present invention will be described in more detail based on Examples, but the present invention is not limited to these Examples.

Synthesis Example of Compound

Synthesis Example of Compound (m-a0-1)

15.0 g of 2-methyl-3-pentyn-2-ol and 23.2 g of triethylamine were dissolved in 190 g of dichloromethane, and a solution prepared by dissolving 19.2 g of methacrylic acid chloride in 40 g of THF was added dropwise thereto at a temperature of 5° C. or lower. After further stirring under ice cooling for 1 hour, 220 g of pure water was added dropwise to the reaction solution, and after stirring, the aqueous layer was removed. The solvent of the organic layer was distilled off, and further distillation purification was carried out to obtain a compound (m-a0-1).

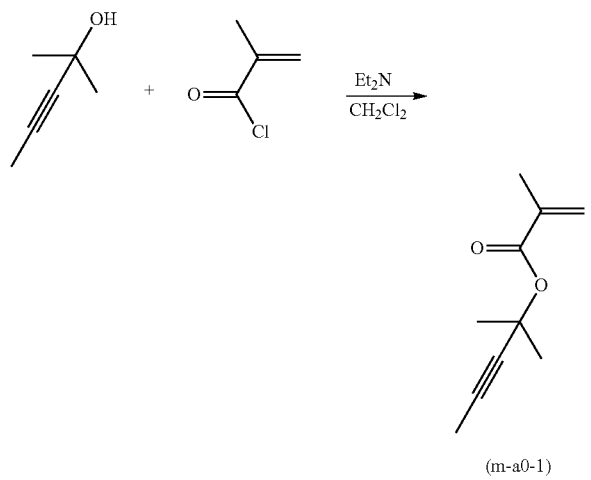

(m-a0-1)

The obtained compound (m-a0-1) was subjected to NMR measurement (CDCl$_3$), and the structure thereof was identified from the following results.

δ (ppm)=6.05-6.06 (s, C═CH, 1H), 5.54-5.50 (m, C═CH, 1H), 1.91-1.94 (s, CH$_3$, 3H), 1.82-1.85 (s, CH$_3$, 3H), 1.67-1.70 (s, CH$_3$, 6H)

Synthesis Example of Compound (m-a0-2)

A compound (m-a0-2) was obtained in the same manner as in Synthesis Example of the compound (m-a0-1) except that 2-methyl-3-pentyn-2-ol was changed to 17.1 g of 2-methyl-3-hexyn-2-ol.

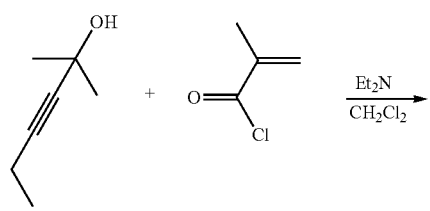

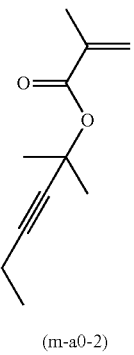

(m-a0-2)

The obtained compound (m-a0-2) was subjected to NMR measurement (CDCl$_3$), and the structure thereof was identified from the following results.

δ(ppm)=6.03-6.05 (s, C═CH, 1H), 5.54-5.50 (m, C═CH, 1H), 1.96-2.01 (q, CH$_2$, 2H), 1.90-1.93 (s, CH$_3$, 3H), 1.66-1.69 (s, CH$_3$, 6H), 1.21-1.24 (t, CH$_3$, 3H)

Synthesis Example of Compound (m-a0-3)

24 g of methyl vinyl ketone was added dropwise to 688 mL of 1-propynyl magnesium bromide (a THF solution, 0.5 mol/L) at a temperature of −20° C. or lower, and stirring was carried out for 1 hour. Then, a solution prepared by dissolving 17.9 g of methacrylic acid chloride in 36.0 g of THF was added dropwise thereto. After further stirring under ice cooling for 1 hour, 300 g of pure water was added dropwise to the reaction solution, and extraction was carried out with 300 g of heptane. The solvent of the organic layer was distilled off, and further distillation purification was carried out to obtain a compound (m-a0-3).

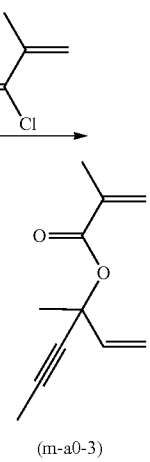

(m-a0-3)

The obtained compound (m-a0-3) was subjected to NMR measurement (CDCl$_3$), and the structure thereof was identified from the following results.

δ(ppm)=6.1-6.3 (m, C═CH, 1H), 6.03-6.05 (s, C═CH, 1H), 5.55-5.52 (m, C═CH, 1H), 5.21-5.23 (d, C═CH$_2$, 1H), 5.12-5.16 (d, C═CH$_2$, 1H), 1.91-1.94 (s, CH$_3$, 3H), 1.82-1.85 (s, CH$_3$, 3H), 1.69-1.72 (s, CH$_3$, 3H)

Synthesis Example of Compound (m-a0-4)

A compound (m-a0-4) was obtained in the same manner as in Synthetic Example of the compound (m-a0-3) except that methyl vinyl ketone was changed to 29.7 g of 3-methyl-2-butanone.

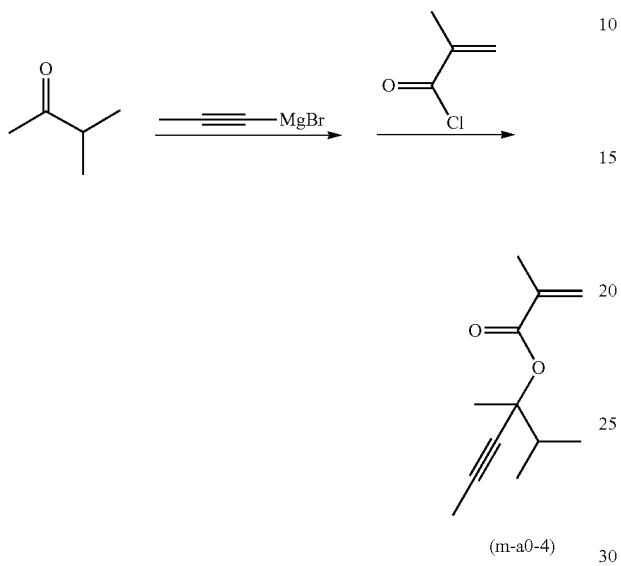

(m-a0-4)

The obtained compound (m-a0-4) was subjected to NMR measurement (CDCl$_3$), and the structure thereof was identified from the following results.

δ (ppm)=6.04-6.07 (s, C=CH, 1H), 5.54-5.50 (m, C=CH, 1H), 2.76-2.80 (m, CH, 1H), 1.91-1.94 (s, CH$_3$, 3H), 1.82-1.85 (s, CH$_3$, 3H), 1.72-1.75 (s, CH$_3$, 3H), 0.91-0.94 (d, CH$_3$, 6H)

Synthesis Example of Compound (m-a0-5)

10 g of isopropyl acetylene was dissolved in 40 g of THF, cooled to −78° C., and 70 mL of n-BuLi (a hexane solution, 2.4 mol/L) was added dropwise thereto. The temperature was raised to −20° C., and stirring was carried out for 1 hour. Then, 8.9 g of acetone was added dropwise thereto, and stirring was carried out for 5 hours. Then, a solution prepared by dissolving 19.2 g of methacrylic acid chloride in 38.0 g of THF was added dropwise thereto. After further stirring under ice cooling for 1 hour, 300 g of pure water was added dropwise to the reaction solution, and extraction was carried out with 300 g of heptane. The solvent of the organic layer was distilled off, and further distillation purification was carried out to obtain a compound (m-a0-5).

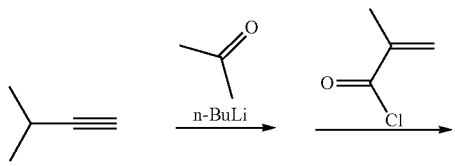

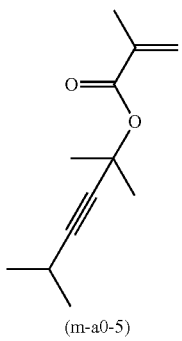

(m-a0-5)

The obtained compound (m-a0-5) was subjected to NMR measurement (CDCl$_3$), and the structure thereof was identified from the following results.

δ (ppm)=6.06-6.08 (s, C=CH, 1H), 5.56-5.52 (m, C=CH, 1H), 2.50-2.54 (m, CH, 1H), 1.90-1.93 (s, CH$_3$, 3H), 1.66-1.69 (s, CH$_3$, 6H), 1.32-1.26 (d, CH$_3$, 6H)

Synthesis Example of Compound (m-a0-6)

A compound (m-a0-6) was obtained in the same manner as in Synthetic Example of the compound (m-a0-3) except that methyl vinyl ketone was changed to 41.4 g of acetophenone.

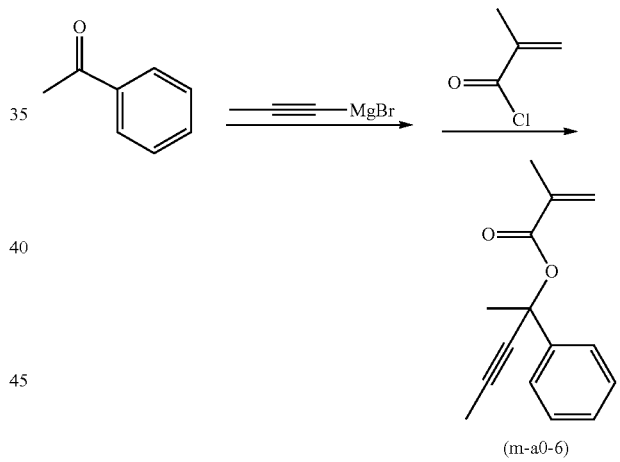

(m-a0-6)

The obtained compound (m-a0-6) was subjected to NMR measurement (CDCl$_3$), and the structure thereof was identified from the following results.

δ (ppm)=7.34-7.40 (m, ArH, 4H), 7.26-7.28 (m, ArH, 1H), 5.99-6.02 (s, C=CH, 1H), 5.54-5.58 (m, C=CH, 1H), 1.91-1.94 (s, CH$_3$, 3H), 1.82-1.85 (s, CH$_3$, 3H), 1.62-1.76 (s, CH$_3$, 3H)

Synthesis Example 1 of Polymeric Compound

Synthesis Example of Polymeric Compound (A-1)

17.6 g of a monomer (m-a0-1), 10.0 g of a monomer (m-a10-1 pre), and 3.86 g of azobis (isobutyric acid) dimethyl (V-601) as a polymerization initiator were dissolved in 43.6 g of methyl ethyl ketone (MEK) to prepare a dropping solution. 11.6 g of MEK was added to a three-necked flask connected with a thermometer, a reflux tube, and a nitrogen feeding tube, heated to 85° C. in a nitrogen atmosphere, and the above dropping solution was added dropwise over 4 hours. After completion of the dropwise addition, the reaction solution was stirred at 85° C. for 1 hour. Then, the reaction solution was cooled to room temperature. Next, 12.2 g of acetic acid and 175 g of methanol were added to the obtained polymerization solution, and a deprotection reaction was carried out at 30° C. for 8 hours. After completion of the reaction, the obtained reaction solution was precipitated in 2,600 g of heptane, followed by washing. The obtained white solid substance was filtered and subjected to drying under reduced pressure overnight to obtain the target polymeric compound (A-1).

above and compounds (m-a10-1 pre), (m-a10-2 pre), (m-a10-3 pre), (m-a1-1) to (m-a1-4), and (m-a8), (m-a2), and (m-a3) shown below.

With respect to the obtained polymeric compounds, the copolymerization composition ratio (the ratio (molar ratio) between constitutional units, each of which is derived from a monomer) in the polymeric compound, which was determined by $^{13}$C-NMR, the weight average molecular weight (Mw) in terms of standard polystyrene equivalent value, which was determined by GPC measurement, and the polydispersity (Mw/Mn) are shown together in Table 1.

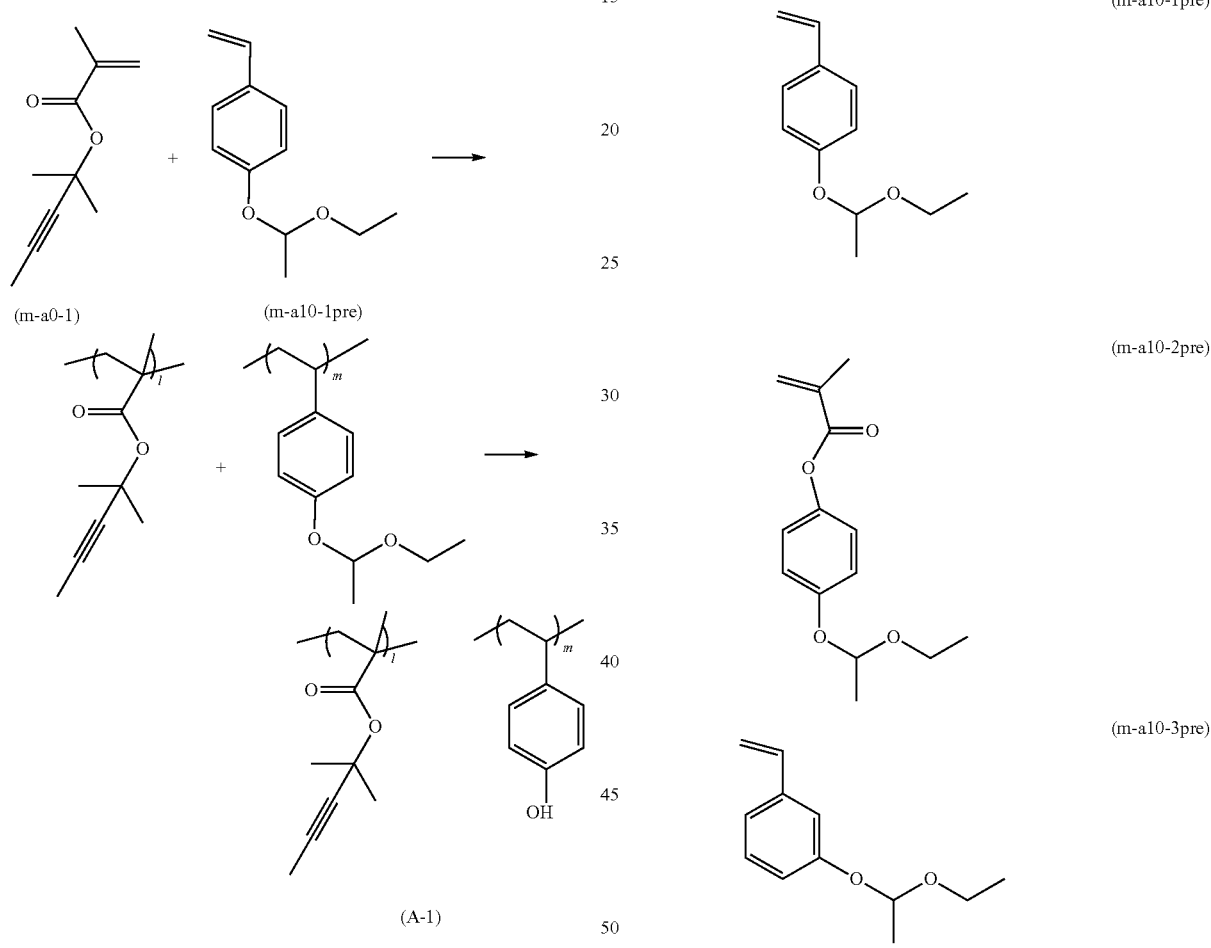

As a result of a GPC measurement to determine the weight average molecular weight (Mw) in terms of standard polystyrene equivalent value, the obtained polymeric compound (A-1) had a weight average molecular weight of 5,500 and a polydispersity (Mw/Mn) of 1.67. The copolymerization composition ratio (the ratio (the molar ratio) between constitutional units each derived from the monomer) determined by $^{13}$C-NMR was 1/m=50/50.

Synthesis Examples 2 to 25 of Polymeric Compounds

Polymeric compounds (A-2) to (A-25) having composition ratios shown in Table 1 were synthesized in the same manner as in Synthesis Example 1 of the polymeric compound by using the compounds (m-a0-1) to (m-a0-6) shown (m-a2)
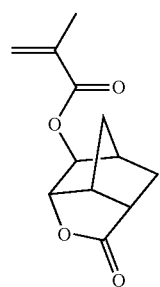
(m-a3)
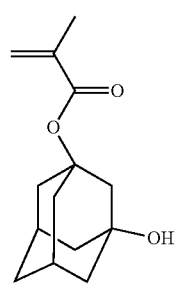
(m-a1-1)
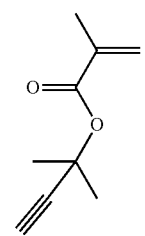
(m-a1-2)
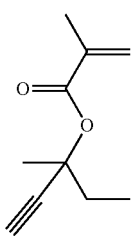
(m-a1-3)
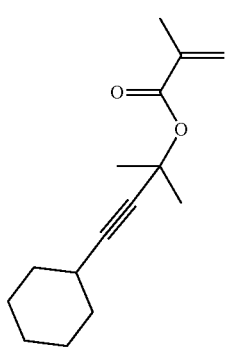
(m-a1-4)
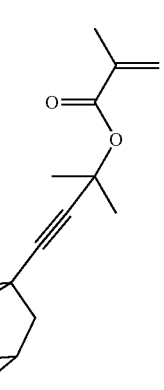
(A-1)
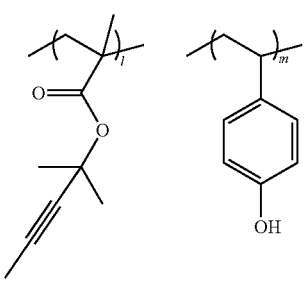
(A-2)
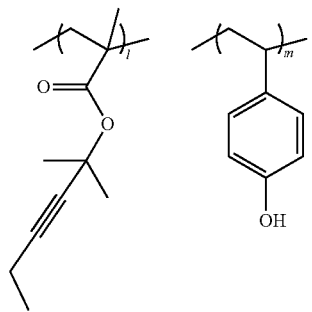
(A-3)
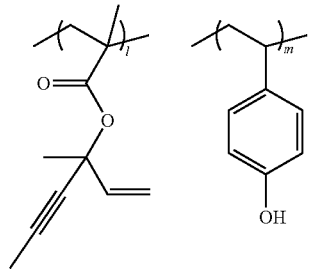
(A-4)
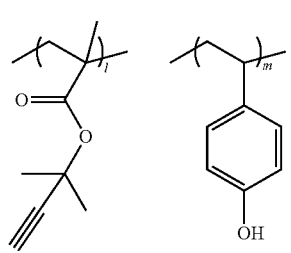

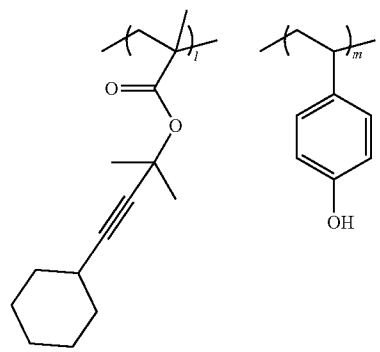
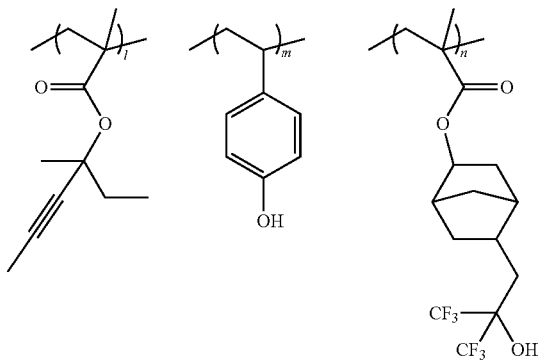
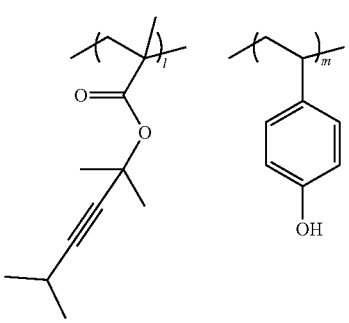
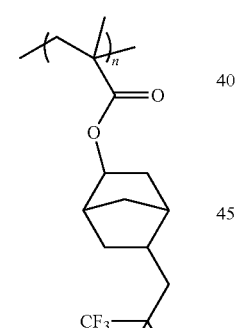
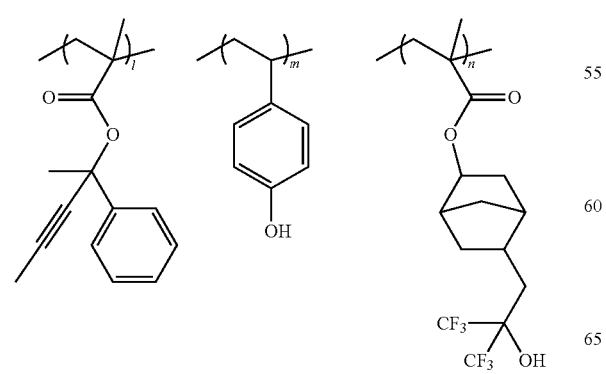

(A-13)
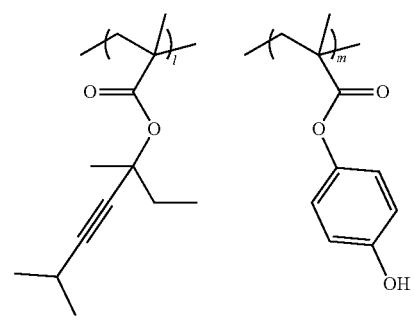
(A-14)
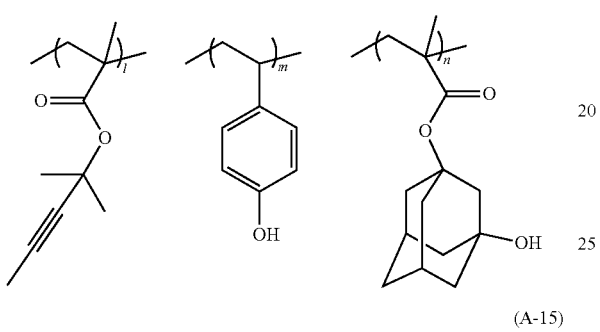
(A-15)
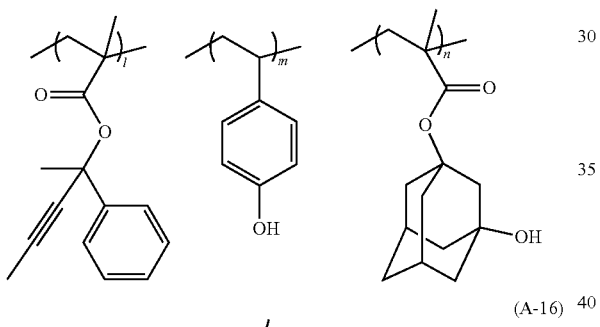
(A-16)
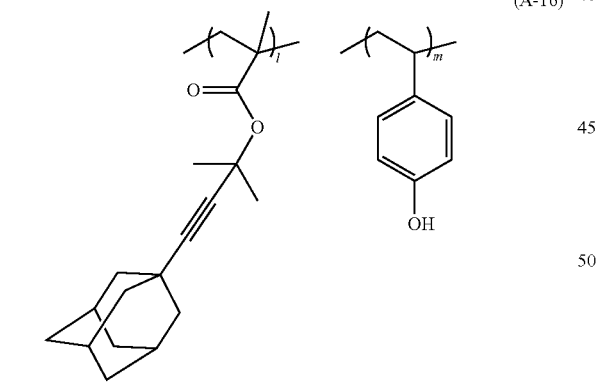
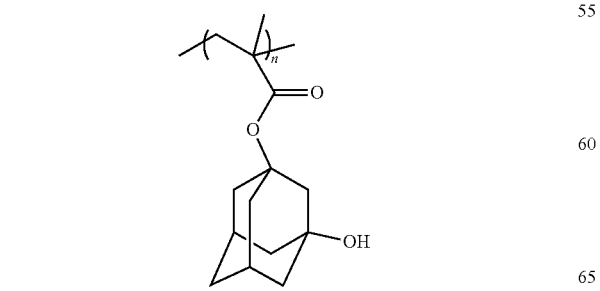
(A-17)
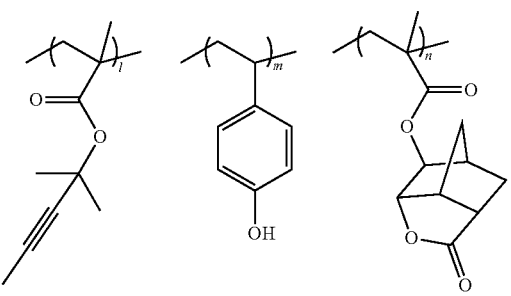
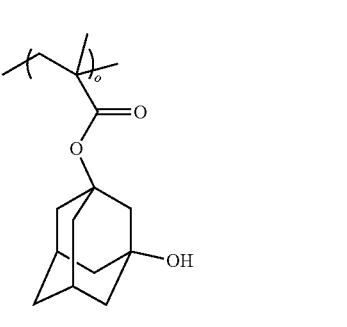
(A-18)
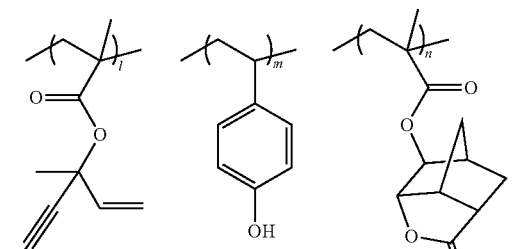
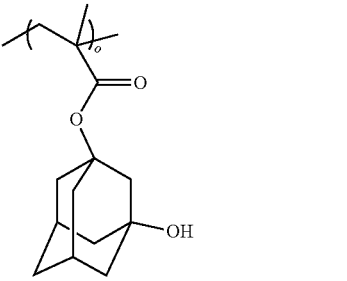
(A-19)
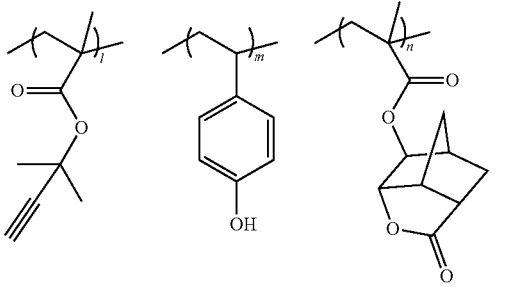

-continued
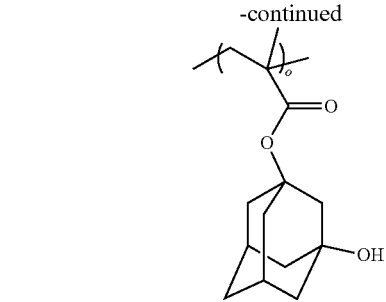
(A-20)
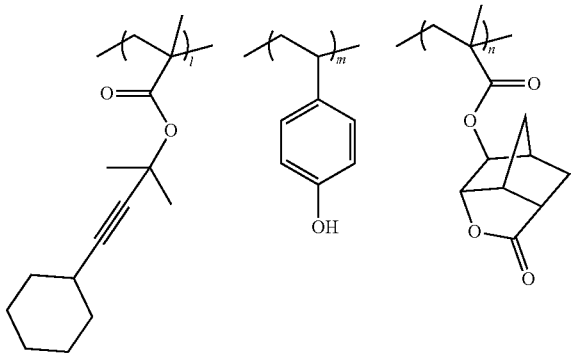
(A-21)
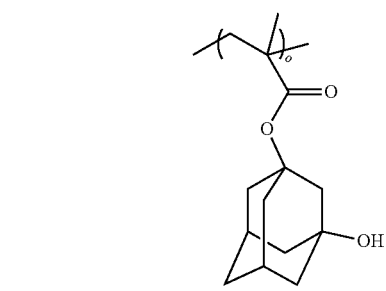
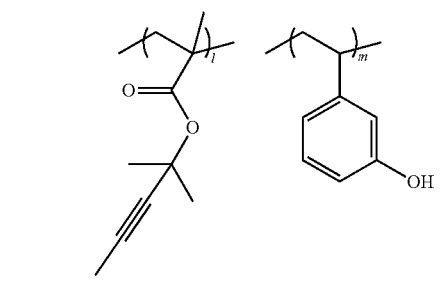
(A-22)
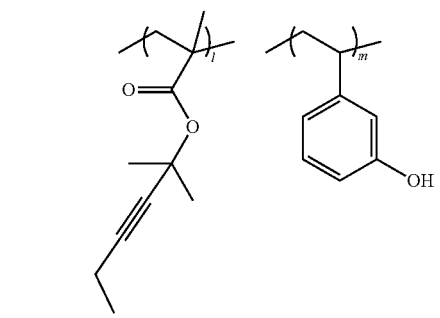
-continued
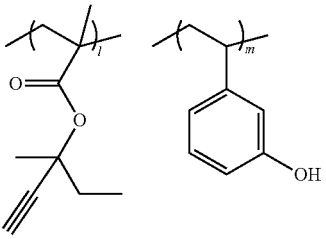
(A-23)
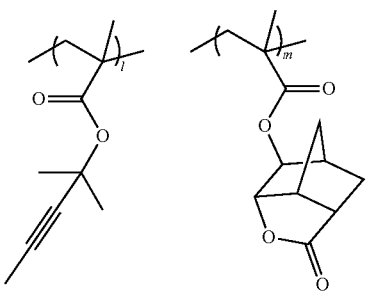
(A-24)
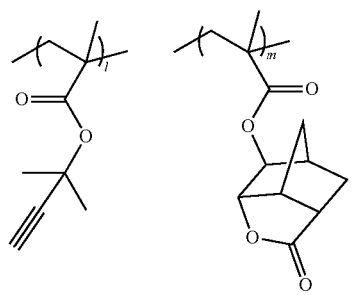
(A-25)
It is noted the constitutional units each represented by Chemical Formulae (a10-1-1), (a10-1-2), and (a10-1-3), which constitute the above-described copolymer, are constitutional units derived from the monomers each represented by Chemical Formula (m-a10-1 pre), (m-a10-2 pre), and (m-a10-3 pre).
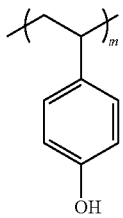
(a10-1-1)
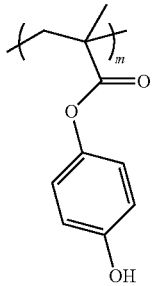
(a10-1-2)

-continued

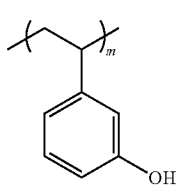

(a10-1-3)

TABLE 1

| Polymeric compound | | Copolymerization composition ratio (molar ratio) in polymeric compound | Weight average molecular weight (Mw) | Poly-dispersity (Mw/Mn) |
|---|---|---|---|---|
| Synthesis Example 1 | (A-1) | l/m = 50/50 | 5500 | 1.67 |
| Synthesis Example 2 | (A-2) | l/m = 50/50 | 5600 | 1.57 |
| Synthesis Example 3 | (A-3) | l/m = 50/50 | 5500 | 1.55 |
| Synthesis Example 4 | (A-4) | l/m = 50/50 | 5900 | 1.76 |
| Synthesis Example 5 | (A-5) | l/m = 50/50 | 5800 | 1.65 |
| Synthesis Example 6 | (A-6) | l/m/n = 40/50/10 | 6500 | 1.51 |
| Synthesis Example 7 | (A-7) | l/m/n = 40/50/10 | 6100 | 1.61 |
| Synthesis Example 8 | (A-8) | l/m/n = 40/50/10 | 6900 | 1.70 |
| Synthesis Example 9 | (A-9) | l/m/n = 40/50/10 | 6500 | 1.62 |
| Synthesis Example 10 | (A-10) | l/m/n = 40/50/10 | 6100 | 1.70 |
| Synthesis Example 11 | (A-11) | l/m = 60/40 | 8200 | 1.68 |
| Synthesis Example 12 | (A-12) | l/m = 60/40 | 8500 | 1.59 |
| Synthesis Example 13 | (A-13) | l/m = 60/40 | 8100 | 1.62 |
| Synthesis Example 14 | (A-14) | l/m/n = 40/50/10 | 5800 | 1.67 |
| Synthesis Example 15 | (A-15) | l/m/n = 40/50/10 | 5900 | 1.51 |
| Synthesis Example 16 | (A-16) | l/m/n = 40/50/10 | 5300 | 1.69 |
| Synthesis Example 17 | (A-17) | l/m/n/o = 40/30/20/10 | 7200 | 1.71 |
| Synthesis Example 18 | (A-18) | l/m/n/o = 40/30/20/10 | 8000 | 1.80 |
| Synthesis Example 19 | (A-19) | l/m/n/o = 40/30/20/10 | 7400 | 1.73 |
| Synthesis Example 20 | (A-20) | l/m/n/o = 40/30/20/10 | 7800 | 1.73 |
| Synthesis Example 21 | (A-21) | l/m = 45/55 | 5500 | 1.69 |
| Synthesis Example 22 | (A-22) | l/m = 45/55 | 5800 | 1.68 |
| Synthesis Example 23 | (A-23) | l/m = 45/55 | 5800 | 1.69 |
| Synthesis Example 24 | (A-24) | l/m = 60/40 | 7200 | 1.88 |
| Synthesis Example 25 | (A-25) | l/m = 60/40 | 7800 | 1.74 |

<Preparation of Resist Composition>

Examples 1 to 20 and Comparative Examples 1 to 10

Each of the components shown in Tables 2 and 3 was mixed and dissolved to prepare a resist composition of each Example.

TABLE 2

| | Component (A) | Component (B) | Component (D) | Component (S) |
|---|---|---|---|---|
| Example 1 | (A)-1 [100] | (B)-1 [25.0] | (D)-1 [5.0] | (S)-1 [8000] |
| Example 2 | (A)-1 [100] | (B)-2 [28.0] | (D)-1 [5.0] | (S)-1 [8000] |
| Example 3 | (A)-1 [100] | (B)-3 [24.0] | (D)-1 [5.0] | (S)-1 [8000] |
| Example 4 | (A)-2 [100] | (B)-1 [25.0] | (D)-1 [5.0] | (S)-1 [8000] |
| Example 5 | (A)-3 [100] | (B)-1 [25.0] | (D)-1 [5.0] | (S)-1 [8000] |
| Comparative Example 1 | (A)-4 [100] | (B)-1 [25.0] | (D)-1 [5.0] | (S)-1 [8000] |
| Comparative Example 2 | (A)-5 [100] | (B)-1 [25.0] | (D)-1 [5.0] | (S)-1 [8000] |
| Example 6 | (A)-6 [100] | (B)-1 [25.0] | (D)-1 [5.0] | (S)-1 [8000] |
| Example 7 | (A)-7 [100] | (B)-1 [25.0] | (D)-1 [5.0] | (S)-1 [8000] |
| Example 8 | (A)-8 [100] | (B)-1 [25.0] | (D)-1 [5.0] | (S)-1 [8000] |
| Comparative Example 3 | (A)-9 [100] | (B)-1 [25.0] | (D)-1 [5.0] | (S)-1 [8000] |
| Comparative Example 4 | (A)-10 [100] | (B)-1 [25.0] | (D)-1 [5.0] | (S)-1 [8000] |
| Example 9 | (A)-11 [100] | (B)-1 [25.0] | (D)-1 [5.0] | (S)-1 [8000] |
| Example 10 | (A)-12 [100] | (B)-1 [25.0] | (D)-1 [5.0] | (S)-1 [8000] |
| Comparative Example 5 | (A)-13 [100] | (B)-1 [25.0] | (D)-1 [5.0] | (S)-1 [8000] |

TABLE 3

| | Component (A) | Component (B) | Component (D) | Component (S) |
|---|---|---|---|---|
| Example 11 | (A)-14 [100] | (B)-1 [25.0] | (D)-1 [5.0] | (S)-1 [8000] |
| Example 12 | (A)-15 [100] | (B)-1 [25.0] | (D)-1 [5.0] | (S)-1 [8000] |
| Example 13 | (A)-14 [100] | (B)-2 [28.0] | (D)-1 [5.0] | (S)-1 [8000] |
| Comparative Example 6 | (A)-16 [100] | (B)-1 [25.0] | (D)-1 [5.0] | (S)-1 [8000] |
| Example 14 | (A)-17 [100] | (B)-1 [25.0] | (D)-1 [5.0] | (S)-1 [8000] |
| Example 15 | (A)-18 [100] | (B)-1 [25.0] | (D)-1 [5.0] | (S)-1 [8000] |
| Example 16 | (A)-18 [100] | (B)-3 [24.0] | (D)-1 [5.0] | (S)-1 [8000] |
| Comparative Example 7 | (A)-19 [100] | (B)-1 [25.0] | (D)-1 [5.0] | (S)-1 [8000] |
| Comparative Example 8 | (A)-20 [100] | (B)-1 [25.0] | (D)-1 [5.0] | (S)-1 [8000] |
| Example 17 | (A)-21 [100] | (B)-1 [25.0] | (D)-1 [5.0] | (S)-1 [8000] |
| Example 18 | (A)-22 [100] | (B)-1 [25.0] | (D)-1 [5.0] | (S)-1 [8000] |
| Comparative Example 9 | (A)-23 [100] | (B)-1 [25.0] | (D)-1 [5.0] | (S)-1 [8000] |
| Example 19 | (A)-24 [100] | (B)-1 [25.0] | (D)-1 [5.0] | (S)-1 [8000] |
| Example 20 | (A)-24 [100] | (B)-3 [24.0] | (D)-1 [5.0] | (S)-1 [8000] |
| Comparative Example 10 | (A)-25 [100] | (B)-1 [25.0] | (D)-1 [5.0] | (S)-1 [8000] |

(A)-1 to (A)-25: The polymeric compounds (A-1) to (A-25) described above.

(B)-1 to (B)-3: Acid generators composed of compounds each represented by Chemical Formulae (B-1) to (B-3).

(D)-1: An acid diffusion controlling agent composed of a compound represented by Chemical Formula (D-1).

(S)-1: A mixed solvent of propylene glycol monomethyl ether acetate/propylene glycol monomethyl ether=60/40 (mass ratio)

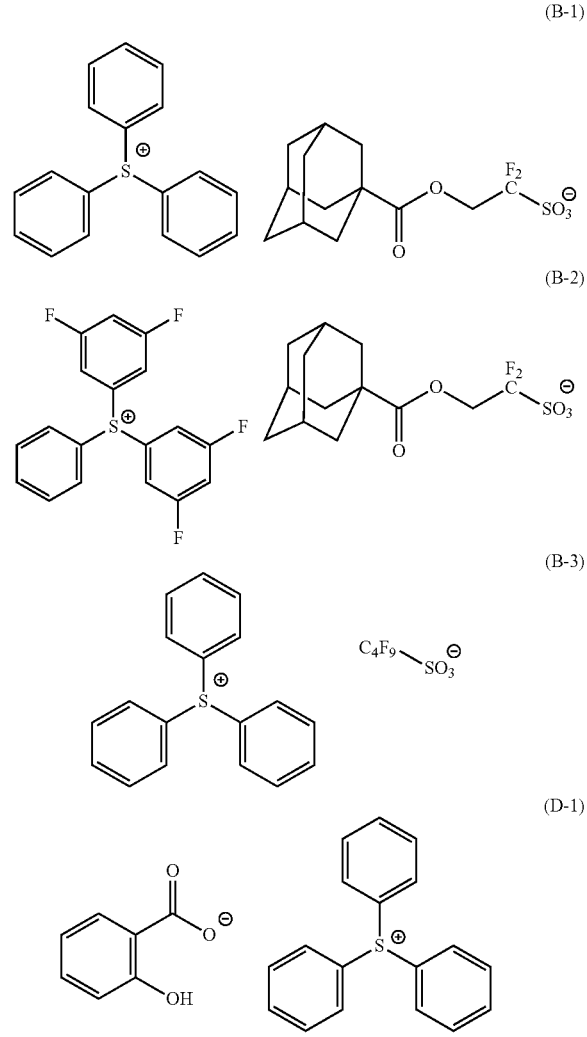

<Formation of Resist Pattern>

The resist composition of each Example was applied onto an 8-inch silicon substrate which had been subjected to a hexamethyldisilazane (HMDS) treatment using a spinner, the coated wafer was subjected to a post-apply baking (PAB) treatment on a hot plate at a temperature of 110° C. for 60 seconds so that the coated wafer was dried to form a resist film having a film thickness of 50 nm.

Next, the resist film was subjected to drawing (exposure) to obtain a target contact hole pattern (hereinafter, referred to as a "CH pattern") in which holes having a diameter of 32 nm were arranged at equal spacings (pitch: 64 nm) by using an electron beam lithography apparatus JEOL-JBX-9300FS (manufactured by JEOL Ltd.) at an acceleration voltage of 100 kV. Thereafter, a post-exposure baking (PEB) treatment was carried out on the resist film at 110° C. for 60 seconds.

Subsequently, alkali development was carried out at 23° C. for 60 seconds using a 2.38% by mass tetramethylammonium hydroxide (TMAH) aqueous solution "NMD-3" (product name, manufactured by TOKYO OHKA KOGYO CO., LTD.).

Thereafter, rinsing was carried out with pure water for 15 seconds.

As a result of the above, a CH pattern in which holes having a diameter of 32 nm were arranged at equal spacings (pitch: 64 nm) was formed in all the examples.

Regarding the resist compositions of Comparative Examples 2, 4, 5, 8, and 10, poor resolution occurred, and a CH pattern in which target holes having a diameter of 32 nm were arranged at equal spacings (pitch: 64 nm) could not be formed.

[Evaluation of Optimum Exposure Amount (Eop)]

According to <Formation of resist pattern> described above, an optimum exposure amount Eop ($\mu C/cm^2$) with which a CH pattern having a target size is formed was determined. The results are shown in Tables 4 and 5 as "Eop ($\mu C/cm^2$)".

[Evaluation of Critical Dimension Uniformity (CDU) of Pattern Size]

The CH pattern formed according to "Formation of resist pattern" described above was observed from the upper side of the CH pattern, and the hole diameter (nm) of each of 40 holes in the CH pattern was measured with a length measuring scanning electron microscope (SEM, acceleration voltage: 300 V, product name: S-9380, manufactured by Hitachi High-Tech Corporation). Triple value ($3\sigma$) of the standard deviation ($\sigma$) calculated from the measurement result was determined. The results are shown in Table 3 as "CDU (nm)".

The smaller the value of $3\sigma$ obtained as described above, the higher the level of the critical dimension (CD) uniformity of holes formed in the resist film.

[Evaluation of Limiting Resolution]

The hole diameter (nm) of the pattern resolved when forming a CH pattern by gradually reducing the exposure amount from the optimum exposure amount Eop ($\mu C/cm^2$) with which a CH pattern having a target size was formed according to <Formation of resist pattern> described above was determined using a scanning electron microscope S-9380 (manufactured by Hitachi High-Tech Corporation). The results are shown in Tables 4 and 5 as "Limiting resolution (nm)".

TABLE 4

|  | PAB (° C.) | PEB (° C.) | Eop [$\mu C/cm^2$] | CDU [nm] | Limiting resolution [nm] |
| --- | --- | --- | --- | --- | --- |
| Example 1 | 110 | 110 | 100 | 4.2 | 24 |
| Example 2 | 110 | 110 | 90 | 4.3 | 24 |
| Example 3 | 110 | 110 | 85 | 4.8 | 32 |
| Example 4 | 110 | 110 | 95 | 4.4 | 26 |
| Example 5 | 110 | 110 | 90 | 4.4 | 26 |
| Comparative Example 1 | 110 | 110 | 200 | 4.8 | 30 |
| Comparative Example 2 | 110 | 110 | Poor resolution | | |
| Example 6 | 110 | 110 | 105 | 4.4 | 24 |
| Example 7 | 110 | 110 | 95 | 4.6 | 28 |
| Example 8 | 110 | 110 | 85 | 4.8 | 28 |
| Comparative Example 3 | 110 | 110 | 180 | 4.6 | 32 |
| Comparative Example 4 | 110 | 110 | Poor resolution | | |
| Example 9 | 110 | 110 | 90 | 4.8 | 26 |
| Example 10 | 110 | 110 | 95 | 4.8 | 26 |
| Comparative Example 5 | 110 | 110 | Poor resolution | | |

TABLE 5

| | PAB (° C.) | PEB (° C.) | Eop [μC/cm²] | CDU [nm] | Limiting resolution [nm] |
|---|---|---|---|---|---|
| Example 11 | 110 | 110 | 105 | 4.0 | 24 |
| Example 12 | 110 | 110 | 100 | 4.6 | 28 |
| Example 13 | 110 | 110 | 105 | 4.2 | 24 |
| Comparative Example 6 | 110 | 110 | 105 | 5.6 | 32 |
| Example 14 | 110 | 110 | 110 | 4.2 | 26 |
| Example 15 | 110 | 110 | 105 | 4.4 | 28 |
| Example 16 | 110 | 110 | 85 | 4.6 | 32 |
| Comparative Example 7 | 110 | 110 | 155 | 5.0 | 30 |
| Comparative Example 8 | 110 | 110 | Poor resolution | | |
| Example 17 | 110 | 110 | 100 | 4.2 | 24 |
| Example 18 | 110 | 110 | 95 | 4.6 | 26 |
| Comparative Example 9 | 110 | 110 | 200 | 4.8 | 30 |
| Example 19 | 110 | 110 | 150 | 4.6 | 30 |
| Example 20 | 110 | 110 | 140 | 5.0 | 32 |
| Comparative Example 10 | 110 | 110 | Poor resolution | | |

As shown in Tables 4 to 5, it has been confirmed that it is possible to achieve high sensitivity and form a resist pattern having good CDU and good resolution with the resist compositions of Examples as compared with the resist compositions of Comparative Examples.

The resist compositions of Comparative Examples 1, 3, 5, 7, 9, and 10, which each contain the polymeric compounds (A-4), (A-9), (A-13), (A-19), (A-23), and (A-25), the polymeric compounds having a constitutional unit derived from the compound (m-a1-1) or (m-a1-2), were inferior in sensitivity to the resist compositions of Examples. This is presumed to be because in the compounds (m-a1-1) and (m-a1-2), the terminal of CC is a hydrogen atom, and thus the constitutional units each derived from the compounds (m-a1-1) and (m-a1-2) has high compatibility with the developing solution but had low acid reactivity.

The resist compositions of Comparative Examples 2, 4, 6, and 8, which each contain the polymeric compounds (A-5), (A-10), (A-16), and (A-20), the polymeric compounds having a constitutional unit derived from the compound (m-a1-3) or (m-a1-4), were inferior in CDU and resolution to the resist compositions of Examples. This is presumed to be because the constitutional units derived from the compounds (m-a1-3) and (m-a1-4) have a highly hydrophobic cyclic hydrocarbon group at the terminal of the side chain and thus have low compatibility with the developing solution.

While preferred embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description and is only limited by the scope of the appended claims.

What is claimed is:

1. A resist composition which generates acid upon exposure and exhibits changed solubility in a developing solution under action of acid, the resist composition comprising:
    a resin component (A1) which exhibits changed solubility in a developing solution under action of acid,
    wherein the resin component (A1) has a constitutional unit (a01) derived from a compound represented by General Formula (a0-1):

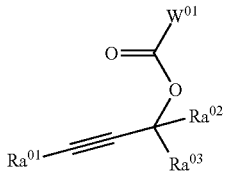

(a0-1)

wherein $W^{01}$ represents a polymerizable group-containing group, $Ra^{01}$ represents a linear or branched hydrocarbon group, and $Ra^{02}$ and $Ra^{03}$ each independently represent a hydrocarbon group which may have a substituent.

2. The resist composition according to claim 1, further comprising:
    an acid generator component (B) which generates acid upon exposure,
    wherein the acid generator component (B) contains a compound represented by General Formula (b-1), a compound represented by General Formula (b-2), or a compound represented by General Formula (b-3):

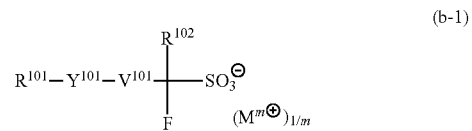

(b-1)

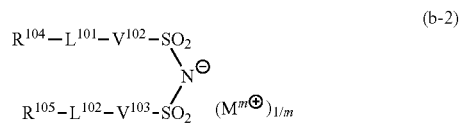

(b-2)

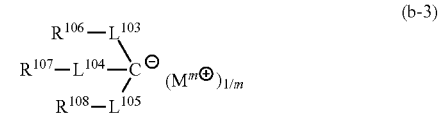

(b-3)

wherein $R^{101}$ and $R^{104}$ to $R^{108}$ each independently represents a cyclic group which may have a substituent, a chain alkyl group which may have a substituent, or a chain alkenyl group which may have a substituent, $R^{104}$ and $R^{105}$ may be bonded to each other to form a ring structure, $R^{102}$ represents a fluorinated alkyl group having 1 to 5 carbon atoms or a fluorine atom, $Y^{101}$ represents a divalent linking group containing an oxygen atom or a single bond, $V^{101}$ to $V^{103}$ each independently represents a single bond, an alkylene group, or a fluorinated alkylene group, $L^{101}$ and $L^{102}$ each independently represents a single bond or an oxygen atom, L103 to L1°5 each independently represents a single bond, —CO—, or —SO$_2$—, $M^{m+}$ represents an m-valent organic cation, and m represents an integer of 1 or more.

3. The resist composition according to claim 2, wherein the acid generator component (B) contains a compound represented by General Formula (b-1-0):

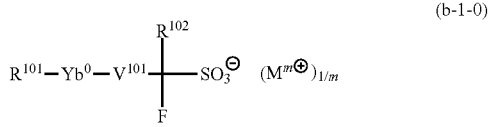

(b-1-0)

wherein $R^{101}$ represents a cyclic group which may have a substituent, a chain alkyl group which may have a substituent, or a chain alkenyl group which may have a substituent, $Yb^0$ represents a divalent linking group containing an oxygen atom, $V^{101}$ represents a single bond, an alkylene group, or a fluorinated alkylene group, $R^{102}$ represents a fluorinated alkyl group having 1 to 5 carbon atoms or a fluorine atom, $M^{m+}$ represents an m-valent organic cation, and m represents an integer of 1 or more.

4. The resist composition according to claim 3, wherein the acid generator component (B) contains a compound represented by General Formula (b-1-1):

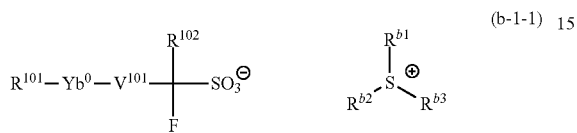

(b-1-1)

wherein $R^{101}$ represents a cyclic group which may have a substituent, a chain alkyl group which may have a substituent, or a chain alkenyl group which may have a substituent, $Yb^0$ represents a divalent linking group containing an oxygen atom, $V^{101}$ represents a single bond, an alkylene group, or a fluorinated alkylene group, $R^{102}$ represents a fluorinated alkyl group having 1 to 5 carbon atoms or a fluorine atom, $R^{b1}$ represents an aryl group having a fluorine atom or an aryl group having a fluorinated alkyl group, and $R^{b2}$ and $R^{b3}$ each independently represents an aryl group which may have a substituent or are bonded to each other to form a ring together with a sulfur atom in the formula.

5. The resist composition according to claim 1, wherein the constitutional unit (a01) is a constitutional unit represented by General Formula (a01-1):

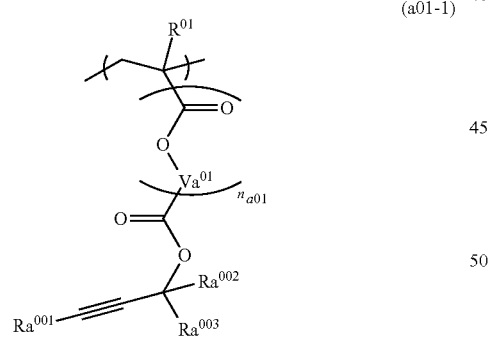

(a01-1)

wherein $R^{01}$ represents a hydrogen atom, an alkyl group having 1 to 5 carbon atoms, or a halogenated alkyl group having 1 to 5 carbon atoms, $Va^{01}$ represents a divalent linking group, $n_{a01}$ represents an integer in a range of 0 to 2, and $Ra^{001}$ to $Ra^{003}$ each independently represents a linear or branched alkyl group.

6. A method of forming a resist pattern, comprising:

forming a resist film on a support using the resist composition according to claim 1;

exposing the resist film; and developing the exposed resist film to form a resist pattern.

7. A compound represented by General Formula (a0-1):

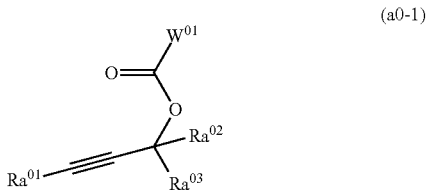

(a0-1)

wherein $W^{01}$ represents a polymerizable group-containing group, $Ra^{01}$ represents a linear or branched hydrocarbon group, and $Ra^{02}$ and $Ra^{03}$ each independently represents a hydrocarbon group which may have a substituent.

8. A resin comprising:

a constitutional unit (a01) derived from a compound represented by General Formula (a0-1):

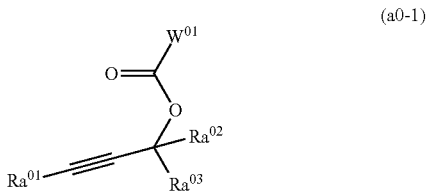

(a0-1)

wherein $W^{01}$ represents a polymerizable group-containing group, $Ra^{01}$ represents a linear or branched hydrocarbon group, and $Ra^{02}$ and $Ra^{03}$ each independently represents a hydrocarbon group which may have a substituent.

9. The resist composition according to claim 1, wherein the resin component (A1) has a constitutional unit (a01) represented by any one of General Formula (a01-1a-1) to (a01-1a-29):

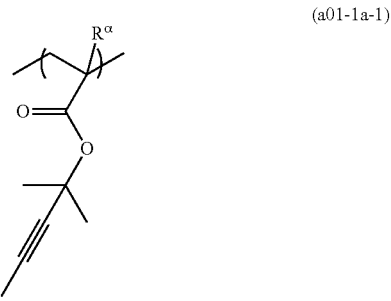

(a01-1a-1)

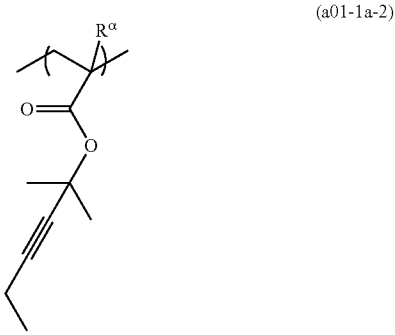

(a01-1a-2)

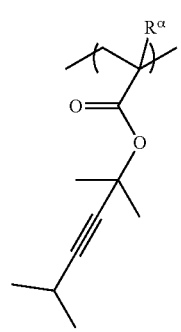 (a01-1a-3)
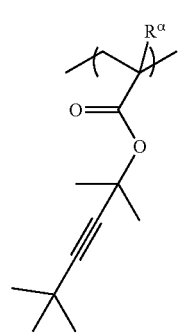 (a01-1a-4)
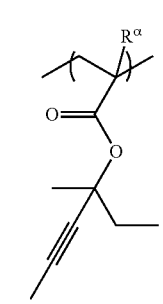 (a01-1a-5)
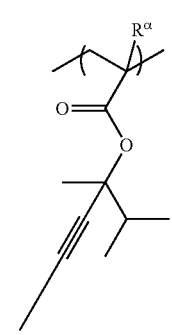 (a01-1a-6)
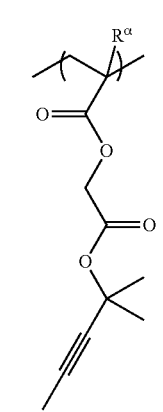 (a01-1a-7)
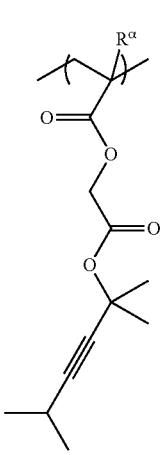 (a01-1a-8)
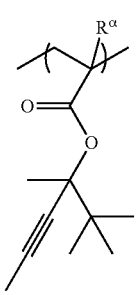 (a01-1a-9)
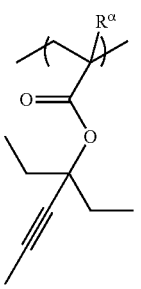 (a01-1a-10)
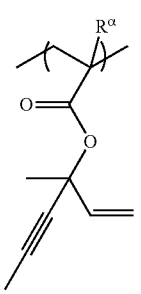 (a01-1a-11)
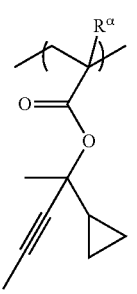 (a01-1a-12)

| | |
|---|---|
| (a01-1a-13) 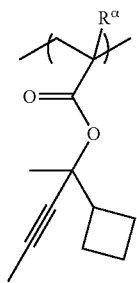 | (a01-1a-18) 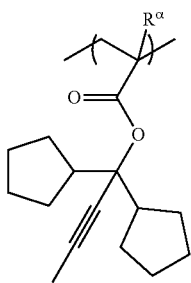 |
| (a01-1a-14) 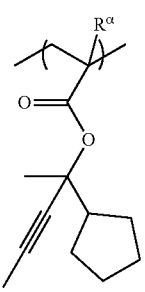 | (a01-1a-19) 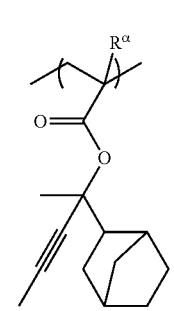 |
| (a01-1a-15) 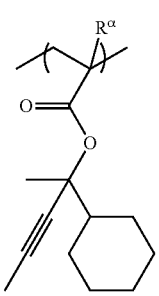 | (a01-1a-20) 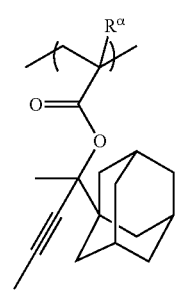 |
| (a01-1a-16) 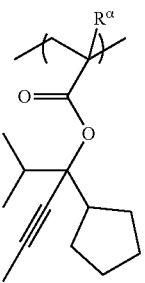 | (a01-1a-21) 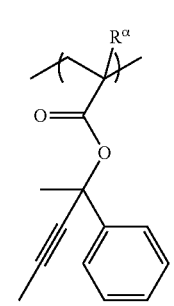 |
| (a01-1a-17) 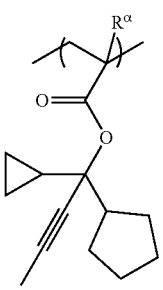 | (a01-1a-22) 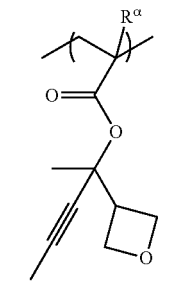 |

(a01-1a-23)
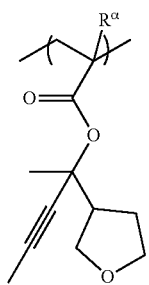
(a01-1a-24)
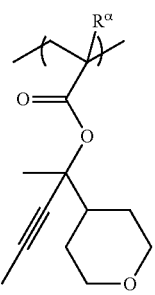
(a01-1a-25)
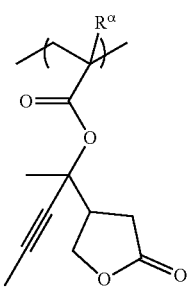
(a01-1a-26)
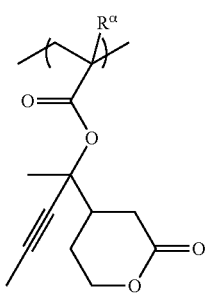
(a01-1a-27)
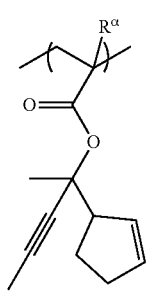
(a01-1a-28)
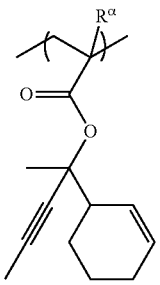
(a01-1a-29)
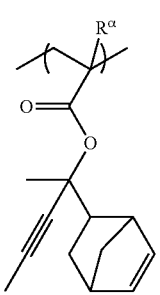
wherein $R^\alpha$ represents a hydrogen atom, a methyl group, or a trifluoromethyl group.
10. The compound according to claim 7, which is represented by any one of Chemical Formula (a01-1m-1) to (a01-1m-30):
(a01-1m-1)
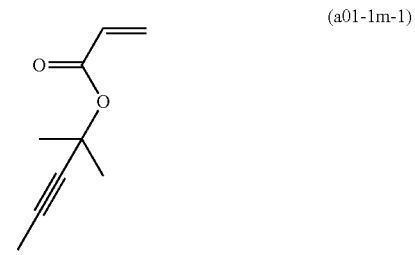
(a01-1m-2)
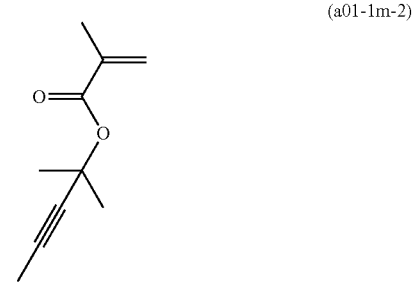
(a01-1m-3)
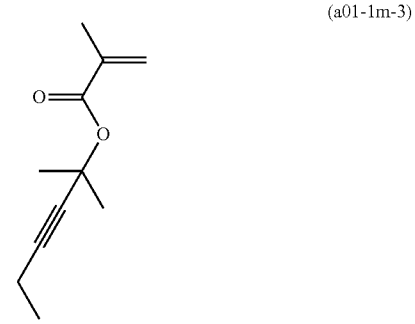

(a01-1m-4)
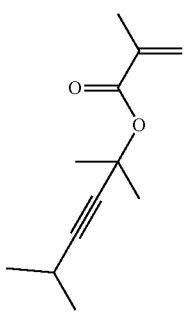
(a01-1m-5)
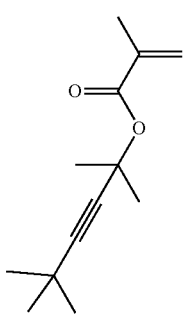
(a01-1m-6)
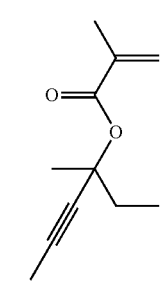
(a01-1m-7)
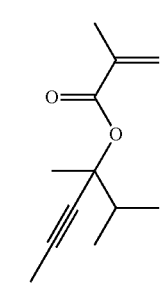
(a01-1m-8)
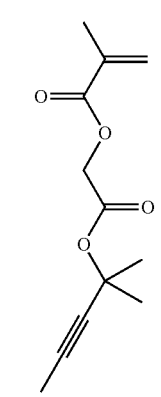
(a01-1m-9)
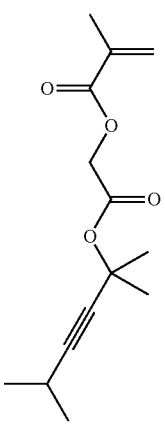
(a01-1m-10)
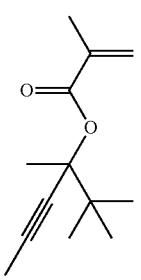
(a01-1m-11)
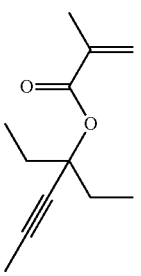
(a01-1m-12)
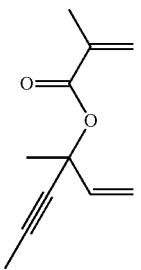
(a01-1m-13)
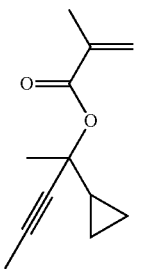

-continued (a01-1m-14)

(a01-1m-15)

(a01-1m-16)

(a01-1m-17)

(a01-1m-18)

(a01-1m-19)

(a01-1m-20)

(a01-1m-21)

(a01-1m-22)

(a01-1m-23)

(a01-1m-24)
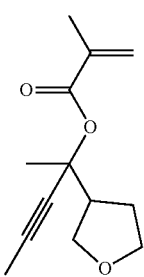
(a01-1m-25)
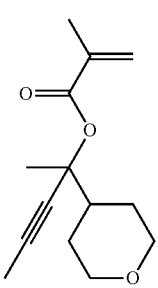
(a01-1m-26)
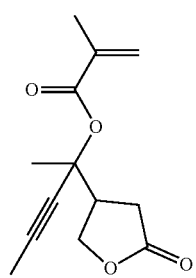
(a01-1m-27)
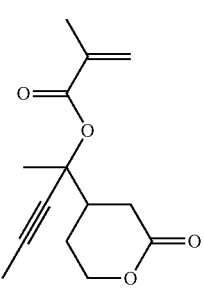
(a01-1m-28)
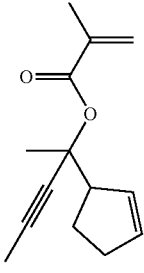
(a01-1m-29)
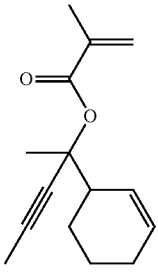
(a01-1m-30)
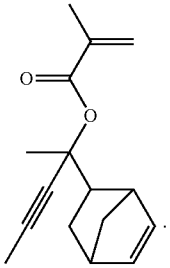
11. The resin according to claim 8,
wherein the constitutional unit (a01) is represented by any one of General Formula (a01-1a-1) to (a01-1a-29):
(a01-1a-1)
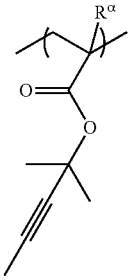
(a01-1a-2)
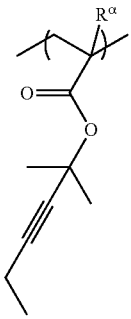
(a01-1a-3)
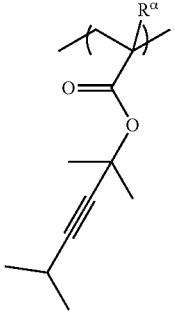

(a01-1a-4)
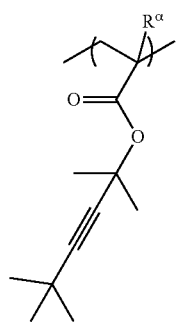
(a01-1a-5)
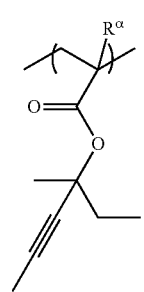
(a01-1a-6)
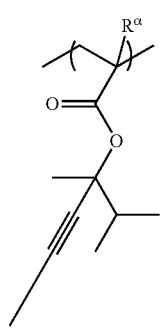
(a01-1a-7)
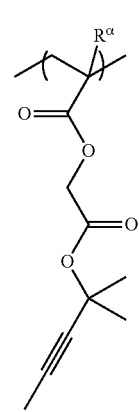
(a01-1a-8)
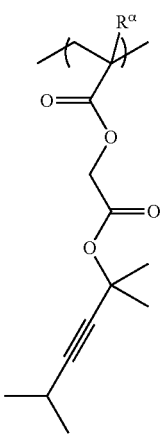
(a01-1a-9)
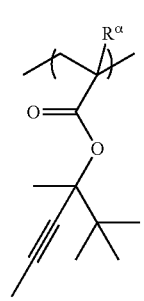
(a01-1a-10)
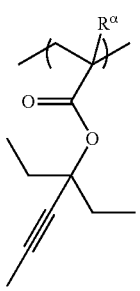
(a01-1a-11)
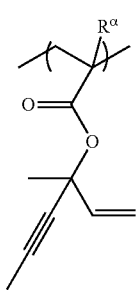
(a01-1a-12)
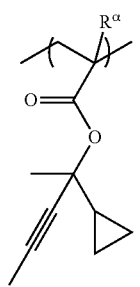

-continued
(a01-1a-13)
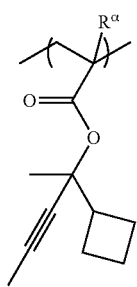
(a01-1a-14)
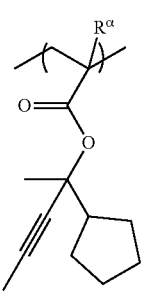
(a01-1a-15)
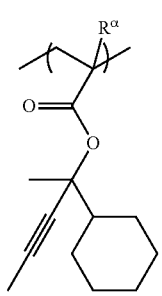
(a01-1a-16)
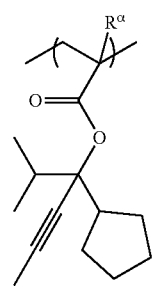
(a01-1a-17)
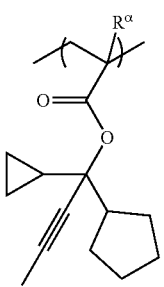
(a01-1a-18)
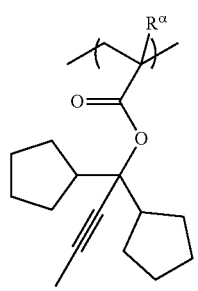
(a01-1a-19)
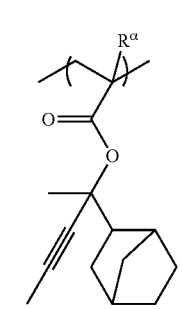
(a01-1a-20)
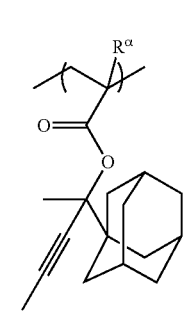
(a01-1a-21)
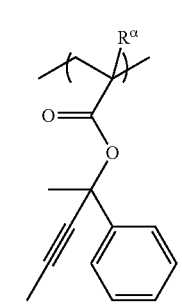
(a01-1a-22)
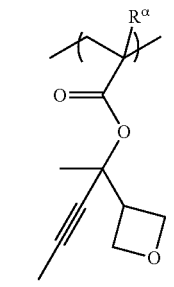

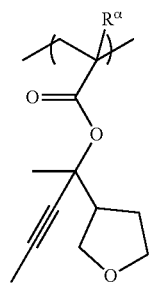
(a01-1a-23)
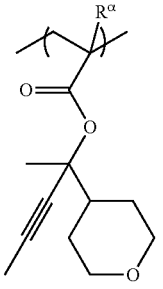
(a01-1a-24)
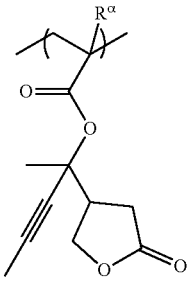
(a01-1a-25)
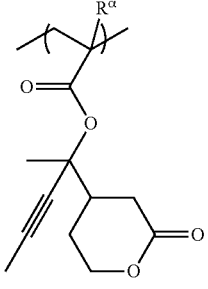
(a01-1a-26)
(a01-1a-27)
(a01-1a-28)
(a01-1a-29)
wherein $R^\alpha$ represents a hydrogen atom, a methyl group, or a trifluoromethyl group.
* * * * *